(12) United States Patent
Zhao

(10) Patent No.: US 7,629,315 B2
(45) Date of Patent: Dec. 8, 2009

(54) COMPOSITIONS FOR BLOCKING THE INHIBITORY EFFECT OF HUMAN CRP ON HUMAN LEPTIN

(75) Inventor: Allan Z. Zhao, Sewickley, PA (US)

(73) Assignee: University of Pittsburgh of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 11/327,596

(22) Filed: Jan. 6, 2006

(65) Prior Publication Data

US 2006/0206948 A1  Sep. 14, 2006

Related U.S. Application Data

(60) Provisional application No. 60/659,757, filed on Mar. 9, 2005.

(51) Int. Cl.
*A61K 38/00* (2006.01)
(52) U.S. Cl. .......................... 514/12; 530/300
(58) Field of Classification Search ....................... None
See application file for complete search history.

(56) References Cited

U.S. PATENT DOCUMENTS

| | | | |
|---|---|---|---|
| 4,179,337 A | 12/1979 | Davis et al. | |
| 5,252,714 A | 10/1993 | Harris et al. | |
| 6,048,837 A * | 4/2000 | Friedman et al. | 514/2 |
| 6,072,047 A * | 6/2000 | Rauch et al. | 536/23.5 |
| 6,475,984 B2 * | 11/2002 | Kirwin et al. | 514/2 |
| 6,777,388 B1 | 8/2004 | Grasso et al. | |
| 6,849,714 B1 | 2/2005 | Bridon et al. | |
| 2002/0037553 A1 | 3/2002 | Al-Barazanji et al. | |
| 2002/0107211 A1 | 8/2002 | Friedman et al. | |
| 2005/0038609 A1 | 2/2005 | Benner | |
| 2005/0250690 A1 | 11/2005 | Gonzalez et al. | |

FOREIGN PATENT DOCUMENTS

| | | |
|---|---|---|
| EP | 0 154 316 A2 | 9/1985 |
| EP | 0 401 384 A1 | 12/1989 |
| WO | WO 90/14363 | 11/1990 |
| WO | WO 93/05722 | 4/1993 |
| WO | WO 95/34670 | 12/1995 |
| WO | WO 96/23520 A | 8/1996 |
| WO | WO 96/31526 | 10/1996 |
| WO | WO 96/35787 | 11/1996 |
| WO | WO 96/41865 | 12/1996 |
| WO | WO 97/06816 | 2/1997 |
| WO | WO 97/16550 A | 5/1997 |
| WO | WO 97/31898 | 9/1997 |
| WO | WO 97/31899 | 9/1997 |
| WO | WO 97/46585 | 12/1997 |

OTHER PUBLICATIONS

Campfield et al., Science 280: 1383-1387, 1998.*
Grasso et al., Endocrinol. 138: 1413-1418, 1997.*
Jeffrey M. Friedman et al., "Leptin and the regulation of body weight in mammals", Nature, vol. 395, Oct. 22, 1998, p. 763-770.
Rexford S. Ahima et al., "Leptin", Annu. Rev. Physiol., 2000, 62:413-437.
Yiying Zhang et al., "Positional cloning of the mouse obese gene and its human homologue", Nature, vol. 372, Dec. 1, 1994, pp. 425-432.
Gwo-Hwa Lee et al., "Abnormal splicing of the leptin receptor in diabetic mice", Nature, vol. 379, Feb. 15, 1996, pp. 632-635.
Amy H. Luke et al., "Leptin and body composition of Nigerians, Jamaicans and US Blacks [1-3]" Am J. Clin Nutr. 1998: 67:391-396.
Peter J. Havel, "Leptin productin and action: relevance to energy balance in humans [1-3]", Am J Clin Nutr 1998; 67:35-356.
Steven B. Heymsfield et al., "Recombinant Leptin for Weight Loss in Obese and Lean Adults", Jama, Oct. 27, 1999—vol. 282, No. 16, pp. 1568-1575.
Christian Bjorbaek et al., "The Role of SOCS-3 in Leptin Signaling and Leptin Resistance", The Journal of Biological Chemistry, vol. 274, No. 42, Oct. 15, 1999, pp. 30059-30065.
Zhuowei Wang et al., "Leptin Resistance of Adipocytes in Obesity: Role of Suppressors of Cytokine Signaling", Biochemical and Biophysical Research Communications, 277, 20—26, 2000.
Michael W. Schwartz et al., "Cerebrospinal fluid leptin levels: Relationship to plasma levels and to adiposity in humans", Nature Medicine, vol. 2, No. 5, May 1996, pp. 589-593.
M. Maachi et al., "Systemic low-grade inflammation is related to both circulating and adipose tissue TNFα, leptin and IL-6 levels in obese women", International Journal of Obesity (2004) 28, 993-997.
Trisha Gura, "Leptin Not Impressive in Clinical Trial", Science, vol. 286, Oct. 29, 1999, pp. 881-882.
James T. Willerson MD et al., "Inflammation as a Cardiovascular Risk Factor", Circulation Jun. 1, 2004, pp. II-2-II-10.
Matthias B. Shulze et al., "C-Reactive Protein and Incident Cardiovascular Events Among Men with Diabetes", Diabetes Care, vol. 27, No. 4, Apr. 2004, pp. 889-894.
Anna U. Bielinska et al., "DNA Complexing with Polyamidoamine Dendrimers: Implications for Transfection", Bioconjugate Chem. 1999, 10, 843-850.
Tsutomu Kazumi et al., "C-Reactive Protein in Young, Apparently Healthy Men: Associations With Serum Leptin, QTc Interval, and High-Density Lipoprotein-Cholesterol", Metabolism, vol. 52, No. 9, Sep. 2003, pp. 1113-1116.
Paul M. Ridker MD et al., "High-sensitivity C-reactive protein, inflammation, and cardiovascular risk: from concept to clinical practive to clinical benefit", American Heart Journal Jul. 2004, pp. 519-526.

(Continued)

Primary Examiner—Robert Landsman
Assistant Examiner—Gyan Chandra
(74) Attorney, Agent, or Firm—Stephen A. Bent; Foley & Lardner LLP

(57) ABSTRACT

Leptin controls the production of C-Reactive Protein (CRP), which, in turn, interacts with leptin to diminish its ability to signal satiety and reduce food intake. The interactions between leptin and CRP can be exploited to screen for agents capable of disrupting the leptin-CRP interaction, and thereby improve leptin signaling. Such agents can be used to reduce body weight, adiposity, and alleviate insulin resistance and diabetes.

20 Claims, 24 Drawing Sheets

OTHER PUBLICATIONS

Goran Rajs et al., "C-Reactive Protein Concentrations in Cerebral Spinal Fluid in Gram-Positive and Gram-Negative Bacterial Meningitis", Clinical Chemistry, 48, No. 3, 2003, pp. 591-592.

Jonas Emsley et al., "Structure of pentameric human serum amyloid P component", Nature, vol. 367, Jan. 27, 1994, pp. 338-345.

M. J. Roberts et al., "Chemistry for peptide and protein PEGylation", Advanced Drug Delivery Reviews 54 (2002) 459-476.

M. Friedman-Einat et al., "Serum leptin activity in obese and lean patients", Regulatory Peptides, 111 (2003) 77-82.

Hebok Song et al., "In vitro mortility of AtKCBP, a calmodulin-binding kinesin protein of Arabidopsis" Proc. Natl. Acac. Sci. USA, vol. 94, pp. 322-327, Jan. 1997.

Jing-Ning Huan et al., "Adipocyte-selective Reduction of the Leptin Receptors Induced by Antisense RNA Leads to Increased Adiposity, Dyslipidemia, and Insulin Resistance", The Journal of Biological Chemistry, vol. 278, No. 46, Issue of Nov. 14, 2003, pp. 45638-45650.

P. Mistrik et al., "BiaCore analysis of leptin-leptin receptor interaction: evidence for 1:1 stoichiometry", Analytical Biochemistry, 327 (2004) 271-277.

F.C. De Beer et al., "Isolation and characterization of C-reactive protein and serum amyloid P component in the rat", Immunology 1982, 45, 55-70.

Christian Vaisse et al., "Leptin activation of Stat3 in the hypothalamus of wild-type and ob/ob mice but not db/db mice", Natural Genetics, vol. 14, Sep. 1996, pp. 95-97.

Allan Z. Zhao et al., "A phosphatidylinositol 3-kinase—phosphodiesterase 3B-cyclc AMP pathway in hypothalamic action of leptin on feeding", Nature Neuroscience, vol. 5, No. 8, Aug. 2002, pp. 727-728.

Kevin D. Niswender et al., "Key enzyme in leptin-induced anorexia", Nature, vol. 413, Oct. 25, 2001, pp. 794-795.

F.L. Graham et al., "A New Technique for the Assay of Infectivity of Human Adenovirus 5 DNA", Virology 52, 456-467 (1973).

John Devereux et al., "A comprehensive set of sequence analysis programs for the VAX", Nucleic Acids Research, vol. 12, No. 1, 1984, pp. 387-395.

Humberto Carrillo et al., "The Multiple Sequence Alignment Problem in Biology", Siam J. Appl. Math. vol. 48, No. 5, Oct. 1988, pp. 1073-1082.

Gilbert Chu et al., "SV40 DNA transfection of cells in suspension: analysis of the efficiency of transcription and translation of T-antigen", Gene, 13, (1981) 197-202.

Margaret L.M. Anderson et al., "Quantitative Filter Hybridisation—Chapter 4", Nucleic acid hyridisation a practical approach, 1985, pp. 73-111.

Stephen Altschul et al., "Basic Local Alignment Search Tool", J. Mol. Biol. (1990) 215, 403-410.

Joachim W. Engels et al., "Gene Synthesis", Angew. Chem. Int. Ed. Engl. 28, (1989) 716-734.

Paul A. Kitts et al., "A Method for Producing Recombinant Baculovirus Expression Vectors at High Frequency", BioTechniques vol. 14, No. 5 (1993), pp. 810-817.

Verne A. Luckow et al., "Baculovirus systems for the expression of human gene products", Current Opinion in Biotechnology, 1993, 4: 564-572.

Verne A. Luckow et al., "Efficient Generation of Infectious Recombinant Baculoviruses by Site-Specific Transposon-Mediated Insertion of Foreign Genes into a Baculovirus Genome Propagated in *Escherichia coli*", Journal of Virology, vol. 67, No. 8, Aug. 1993, pp. 4566-4579.

Christophe Benoist et al., "In vivo sequence requirements of the SV40 early promoter region", Nature, vol. 290, Mar. 26, 1981, pp. 304-310.

Tadashi Yamamoto et al., "Identification of a Fuctional Promoter in the Long Terminal Repeat of Rous Sarcoma Virus", Cell. vol. 22, 787-797, Dec. 1980.

Michael J. Wagner et al., "Nucleotide sequence of the thymidine kinase gene of herpes simplex virus type 1", Proc. Natl. Acad. Sci. USA vol. 78, No. 3, pp. 1441-1445, Mar. 1981.

Ralph L. Brinster et al., "Regulation of metallothionein—thymidine kinase fusion plasmids injected into mouse eggs", Nature, vol. 294, Mar. 4, 1982, pp. 39-42.

Lydia Villa-Komaroll et al., "A bacterial clone synthesizing proinsulin", Proc. Natl. Acad. Sci. USA, vol. 75, No. 8, pp. 3727-3731, Aug. 1978.

Herman A. De Boer et al., "The tac promoter: A functional hybrid derived from the trp and lac promoters", Proc. Natl. Acad. Sci. USA, vol. 80, pp. 21-25, Jan. 1983.

Gail Urlaub et al., "Isolation of Chinese hamster cell mutants deficient in dihydrofolate reductase activity", Proc. Natl. Acad. Sci. USA, vol. 77, No. 7, pp. 4216-4220, Jul. 1980.

Fiona A. O. Marston et al., "Solubilization of protein aggregates", Methods in Enzymology, vol. 182, (1985), pp. 264-277.

R. B. Merrifield, "Solid Phase Peptide Synthesis. I. The Synthesis of Tetrapeptide", J. Am. Chem. Soc., Jul. 20, 1963, pp. 2149-2154.

Richard A. Houghten, "General method for the rapid solid-phase synthesis of large numbers of peptides: Specificity of antigen-antibody interaction at the level of individual amino acids", Proc. Natl. Acad. Sci. USA, vol. 82, pp. 51315135, Aug. 1985.

Richard W. Roberts et al., "RNA-peptide fusions for the in vitro selection of peptides and proteins", Proc. Natl. Acad. Sci. USA. vol. 95, pp. 12297-12302, Nov. 1997.

Richard W. Roberts, "Totally in vitro protein selection using mRNA—protein fusions and ribosome display", Current Opinion in Chemical Biology, 1999, 3: 268-273.

Anthanassios Giannis et al., "Peptidomimetrics in Drug Design", Advances in Drug Research, vol. 29, 1997, pp. 1-78.

Amy S. Ripka et al., "Peptidomimetic Design", Next Generation Therapeutics, 1998, Curr. Opin. Chem. Bio. 2: 441-452.

Garland R. Marshall, "A Hierarchical Approach to Peptidomimetric Design", Tetrahedron vol. 49, No. 17, pp. 3547-3558, 1993.

Franz Hefti, "Neurotrophic Factor Therapy for Nervous System Degenerative Diseases", Journal of Neurobiology, vol. 25, No. 11, pp. 1418-1435, 1994.

Julie .A. Meyers et al., "Leptin and immune function: integrating hte evidence", Nutrition Research, 25 (2005) 791-803.

Database UniProt Nov. 8, 2005 XP002415440; Database Accession No. Q3I1 R5.

Abu S.M. Shamsuzzaman et al., "Independent Association Between Plasma Leptin and C-Reactive Protein in Healthy Humans", Circulation, May 11, 2004, pp. 2181-2185.

Alexander J. Szalai et al., "Varied Biologic Functions of C-Reactive Protein", Immunologic Research 2002:26/1—3:279-287.

Alicja Jozkowicz et al., "Helper-dependent adenoviral vectors in experimental gene therapy", Acta Biochimica Polonica, vol. 52, No. 3/2005, pp. 589-599.

Allan Z. Zhao et al., "Attenuation of insulin secretion by insulin-like growth factor 1 is mediated through activation of phosphodiesterase 3B", Proc. Natl. Acad. Sci. vol. 94, pp. 3223-3228, Apr. 1997.

Anthony C. Forster et al., "Programming peptidomimetic syntheses by translating genetic codes designed de novo", PNAS, vol. 100, No. 11, May 27, 2003, pp. 6353-6357.

Celine Adessi et al., "Converting a Peptide into a Drug: Strategies to Improve Stability and Bioavailability", Current Medicinal Chemistry, 2002, 9, pp. 963-978.

Chris J. Hukshorn et al., "Leptin and the Proinflammatory State Associated with Human Obesity", The Journal of Clinical Endocrinology & Metabolism 89(4):1773-1778, (2004).

D. Aronson et al., "Obesity is the major determinant of elevated C-reactive protein in subjects with the metabolic syndrome", International Journal of Obesity, 2004, 28, pp. 674-679.

Desmond G. Higgins et al., "Clustal: a package for performing multiple sequence alignment on a microcomputer", Gene, 73 (1988) 237-244.

Desmond G. Higgins et al., "Fast and sensitive multiple sequence alignments on a microcomputer", Cabios Communications vol. 5, No. 2, 1989, pp. 151-153.

Florence Corpet, "Multiple sequence alignment with hierarchical clustering", Nucleic Acids Research, vol. 16, No. 22, 1988, pp. 10881-10890.

Gema Fruühbeck, "Review Article Intracellular Signalling Pathways Activated by Leptin", Biochem J. (2006), 393, 7-20.

Inder M. Verma et al., "Gene Therapy—promises, problems and prospects", Nature, vol. 389, Sep. 18, 1997, pp. 239-242.

James A. Patch et al., "Mimicry of bioactive peptides via non-natural, sequence-specific peptidomimetic oligomers", Current Opinion in Chemical Biology 2002, 6:872-877.

Jean-Louis Boulay et al., "Expression vectors and delivery systems Web alert", Current Opinion in Biotechnology, 1998, 9:445.

Jerming Tseng et al., "Binding of Human C-Reactive Protein (CRP) to Plasma Fibronectin Occurs Via the Phosphorylcholine-Binding Site", Molecular Immunology, vol. 25, No. 8, pp. 679-686, 1988.

Joel K. Elmquist et al., "Unraveling the central nervous system pathways underlying responses to leptin", Nature Neuroscience, vol. 1, No. 6, Oct. 1998, pp. 445-450.

Jose F. Caro et al., "Decreased cerebrospinal-fluid/serum leptin ratio in obesity: a possible mechanism for leptin resistance", The Lancet vol. 348, Jul. 20, 1996, pp. 159-161.

K. Zahedi et al., "Major Acute-Phase Reactant Synthesis During Chronic Inflammation in amyloid-susceptible and -Resistant Mouse Strains", Inflammation, vol. 15, No. 1, 1991, pp. 1-14.

Koji Yasojima et al., "Human neurons generate C-reactive protein and amyloid P: upregulation in Alzheimer's disease", Brain Research 887, (2000) 80-89.

Michael W. Schwartz et al., "Evidence That Plasma Leptin and Insulin Levels Are Associated with Body Adiposity via Different Mechanisms", Diabetes Cares, vol. 20, No. 9, Sep. 1997, pp. 1476-1481.

Peter A. Antinozzi et al., "Metabolic Engineering With Recombinant Adenoviruses", Annu. Rev. Nutr. 1999, 19:511-544.

Richard A. Morgan et al., "Human Gene Therapy", Annu. Rev. Biochem. 1993, 62:191-217.

Robert V. Considine, Ph.D., "Human Leptin: An Adipocyte Hormone with Weight-Regulatory and Endocrine Functions", Seminars in Vascular Medicine, vol. 5, No. 1, 2005, pp. 15-24.

Ronald M. Mackintosh et al., "The Effects of Leptin Administration in Non-obese Human Subjects", Obesity Research, vol. 9, No. 8, Aug. 2001, pp. 462-469.

Ruth B.S. Harris et al., "A Leptin Dose-Response Study in Obese (ob/ob) and Learn (+/?) Mice", Endocrinology, vol. 139, No. 1, 1998, pp. 8-19.

Saul B. Needleman et al., "A General Method Applicable to the Search for Similarities in the Amino Acid Sequence of Two Proteins", J. Mol. Biol. (1970) 48, pp. 443-453.

Scott McGinnis et al., "Blast: at the core of a powerful and diverse set of sequence analysis tools", Nucleic Acids Research, 2004, vol. 32, pp. W20-W25.

Stephen C. Woods et al., "Signals That Regulate Food Intake and Energy Homeostasis", Science, vol. 280, May 29, 1998, pp. 1378-1383.

Stephen F. Altschul et al., "Issues in searching molecular sequence databases", Nature Genetics, vol. 6, Feb. 1994, pp. 119-129.

Stephen F. Altschul, "A Protein Alignment Scoring System Sensitive at All Evolutionary Distances", J. Mol. Evol. (1993) 36:290-300.

Temple F. Smith et al., "Comparison of Biosequences", Advances in Applied Mathematics, 2, 482-489, 1981.

William R. Pearson et al., "Improved tools for biological sequence comparison", Proc. Natl. Acad. Sci. USA, vol. 85, pp. 2444-2448, Apr. 1988.

William R. Pearson, "Using the FASTA Program to Search Protein and DNA Sequence Databases", Methods in Molecular Biology, vol. 24, Computer Analysis of Sequence Data, Part 1, 1994, pp. 307-331.

Xiaoqiu Huang et al., "Parallelization of a local similarity algorithm", Cabios, vol. 8, No. 2, 1992, pp. 155-165.

Zoltan Ivics et al., "Molecular Reconstruction of Sleeping Beauty, a Tc1-like Transposon from Fish, and Its Transposition in Human Cells", Cell, vol. 91, 501-510, Nov. 14, 1997.

Interview Summary dated Jan. 26, 2009 for U.S. Appl. No. 11/683,555.

Final Action dated Oct. 29, 2008 for U.S. Appl. No. 11/683,555.

Interview Summary dated Jul. 22, 2008 for U.S. Appl. No. 11/683,555.

Non-Final Action dated Apr. 11, 2008 for U.S. Appl. No. 11/683,555.

Non-Final Action dated Feb. 4, 2008 for U.S. Appl. No. 11/683,555.

Non-Final Office Action dated May 22, 2009 U.S. Appl. No. 11/683,555.

* cited by examiner serum
↓
① Leptin-Sepharose Affinity column
② Wash with 15x column volume washing buffer
③ Elute with 10 mM Glycine pH=2
④ Neutralized in 50 mM Tris (pH=9.5)

FIG. 2A gi/33086642  Mass: 116387  Score: 95  Queries matched: 2
BaZ-693 [Rattus norvegicus]
☐ Check to include this hit in error tolerant search or archive report

| Query | Observed | Mr(expt) | Mr(calc) | Delta | Miss | Score | Expect | Rank | Peptide |
|-------|----------|----------|----------|-------|------|-------|--------|------|---------|
| ☑ 1 | 1231.60 | 1230.59 | 1230.65 | -0.06 | 0 | 40 | 0.085 | 1 | R.VFSPNVLNWR.A (SEQ ID.NO:6) |
| ☑ 3 | 1526.73 | 1525.72 | 1525.79 | -0.07 | 0 | 55 | 0.0021 | 1 | K.TSFNEILLFWTR.G (SEQ ID.NO:7) |

Proteins matching the same set of peptides:
gi/ 60552095  Mass: 25452  Score: 95  Queries matched: 2
C-reactive protein, petaxin related [Rattus norvegicus]

FIG. 2B

CRP_HUMAN C-reactive protein precursor
Accession: GI:117486

| Scan(s) | Peptide | | MH+ | z | Score XC | Coverage Delta Cn |
|---------|---------|---|-----|---|----------|-------------------|
| 2568 | -.KAFVFPKESDTSYVSLK.- | (SEQ ID.NO:8) | 1946.03000 | 2 | 4.85 | 0.50 |
| 2622 | -.YEVQGEVFTKPQLWP.- | (SEQ ID.NO:9) | 1820.92000 | 2 | 3.25 | 0.32 |
| 2679 | -.QDNEILIFWSK.- | (SEQ ID.NO:10) | 1392.72000 | 2 | 4.12 | 0.28 |
| 2718 | -.RQDNEILIFWSK.- | (SEQ ID.NO:11) | 1548.82000 | 2 | 4.88 | 0.37 |
| 2783 | -.ALKYEVQGEVFTKPQLWP.- | (SEQ ID.NO:12) | 2133.14000 | 2 | 3.76 | 0.48 |
| 4613 | -.GYSIFSYATK.- | (SEQ ID.NO:13) | 1136.56000 | 2 | 3.46 | 0.46 |

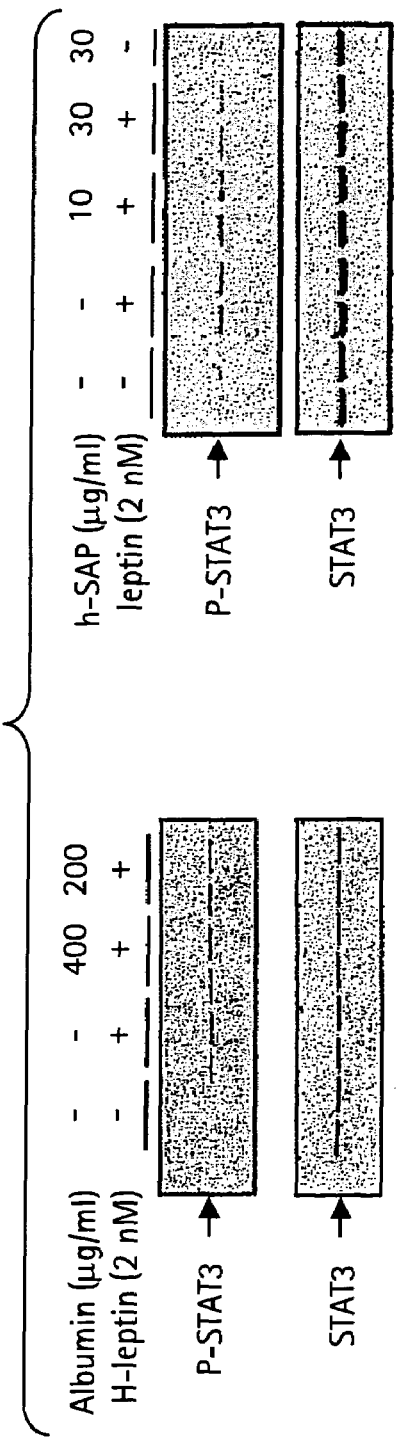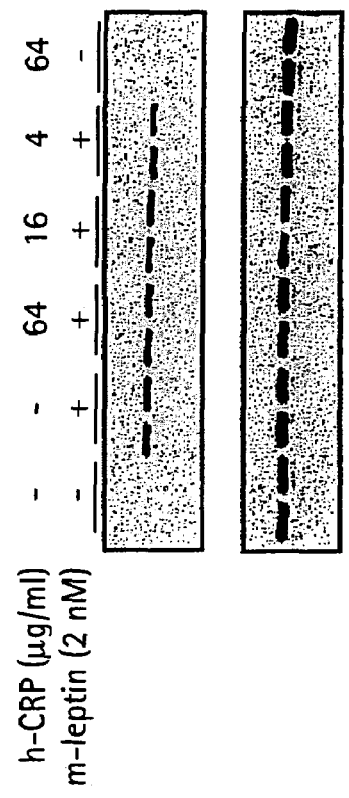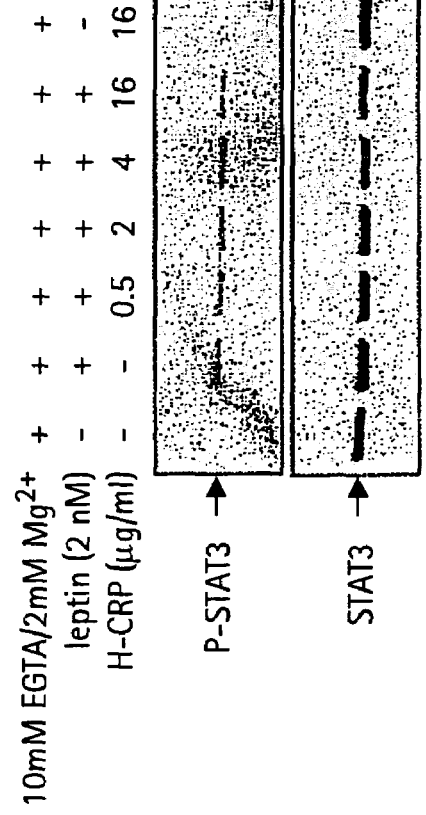
FIG. 4F
FIG. 4G
FIG. 4H

Peptide-E Composition
NH2-LAFSKSCHLPWASGLETLDSLGGVLEA-COOH (SEQ ID. NO:2)

FIG. 11

Complete human leptin protein sequences (SEQ ID. NO:4)

MHWGTLCGFL WLWPYLFYVQ AVPIQKVQDD TKTLIKTIVT RINDISHTQS 50
VSSKQKVTGL DFIPGLHPIL TLSKMDQTLA VYQQILTSMP SRNVIQISND 100
LENLRDLLHV LAFSKSCHLP WASGLETLDS LGGVLEASGY STEVVALSRL 150
QGSLQDMLWQ LDLSPGC 167

Underlined section represents the sequences of Peptide-E (SEQ ID. NO:2)

FIG. 12

Peptide-E: NH$_2$-LAFSKSCHLPWASGLETLDSLGGVLEA-COOH  (SEQ ID. NO:2)

S-C-H-L-P-W  (SEQ ID. NO:3)

SEQUENCE LISTING

<160> NUMBER OF SEQ ID NOS: 13

<210> SEQ ID NO 1
<211> LENGTH: 81
<212> TYPE: DNA
<213> ORGANISM: Homo sapiens

<400> SEQUENCE: 1
ctggccttct ctaagagctg ccacttgccc tgggccagtg gcctggagac cttggacagc    60 ctgggggtg tcctggaagc t                81

<210> SEQ ID NO 2
<211> LENGTH: 27
<212> TYPE: PRT
<213> ORGANISM: Homo sapiens

<400> SEQUENCE: 2

Leu Ala Phe Ser Lys Ser Cys His Leu Pro Trp Ala Ser Gly Leu Glu
1               5                   10                  15

Thr Leu Asp Ser Leu Gly Gly Val Leu Glu Ala
            20                  25

<210> SEQ ID NO 3
<211> LENGTH: 6
<212> TYPE: PRT
<213> ORGANISM: Homo sapiens

<400> SEQUENCE: 3

Ser Cys His Leu Pro Trp
1               5

<210> SEQ ID NO 4
<211> LENGTH: 167
<212> TYPE: PRT
<213> ORGANISM: Homo sapiens

<400> SEQUENCE: 4

Met His Trp Gly Thr Leu Cys Gly Phe Leu Trp Leu Trp Pro Tyr Leu
1               5                   10                  15

Phe Tyr Val Gln Ala Val Pro Ile Gln Lys Val Gln Asp Asp Thr Lys
            20                  25                  30

Thr Leu Ile Lys Thr Ile Val Thr Arg Ile Asn Asp Ile Ser His Thr
        35                  40                  45

Gln Ser Val Ser Ser Lys Gln Lys Val Thr Gly Leu Asp Phe Ile Pro
    50                  55                  60

Gly Leu His Pro Ile Leu Thr Leu Ser Lys Met Asp Gln Thr Leu Ala
65                  70                  75                  80

Val Tyr Gln Gln Ile Leu Thr Ser Met Pro Ser Arg Asn Val Ile Gln
                85                  90                  95

Ile Ser Asn Asp Leu Glu Asn Leu Arg Asp Leu Leu His Val Leu Ala
            100                 105                 110

Phe Ser Lys Ser Cys His Leu Pro Trp Ala Ser Gly Leu Glu Thr Leu
        115                 120                 125

Asp Ser Leu Gly Gly Val Leu Glu Ala Ser Gly Tyr Ser Thr Glu Val
    130                 135                 140

Val Ala Leu Ser Arg Leu Gln Gly Ser Leu Gln Asp Met Leu Trp Gln
145                 150                 155                 160

Leu Asp Leu Ser Pro Gly Cys
                165

<210> SEQ ID NO 5
<211> LENGTH: 6
<212> TYPE: PRT
<213> ORGANISM: Homo sapiens

<400> SEQUENCE: 5

Trp Pro Leu His Cys Ser
1               5

<210> SEQ ID NO 6
<211> LENGTH: 12
<212> TYPE: PRT
<213> ORGANISM: rattus norvegicus

<400> SEQUENCE: 6

Arg Val Phe Ser Pro Asn Val Leu Asn Trp Arg Ala
1               5                   10

<210> SEQ ID NO 7
<211> LENGTH: 14
<212> TYPE: PRT
<213> ORGANISM: Rattus norvegicus

<400> SEQUENCE: 7

Lys Thr Ser Phe Asn Glu Ile Leu Leu Phe Trp Thr Arg Gly
1               5                   10

<210> SEQ ID NO 8
<211> LENGTH: 17
<212> TYPE: PRT
<213> ORGANISM: Homo sapiens

<400> SEQUENCE: 8

Lys Ala Phe Val Phe Pro Lys Glu Ser Asp Thr Ser Tyr Val Ser Leu
1               5                   10                  15

Lys

<210> SEQ ID NO 9
<211> LENGTH: 15
<212> TYPE: PRT
<213> ORGANISM: Homo sapiens

<400> SEQUENCE: 9

Tyr Glu Val Gln Gly Glu Val Phe Thr Lys Pro Gln Leu Trp Pro
1               5                   10                  15

<210> SEQ ID NO 10
<211> LENGTH: 11
<212> TYPE: PRT
<213> ORGANISM: Homo sapiens

<400> SEQUENCE: 10

Gln Asp Asn Glu Ile Leu Ile Phe Trp Ser Lys
1               5                   10

<210> SEQ ID NO 11
<211> LENGTH: 12
<212> TYPE: PRT
<213> ORGANISM: Homo sapiens

<400> SEQUENCE: 11

Arg Gln Asp Asn Glu Ile Leu Ile Phe Trp Ser Lys
1               5                   10

<210> SEQ ID NO 12
<211> LENGTH: 18
<212> TYPE: PRT
<213> ORGANISM: Homo sapiens

<400> SEQUENCE: 12

Ala Leu Lys Tyr Glu Val Gln Gly Glu Val Phe Thr Lys Pro Gln Leu
1               5                   10                  15

```
Trp Pro

<210> SEQ ID NO 13
<211> LENGTH: 10
<212> TYPE: PRT
<213> ORGANISM: Homo sapiens

<400> SEQUENCE: 13

Gly Tyr Ser Ile Phe Ser Tyr Ala Thr Lys
1               5                   10
```

COMPOSITIONS FOR BLOCKING THE INHIBITORY EFFECT OF HUMAN CRP ON HUMAN LEPTIN

CROSS-REFERENCE TO RELATED APPLICATIONS

This application claims the benefit of priority of U.S. Provisional Patent Application No. 60/659,757, filed on Mar. 9, 2005, and having a common inventor. U.S. Provisional Patent Application No. 60/659,757 is incorporated by reference in its entirety herein.

STATEMENT REGARDING FEDERALLY SPONSORED RESEARCH OR DEVELOPMENT

Portions of the research leading to embodiments in this application were supported in part by an NIH grant (1RO1DK064383-01).

BACKGROUND OF THE INVENTION

1. Field of the Invention

Prophylaxis and treatment of obesity, coronary artery disease, infertility, diabetes, and related diseases and conditions can be effected through novel C-reactive protein antagonist polypeptides and nucleic acid molecules encoding the same. Also provided are pharmaceutical compositions and methods for the treatment, amelioration, and/or prevention of diseases and/or conditions associated with C-reactive protein.

2. Background

Molecular and physiological evidence accumulated in the past decade has firmly established leptin as a critical adipocyte hormone involved in regulation of energy-intake and expenditure, weight, fertility, as well as glucose and lipid metabolism. J. M. Friedman et al., 1998, *Nature* 395, 763; R. S. Ahima et al., 2000, *Ann. Rev. Physiol.* 62, 413.

Null mutations in leptin or leptin receptor genes cause hyperphagia, severe obesity, sterility, and diabetes in both rodents and humans. R. S. Ahima et al., 2000, *Ann. Rev. Physiol.* 62, 413; Y. Zhang et al., 1994, *Nature* 372, 425; G. H. Lee et al., 1996, *Nature* 379, 632. Leptin replacement in these animals as well as in humans with leptin deficiency can have profound effects to reverse obesity. However, the great majority of overweight and obese individuals have elevated rather than depressed levels of leptin. A. H. Luke et al., 1998, *Am. J. Clin. Nutr.* 67, 391; P. J. Havel, 1998, *Am. J. Clin. Nutr.* 67, 355; and M. W. Schwartz et al., 1997, *Diabetes Care* 20, 1476.

It remains to be established why high leptin concentration in obesity fails to suppress food intake and reduce adiposity. Therapeutic trials with exogenous leptin that further raised leptin levels have failed to induce meaningful weight loss. S. B. Heymsfield et al., 1999, *JA.M.A.* 282, 1568. These observations have spawned the concept of "leptin resistance." T. Gura, 1999, *Science* 286, 881 ( ); C. Bjorbaek et al., *J. Biol. Chem.* 274, 30059 (Oct. 15, 1999).

Recent studies attempted to elucidate potential molecular mechanisms. Elevation of a suppressor of cytokine signaling-3 (SOCS-3), perhaps induced by leptin itself, might diminish leptin actions in the central nervous system and pancreatic β-cells. C. Bjorbaek et al., 1999, *J. Biol. Chem.* 274, 30059; Z. Wang et al., 2000, *Biochem. Biophys. Res. Commun.* 277, 20. Those observations do not fully explain leptin resistance. For example, this mechanism does not account for impaired leptin transport into the central nervous system (CNS), which has been consistently observed in obesity. M. W. Schwartz et al., *Nat. Med.* 2, 589 (1996).

C-reactive protein (CRP) is commonly elevated in obesity and is a marker of the low-grade inflammatory state associated with obesity and increased cardiovascular risk of obesity. M. Maachi et al., 2004, *Int. J. Obes. Relat. Metab. Disord.* 28, 993; J. T. Willerson et al., 2004, *Circulation* 109, 112; M. B. Schulze et al., 2004, *Diabetes Care* 27, 889. Elevation of CRP and its relationship to obesity and other disorders has not been adequately explained.

The mechanism by which high leptin concentration fails to influence regulation of energy-intake and expenditure, weight, fertility, and glucose and lipid metabolism in a majority of obese humans remains a mystery. Although some have speculated that there is a form of leptin resistance, no studies have been published showing how this might occur, nor have any studies identified the factors that might influence it. Likewise, there is no accepted explanation why CRP is elevated in obesity and other conditions. As such, CRP may be nothing more than a mere marker for such conditions.

BRIEF SUMMARY OF THE INVENTION

We have found that CRP interacts with leptin (SEQ ID NO:4) to form a leptin-CRP complex. Formation of the leptin-CRP complex leads to leptin resistance. We have found CRP antagonists that deter or reverse formation of leptin-CRP complexes. These CRP antagonists include various oligomers, polypeptides, and proteins. We have also identified nucleic acid molecules encoding those oligomers, polypeptides, and proteins.

In one embodiment an isolated nucleic acid molecule is provided, comprising a nucleotide sequence selected from the group consisting of:

(a) the nucleotide sequence as set forth in SEQ ID NO: 1;

(b) a nucleotide sequence encoding the polypeptide set forth in SEQ ID NO:2;

(c) a nucleotide sequence that hybridizes under moderately or highly stringent conditions to the complement of any of (a) or (b); and (d) a nucleotide sequence complementary to any of (a) to (c).

Another embodiment provides an isolated nucleic acid molecule comprising a nucleotide sequence selected from the group consisting of:

(a) a nucleotide sequence encoding a polypeptide that is at least about 60% identical, at least about 70% identical, at least about 80% identical, at least about 90% identical, at least about 95% identical, or at feast about 99% identical to the polypeptide of SEQ ID NO:2, wherein the encoded polypeptide has an activity of the polypeptide of SEQ ID NO:2;

(b) a region of the nucleotide sequence of SEQ ID NO:1 or (a), encoding a polypeptide fragment of at least about 5 amino acid residues, wherein the polypeptide fragment has an activity of the polypeptide of SEQ ID NO:2, and wherein said polypeptide fragment is not the five amino acid sequence of SEQ ID NO:3;

(c) a region of the nucleotide sequence of SEQ ID NO:1 or any of (a) or (b), wherein said region includes at least 15 consecutive nucleotides from SEQ ID NO:1, and wherein said region is not a region encoding the amino acid sequence of SEQ ID NO:3;

(d) a nucleotide sequence that hybridizes under moderately or highly stringent conditions to the complement of any of (a) to (c); and (e) a nucleotide sequence complementary to any of (a) to (d).

A further embodiment provides an isolated nucleic acid molecule comprising a nucleotide sequence selected from the group consisting of:

(a) a nucleotide sequence encoding a polypeptide of SEQ ID NO:2 with at least one conservative amino acid substitution, wherein the polypeptide has an activity of the polypeptide of SEQ ID NO:2;

(b) a nucleotide sequence encoding a polypeptide of SEQ ID NO:2 with at least one amino acid insertion, wherein the encoded polypeptide has an activity of the polypeptide of SEQ ID NO:2;

(c) a nucleotide sequence encoding a polypeptide of SEQ ID NO:2, with at least one amino acid deletion, wherein the encoded polypeptide has an activity of the polypeptide of SEQ ID NO:2;

(d) a nucleotide sequence encoding a polypeptide of SEQ ID NO:2, having a C- and/or N-terminal truncation, wherein the encoded polypeptide has an activity of the polypeptide of SEQ ID NO:2;

(e) a nucleotide sequence encoding a polypeptide of SEQ ID NO:2, with at least one modification selected from the group consisting of amino acid substitutions, amino acid insertions, amino acid deletions, C-terminal truncation, and N-terminal truncation, wherein the encoded polypeptide has an activity of the polypeptide of SEQ ID NO:2;

(f) a nucleotide sequence of any of (a) to (e) comprising a fragment of at least about 15 nucleotides;

(g) a nucleotide sequence that hybridizes under moderately stringent conditions and/or highly stringent conditions to the complement of any of (a) through (f);

(h) a nucleotide sequence complementary to any of (a) to (g).

Another embodiment provides an isolated polypeptide comprising an amino acid sequence of SEQ ID NO:2.

Another embodiment provides an isolated polypeptide comprising an amino acid sequence selected from the group consisting of:

(a) an amino acid sequence for an ortholog of SEQ ID NO:2;

(b) an amino acid sequence that is at least about 60% identical to the amino acid sequence of SEQ ID NO:2, wherein the polypeptide has an activity of the polypeptide of SEQ ID NO:2;

(c) a fragment of the amino acid sequence of SEQ ID NO:2, comprising at least about 5 amino acid residues, wherein the fragment has an activity of the polypeptide of SEQ ID NO:2, and wherein said fragment is not limited to the amino acid sequence of SEQ ID NO:3.

Another embodiment provides an isolated polypeptide comprising an amino acid sequence selected from the group consisting of:

(a) the amino acid sequence of SEQ ID NO:2, with at least one conservative amino acid substitution, wherein the polypeptide has an activity of the polypeptide of SEQ ID NO:2;

(b) the amino acid sequence of SEQ ID NO:2, with at least one amino acid insertion, wherein the polypeptide has an activity of the polypeptide of the polypeptide of SEQ ID NO:2;

(c) the amino acid sequence of SEQ ID NO:2, with at least one amino acid deletion, wherein the polypeptide has at activity of the polypeptide of SEQ ID NO:2;

(d) the amino acid sequence of SEQ ID NO:2, having a C- and/or N-terminal truncation, wherein the polypeptide has an activity of the polypeptide of SEQ ID NO:2; and (e) the amino acid sequence of SEQ ID NO:2, with at least one modification selected from the group consisting of amino acid substitution, amino acid insertion, amino acid deletion, C-terminal truncation, and N-terminal truncation, wherein the polypeptide has an activity of the polypeptide of SEQ ID NO:2.

Another embodiment provides complexation of a Peptide E polypeptide with a biodegradable polymer, a mucoadhesive polymer, a polymeric nanoparticle, a dendrimer, or polyethyleneglycol (PEG).

Another embodiment provides fusion polypeptides comprising Peptide E polypeptides.

Another embodiment provides complexes of Peptide E nucleic acids with a dendrimer. A dendrimer may be a polyamidamine dendrimer. Complexation of DNA with polyamidamine dendrimers is reported in Bielinska, et al., 1999, *Bioconjug. Chem.* 10(5):843-50.

Another embodiment provides Peptide E oligomers. Peptide E oligomers may include, for example, oligomers comprising five or more Peptide E polypeptide repeat units. Another embodiment provides cyclic and dual polypeptides.

Another embodiment provides an expression vector comprising the isolated nucleic acid molecules set forth herein, recombinant host cells comprising recombinant nucleic acid molecules as set forth herein, and a method of producing a Peptide E polypeptide comprising the host cells and, optionally, isolating the polypeptide.

Another embodiment provides a transgenic non-human animal comprising a nucleic acid molecule encoding a Peptide E polypeptide. The Peptide E nucleic acid molecules are introduced into an animal in away that allows expression and increased levels of a Peptide E polypeptide. The transgenic non-human animal may be, for example, a mammal. A mammal may be, for example, porcine, equine, bovine, or a rodent. A rodent may be, for example, a mouse or a rat.

Another embodiment provides pharmaceutical compositions comprising Peptide E nucleotides, and/or polypeptides, as well as one or more pharmaceutical carriers. The pharmaceutical compositions may be used to provide therapeutically effective amounts of Peptide E nucleotides or polypeptides. Pharmaceutical compositions may include delivery by encasement in liposomes. Another embodiment provides methods of using the polypeptides and nucleotides.

The Peptide E polypeptides and nucleic acid molecules that are provided may be used to treat, prevent, and/or ameliorate diseases, disorders and symptoms of diseases, including but not limited to obesity, inflammation, coronary heart disease, infertility, and diabetes. The Peptide E polypeptides and nucleic acid molecules that are provided may be used to suppress food intake, reduce body weight and adiposity, and alleviate insulin resistance.

Another embodiment provides methods and compositions for disrupting CRP-leptin complex formation, thereby increasing free leptin in the blood and the cerebrospinal fluid. This disruption may include blocking the inhibitory effects of human CRP on leptin. This may restore the effects of leptin in reducing plasma triglycerides and low-density lipid proteins.

1(B): Western blot analysis of the column fractions with specific anti-OBR antibodies. The primary antibody, anti-mouse OBR was directed against a region (aa. 634-aa. 784) that shares high homology across several species (including humans). This antibody also reacted non-specifically with SLIP-3/4 (labeled by "NS"). The specific band for the soluble leptin receptor was indicated. The same antibody also detected rat sOBR at a similar position (not shown).

FIGS. 1 (C & D): Five major SLIPs were identified from the column eluate on a silver-stained SDS gel with apparent molecular weight of 30-, 40-, 65-, 70-, and 90-Kd, correspondingly named as the human (C) or rat (D) SLIP-1, 2, 3, 4, and 5. A fraction of serum leptin could also be co-eluted with SLIPs (indicated by the dashed arrows), which was confirmed in a western blot assay.

Figure 2D:
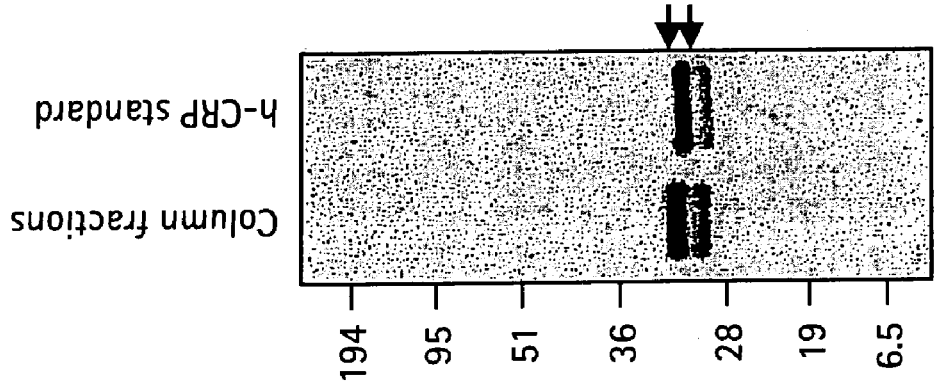

FIG. 2. Identification of SLIP-1 as C-reactive protein:

FIG. 2(A): MALDI-TOF analysis of rat SLIP-1. Two major peaks, a & b, were shown here as the examples to identify r-SLIP-1 as the rat C-reactive protein. FIG. 2(B): Human SLIP-1 was identified as human CRP in a mass-spec analysis (Nano-LC-MS/MS analysis. FIG. 2(C & D): Confirmation of SLIP-1 as C-reactive proteins with specific anti-CRP antibody in western blot assays. The appearance of doublets in the rat CRP blot was a reflection of posttranslational modification (glycosylation) in major portion of the rat CRP polypeptides.

Figure 3A:
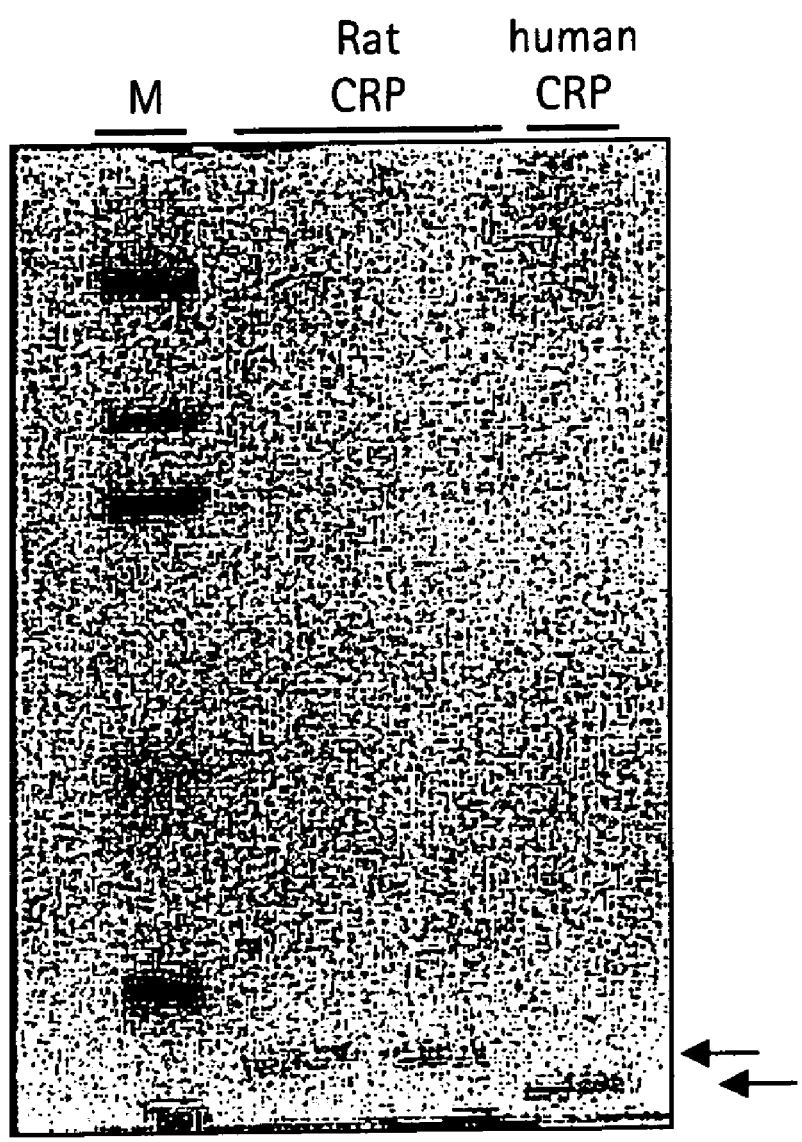
Figure 3B:
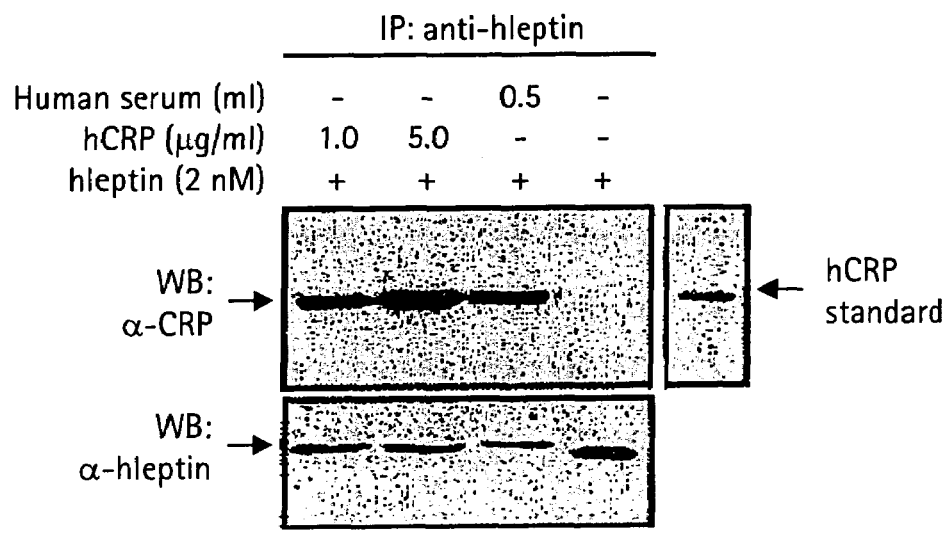
Figure 3C:
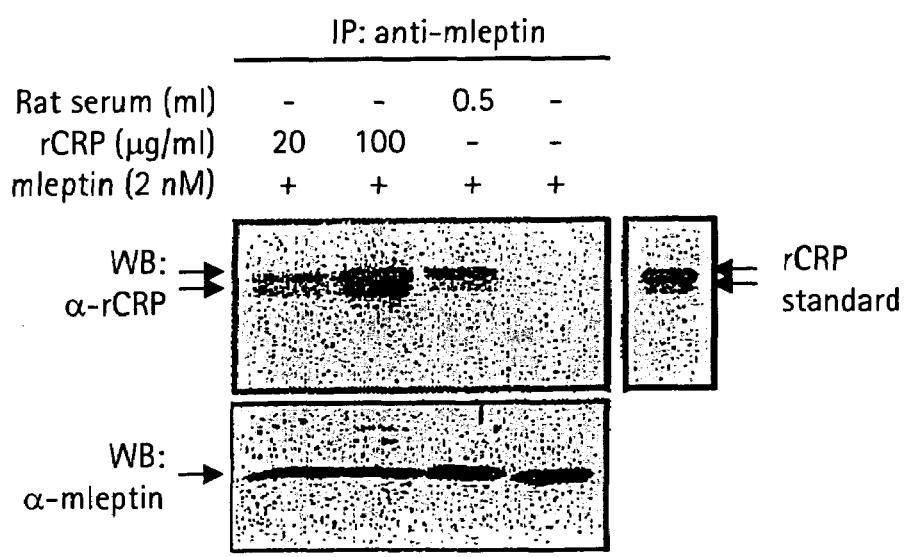
Figure 3D:
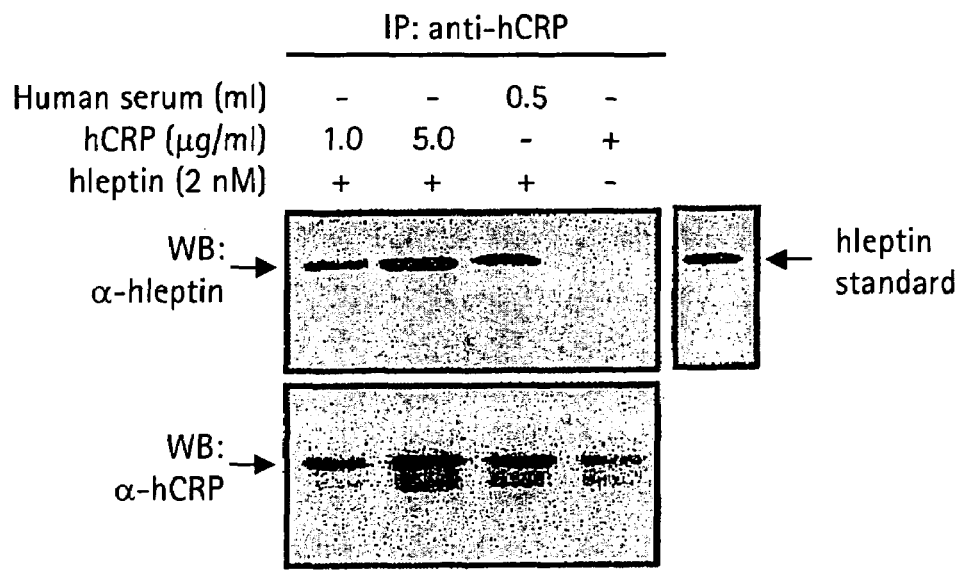

FIG. 3. Demonstration of direct binding of human and rat CRP with leptin through immunoprecipitation:

FIG. 3(A): To explore a physical interaction between CRP and leptin, the direct binding of these proteins was determined in an immunoprecipitation assay. Rat CRP was purified from fresh rat serum to >95% purity employing a previously established affinity-purification protocol. This degree of purity is comparable to that of a human CRP preparation that may be obtained commercially, which was confirmed by mass spectrometry. The purified human- and rat-CRP proteins were pre-mixed with recombinant human and mouse leptin, respectively, before addition of antibodies specific for human- and mouse-leptin. The concentrations of CRP and leptin in the precipitation reaction were all within the physiological ranges that have been observed in humans or rats. In parallel experiments, recombinant leptin was pre-mixed with human- or rat-serum to all direct interaction prior to immunoprecipitation. The protein precipitates obtained were subjected to Western blot assays using specific anti-CRP antibodies. FIG. 3(B): Immunoprecipitation using anti human-leptin could pull down human CRP from both the leptin/CRP mixture and from human serum. FIG. 3(C): Immunoprecipitation using anti mouse-leptin could bring down rat CRP from the leptin and CRP mixture as well as from rat serum. FIGS. 3(D&E): Direct interaction of CRP and leptin is further illustrated, where immunoprecipitation was performed using anti human-CRP and rat CRP-antibodies and was found to pull down leptin proteins.

Figure 3E:
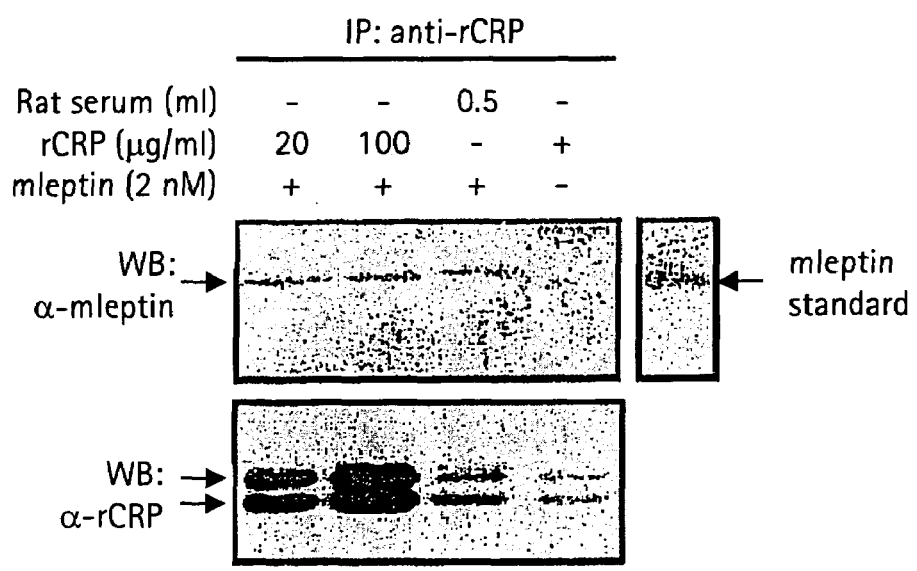
Figure 3F:
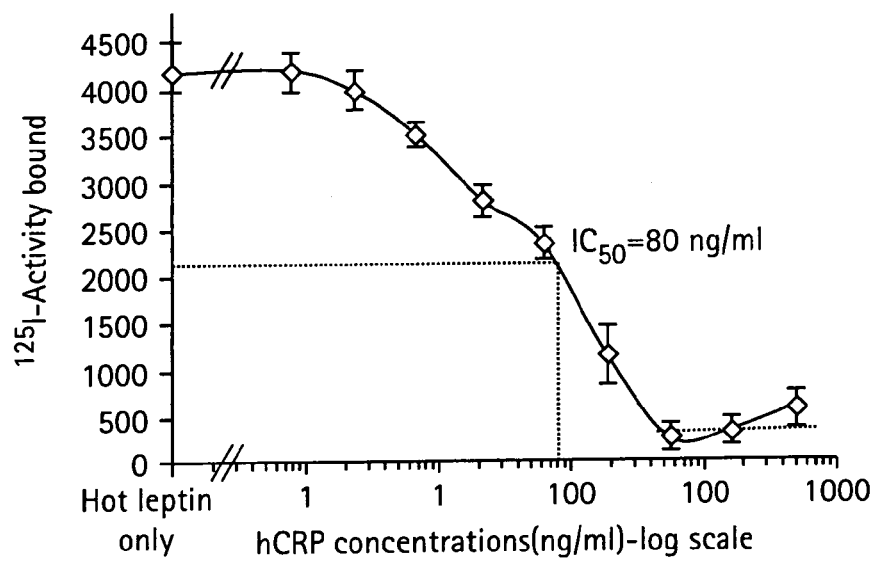
Figure 3G:
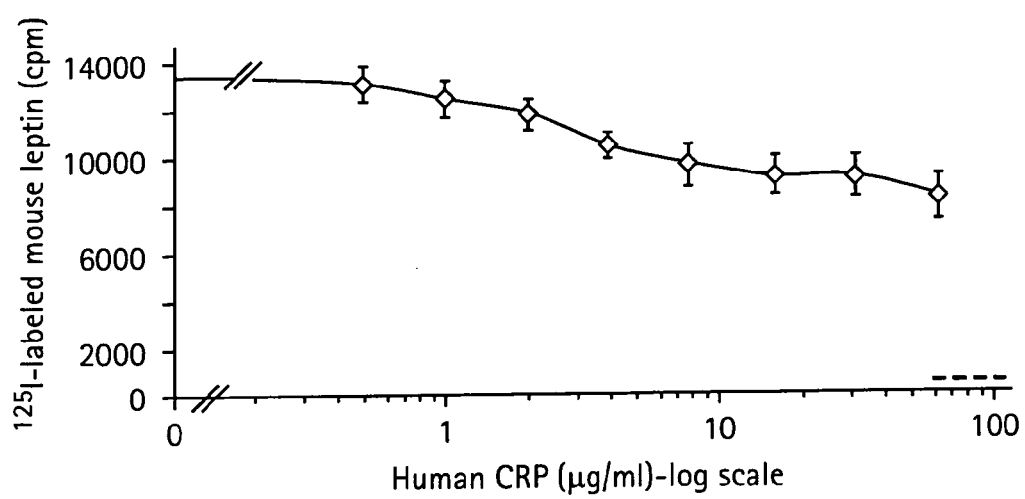

FIG. 3(F): To examine if CRP binding interferes with the stability of human leptin to bind to its receptors, HEK293 cells stably transfected with the long-form human leptin receptor, OB-Rb were used. It was found that the $K_d$ for leptin and its receptors on this cell line was $1.0 \times 10^{-9}$ M. Pre-incubation of human CRP with $^{125}$I-labeled human leptin reduced leptin's binding to its receptors in a dose-dependent manner. The $IC_{50}$ value was approximately 80 ng/ml of CRP in the presence of about 2 ng/ml human leptin, which yielded a molecular ratio of 5.8:1 (CRP:leptin, based on the pentameric structure of CRP). FIG. 3(G): Human CRP displayed lower affinity towards mouse leptin ($IC_{50}$ greater than 64 µg/ml in the presence of about 2 ng/ml mouse leptin. Consistent with this observation, human CRP was found to be less efficient in blocking the signaling capacity of mouse leptin.

FIG. 4. Determination of the effects of purified human or rat CRP on leptin signaling:

FIG. 4(A & B): Attenuating effects of human CRP (A) and rat CRP (B) on leptin-induced tyrosine phosphorylation of STAT3 in a HEK293 cell line stably transfected with OB-Rb. FIG. 4(C): As a control, human serum albumin, when co-incubated with leptin, did not affect the stimulation of STAT3 by leptin. FIG. 4(D): The effect of human CRP on human leptin signaling was also tested in the rat primary hypothalamic neurons with the assays of tyrosine phosphorylation of STAT3 and PI3-kinase activity. FIG. 4(E): Human CRP does not affect human IL6-stimulated tyrosine phosphorylation of STAT3 in human primary hepatocytes. Similarly, rat CRP did not block insulin-stimulated PI3-kinase in differentiated 3T3-L1 adipocytes. FIG. 4(F): Preincubation of human albumin or human serum amyloid P-component (SAP) at the indicated concentrations with human leptin did not significantly alter leptin-stimulated phosphorylation of STAT3. Similarly, human CRP does not affect insulin-stimulated PI3-kinase activity in differentiated 3T3-L1 adipocytes.

FIG. 4(G): The efficient attenuation of leptin signaling by human CRP requires the presence of calcium ions, since addition of excess EGTA to the incubation medium blocked the inhibitory effects of human CRP on human leptin signaling. FIG. 4(H): Consistent with the observation of low affinity between human CRP and mouse leptin (FIG. 3G), high concentrations of human CRP were unable to block leptin-induced STAT3 activation.

FIG. 5. The serum levels of human CRP and human leptin in the infused ob/ob mice:

The serum levels of human CRP (FIGS. 5(A & C)) in the ob/ob mice infused with either a low dosage of (10 µg/day; A) or a high dosage of human CRP (40 µg/day; C). The infused human leptin was controlled at a approximately the same level (FIGS. 5(B & D)).

FIG. 6. The effects of human CRP on leptin-regulated food-intake, body weight, and rectal temperature in the ob/ob mice:

Human CRP was either infused alone or together with human leptin into 8-week old male ob/ob mice with osmotic pumps (#1007D, DURECT). The arrow indicates the day of surgery. Food-intake (FIGS. 6(A & C)) and body weight (FIGS. 6(B & D)) were monitored daily throughout the infusion period (6 days). The low dosage of human CRP only partially blocked leptin's effect (A & C), but the high infusion dosage of human CRP completely blocked the effects of leptin (B & D) in the ob/ob mice. Because of the variations in the body weight of ob/ob mice, the body weight is expressed as a percentage of the pre-surgery body weight. In (A) & (C), n=4 for each group except for saline and leptin group. In addition, human CRP, at the high infusion dosage, completely blocked the effects of leptin on rectal temperature (FIG. 6(E)). In (B), (D), and E, n=5 for the saline group, n=6 for the CRP- and leptin-infused, and n=7 for the group infused with leptin plus CRP. The symbols "*" and "#" indicate P<0.01 and <0.05, respectively, in a two-tailed Student's t-test. In both (A) and (B), P<0.01 for leptin vs. saline, leptin vs. CRP from day 2; P<0.05 for leptin+CRP vs. saline, vs. CRP, and vs. leptin group from day 3. In both (C) and (D), P<0.01 or <0.05 for leptin vs. saline, vs. CRP, and vs. leptin+CRP group from day 3. In addition, P<0.01 for leptin+CRP vs. saline and vs. CRP in (C) on day 2.

Figure 7A:
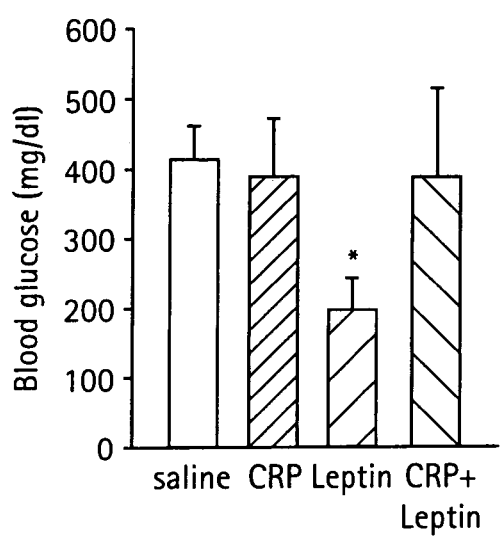
Figure 7B:
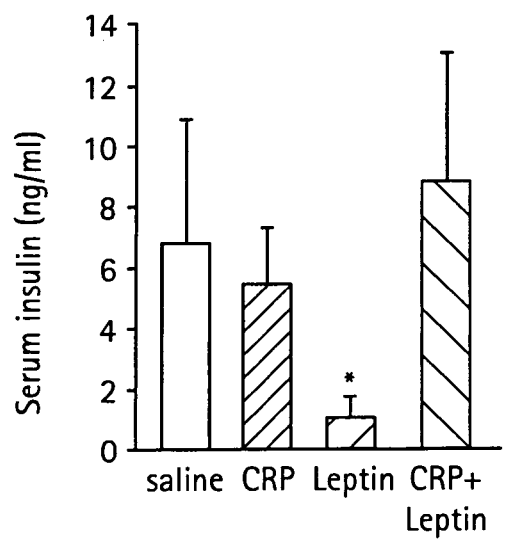
Figure 7C:
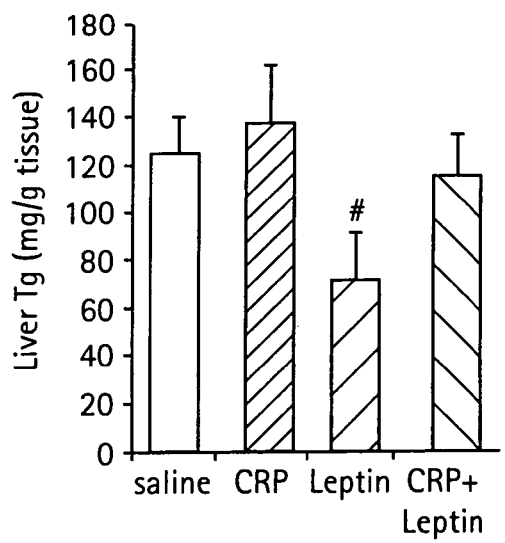
Figure 7D:
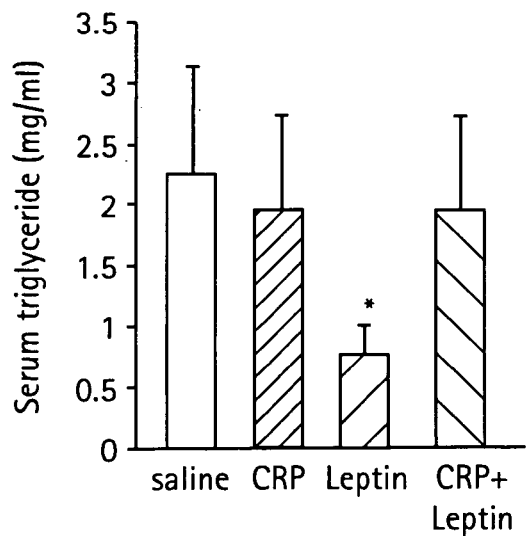
Figure 7E:
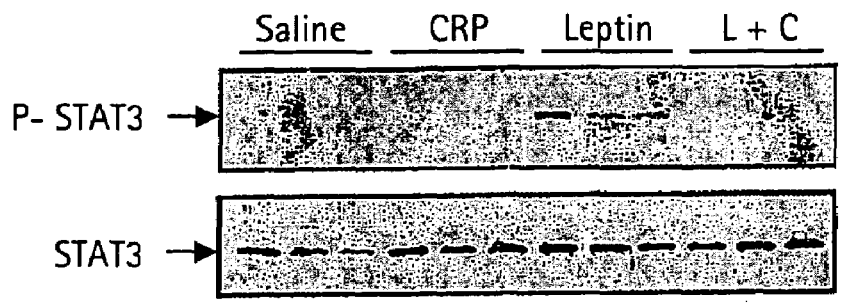
Figure 7F:
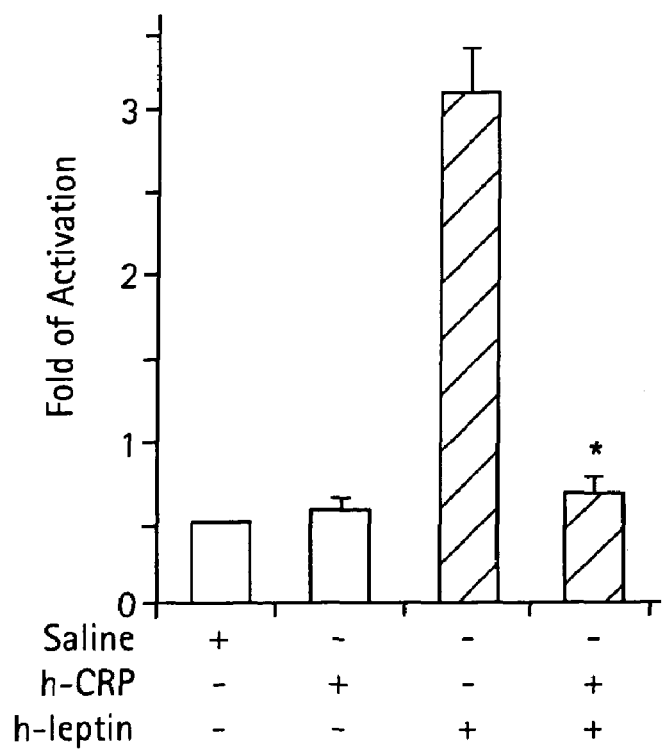

FIG. 7. The effects of human CRP on leptin-induced changes in blood glucose, serum insulin, serum- and hepatic triglyceride levels, and hypothalamic STAT3 activation of the ob/ob mice:

Co-infusion of the high dosage of human CRP completely blocked leptin-induced beneficial effects on the blood glucose (FIG. 7(A)), serum insulin (FIG. 7(B)), serum triglycerides (FIG. 7(C)), and hepatic triglycerides (FIG. 7(D)). The symbols "*" and "#" indicate P<0.01 and <6.05, respectively, in a two-tailed Student's t-test. FIG. 7(E): Western blot analysis of leptin-stimulated STAT3 phosphorylation in the hypothalamic tissues of ob/ob mice. "L+C" represents the samples of ob/ob mice co-infused with human leptin and high dose of CRP. FIG. 7(F): Quantitative evaluation of leptin-induced STAT3 activation based on the analysis of digitally scanned images (such as that in FIG. 7(E)) with NIH-IMAGE6.0 software n=3 per condition. P, 0.05 (8) in a Student's t-test when compared to the leptin group.

Figures 8A, 8B:
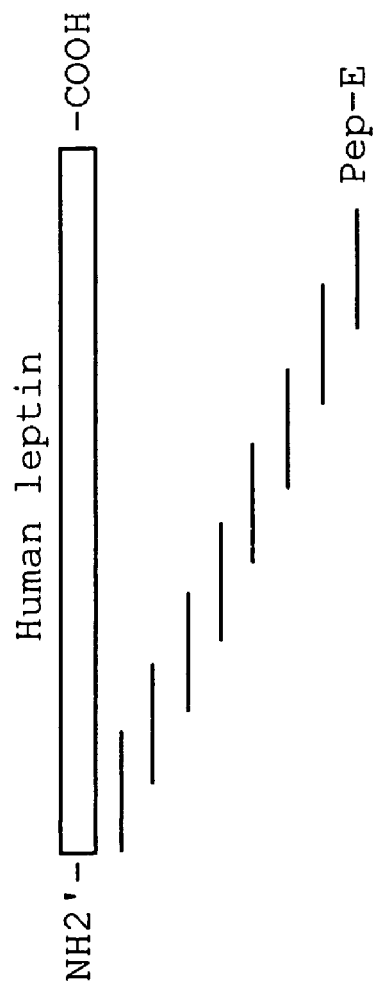

FIG. 8. FIG. 8(A): Schematic representation of the peptide designs intended for mapping the domains on leptin critical for the interaction between human-CRP and leptin. A series of overlapping polypeptides (25-27 amino acids in length) will be chemically synthesized to cover the entire protein sequences of human leptin. Each peptide (except the ones at the NH2- and COOH-termini) will have ten-amino acid overlap with the adjacent peptides. Peptide-E is one of these peptides (Pep-E). FIG. 8(B): The amino acid composition of the Peptide-E.

Figure 9:
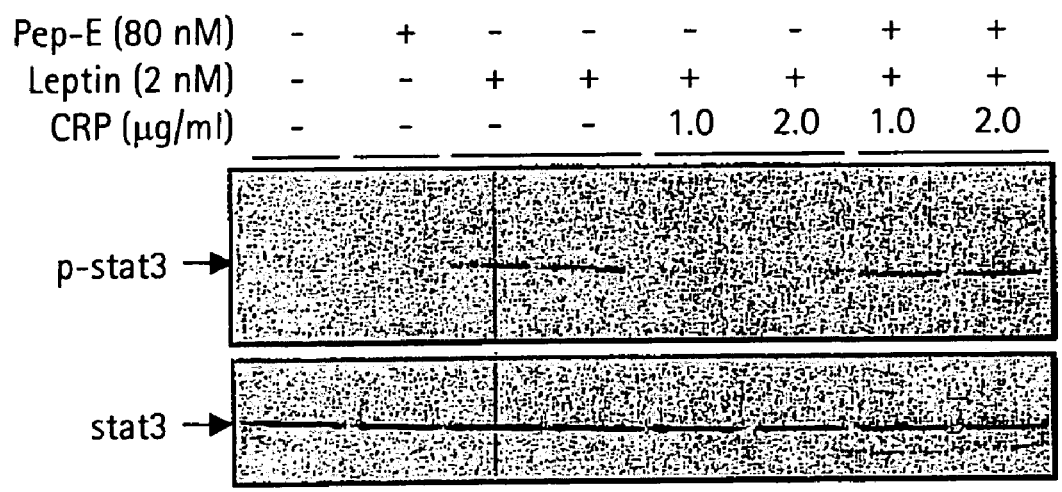

FIG. 9. Western blot analysis of STAT3 activation as reflected by its tyrosine phosphorylation. Human CRP suppressed the activation of STAT3 by leptin, but pre-incubation of Pep-E with human CRP was able to block the inhibitory effect of human CRP on leptin signaling. Peptide-E, by itself, did not induce any changes in STAT phosphorylation.

FIG. 10. Co-fusion of Peptide-E with human CRP and leptin through mini-osmotic pumps into the ob/ob mice restored the physiological effects of human leptin. Infusion dosages for human CRP and leptin were 48 µg/day/mouse and 12 µg/day/mouse, respectively. The infusion rate for Pep-E (P) was 24 µg/day/mouse (medium dosage, abbreviated "m") and 48 µg/day/mouse (high dosage, abbreviated "h"). Food-intake (FIGS. 10(A & C)) and body weight (FIGS. 10(B & D)) were monitored daily throughout the infusion. The arrows in A-D indicate the day of surgery. At the end of infusion, blood samples were collected for the measurement of blood-glucose, human CRP, and human leptin. The serum concentrations of human CRP and human leptin were 0.85±0.1 µg/ml and 18 ng±2 ng/ml, respectively. FIG. 10(E) shows the blood glucose concentrations from the group of mice infused the high dosage of Pep-E (h). The glucose concentration from the mice infused with human CRP and leptin, but NOT with Pep-E was also shown.

FIG. 11. The amino acid sequence of leptin, (SEQ ID NO:4). The underlined portion shows the amino acid sequence of Peptide E (SEQ ID NO:2).

FIG. 12. FIG. 12 shows an amino acid sequence (SEQ ID NO:3) reported in U.S. Pat. No. 6,777,388, to Grasso, et al. It is shown in FIG. 12 in relation to a sequence in a Peptide E polypeptide (SEQ ID NO:2). The amino acid sequences are shown in their biologically relevant L-form.

Figure 13A:
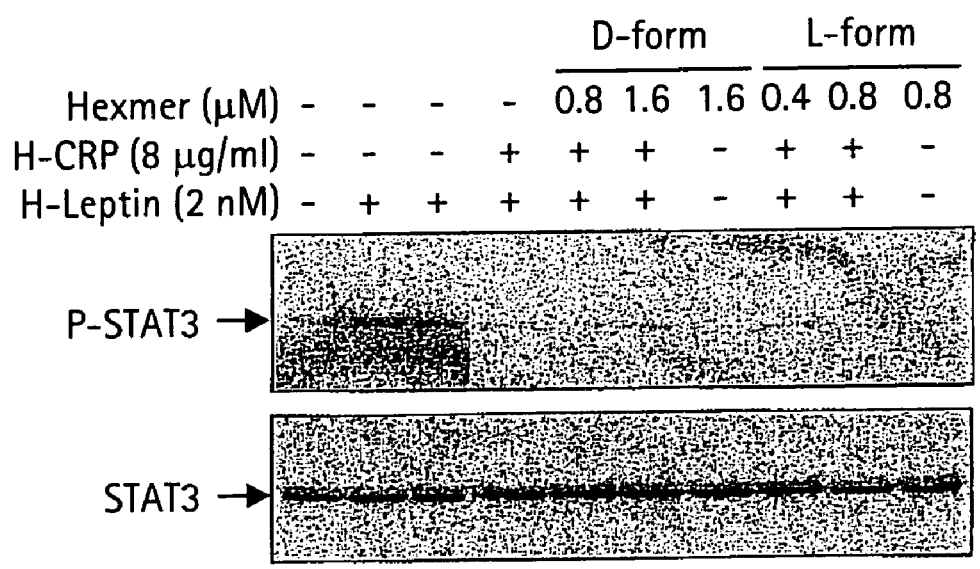
Figure 13B:
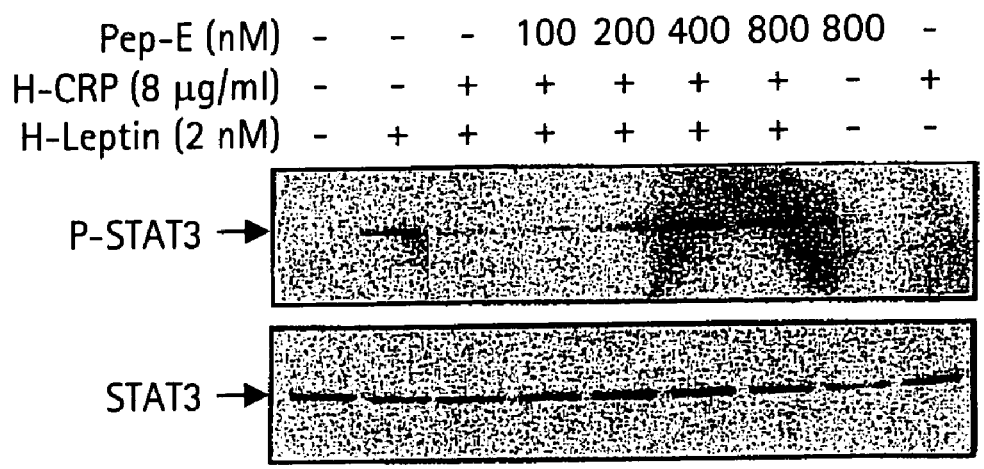

FIG. 13. (A&B): Western blot analysis of STAT3 activation measured by the degree of its tyrosine phosphorylation. As shown previously, co-incubation of human CRP with human leptin caused the reduction of leptin-stimulated STAT3 activation. However, the "hex-peptides" (L-form, $NH_2$—S—C—H—L—P—W—COOH (SEQ ID NO:3); D-form, $NH_2$—W—P—L—H—C—S—COOH (SEQ ID NO:5)) reported by Grasso, et al., when pre-incubated with human CRP and human leptin, failed to restore leptin-stimulated STAT3 activation. (A). In the same set of experiment, co-incubation of Peptide E polypeptide (SEQ ID NO:2) with human CRP was able to block the inhibitory effect of human CRP on leptin signaling. (B) Peptide-E (SEQ ID NO:2), by itself, did not induce any changes in STAT phosphorylation.

DETAILED DESCRIPTION OF THE INVENTION

It has been discovered that leptin interacts with factors in mammalian blood. Five (5) such factors, called Serum Leptin Interacting Proteins (SLIPs), have been identified. The interaction gives rise to a leptin-SLIP complex. Formation of the leptin-SLIP complex induces leptin resistance. Disruption or prevention of the complex is an effective therapeutic tool for reversing or preventing obesity. Likewise, formation of a modified complex is an effective therapeutic tool for reversing or preventing obesity.

On further characterization, SLIP-1 was found to be CRP. It was also found that the CRP-leptin complex impedes leptin signaling and attenuates its physiological effects.

Further, it was found that leptin (SEQ ID NO:4) stimulates expression of CRP in human primary hepatocytes in vitro. Injection of leptin in lean and healthy humans leads to elevation of plasma CRP concentrations. Thus, research shows that CRP is not merely a marker for obesity-related co-morbidities; rather, CRP is involved in the regulation of adiposity through interaction with leptin and induction of leptin resistance.

Both human and rat CRP directly bind to leptin and inhibit leptin's ability to activate STAT3 and PI3-kinase, two critical signaling pathways required for the satiety and weight-reducing effects of leptin. Human CRP, in a dose-dependent manner, attenuates the effects of human leptin on food-intake, body weight, glucose- and lipid metabolism in the leptin-deficient ob/ob mice. (Mice that are ob/ob are genetically obese. See Yang, et al., 1994, *Nature,* 372, 425.) The physiological roles of CRP in energy balance are clearly dependent on the presence of leptin, because CRP alone does not influence food-intake and body-weight in the ob/ob mice.

The identification of CRP as one of the major SLIPs is remarkable in several aspects. CRP is an important circulating factor that attenuates leptin sensitivity. CRP is an inflammatory marker and is generally, though not invariably, increased in obesity. M. Maachi et al., 2004, *Int. J. Obes. Relat. Metab. Disord.* 28, 993; T. Kazumi et al., 2003, *Metabolism* 52, 1113. Increase of CRP in obesity denotes inflammatory aspects as one of the metabolic complications of obesity, and is more closely linked to central patterns of fat deposition, including hepatic steatosis. Elevated CRP in obesity and related insulin resistance condition, such as type-2 diabetes, is predictive of risk for cardiovascular disease. M. B. Schulze et al., 2004, *Diabetes Care* 27, 889; P. M. Ridker, 2004, *American Heart Journal* 148, S19.

CRP abrogates leptin actions by binding leptin and interfering with leptin signal transduction, and thus contributes to the pathogenesis of obesity, or at least to a stubborn persistence of obesity by contributing to leptin resistance.

Although not wishing to be bound by any theory, it might be that CRP interacts with critical domains of leptin required for its binding to leptin receptors. Alternatively, the CRP-leptin complex might bind to leptin receptors but might be unable to stimulate intracellular signaling due to structural conformation changes.

The binary complex between leptin and CRP (or with SLIPs) impedes the flow of leptin into the central nervous system (CNS). CRP can cross the blood-brain barrier. G. Rajs et al., 2002, *Clin. Chem.* 48, 591. Thus, CRP might act within the CNS. Higher concentrations of CRP have been found in the cerebral-spinal fluid (CSF) of obese humans than in that of lean humans.

The role of CRP in leptin physiology is species-dependent. For example, mouse has very low serum CRP, and it varies little under immunological stimulation. However, mouse liver does express and secrete a pentraxin-like serum amyloid P (SAP) component structurally similar to CRP. J. Emsley et al., 1994, *Nature* 367, 338. It has been shown by immunoprecipitation that leptin binds to mouse SAP (FIG. 3B). It has also found that elevation of serum leptin concentrations through continuous infusion increased plasma concentrations of SAP in mice. Therefore, some species (such as mouse) use SAP rather than CRP as an attenuating factor of leptin functions.

Increased circulating leptin causes increased CRP production, which promotes CRP-leptin complex formation and diminished leptin activity. An embodiment provides means for disrupting CRP-leptin complex formation, thereby increasing free leptin both in the blood and in CSF. Increased quantities of circulating free leptin more effectively signal satiety, thereby reducing food intake and adiposity, and reversing associated conditions such as reduced fertility, inflammation, and coronary heart disease.

By monitoring CRP-leptin complex formation, clinicians can identify patients at risk of or suffering from leptin resistance, and thereby devise treatment regimens. As such, an embodiment provides a method for diagnosing CRP-induced obesity by measuring circulating levels of CRP in a mammal and comparing those levels with lean control. Elevated CRP levels indicate greater likelihood of CRP-leptin complex formation, diminished leptin activity, and corresponding weight gain over time. The measurement of circulating CRP can be made before, during, or after feeding. Identification of CRP-induced obesity will facilitate selection of effective therapies.

Any pharmacological intervention affecting the association between human CRP and leptin can be used to block the inhibitory effects of human CRP on leptin, and can lead to suppression of food-intake, reduction of body weight and adiposity, and alleviation of insulin resistance and diabetes. Such disruption of the CRP-leptin interaction can be achieved directly by chemicals or peptides interfering with the binding sites of the two proteins, or indirectly by causing conformational changes of either or both of CRP or leptin that lead to reduced binding or interaction between the two proteins.

Pharmacological intervention can also be employed to alter the interaction between human CRP and leptin to restore the effects of leptin in reducing plasma triglycerides and low-density lipid proteins (LDL), and will reduce the risk of atherosclerosis and cardiovascular disease.

Pharmacological intervention can also be employed to modify the stimulatory effects of leptin on CRP production, and can be exploited to decrease plasma CRP concentration with associated decrease CRP-leptin complex formation.

Likewise, pharmacological intervention can be exploited to alter the interaction between human CRP and leptin to increase transport of leptin into the central nervous system (CNS), and thus enhance leptin-induced effects in the CNS.

Pharmacological intervention can be achieved through the use of either conventional small molecule chemicals, peptides, or modified peptides. For present purposes, the term "peptides" includes proteins, partial proteins, polypeptides, and amino acid oligomers, any of which might further include modified amino acids.

Polypeptides excised from the full length leptin amino acid sequence can block the inhibitory effect of human CRP on human leptin. A series of polypeptides of average length of about 25-27 amino acids were chemically synthesized. FIG. 8A. In one embodiment, the polypeptide is that designated Peptide E (SEQ ID NO:2), as shown in FIG. 8B. Variations on Peptide E (SEQ ID NO:2) will also be useful in effecting such inhibition. For example, variations on the sequence of Peptide E (SEQ ID NO:2) having about 60% homology will likely impart a similar effect. The variation can be achieved by shifting a frame of 27 amino acids through the leptin sequence while retaining substantial homology with Peptide E (SEQ ID NO:2). By substantial homology is meant about 60% homology. In another embodiment, it means about 70% homology; in yet another, 80% homology, and in still another about 90% or 95% homology. The variation can also be achieved by shortening or lengthening the Peptide E sequence (SEQ ID NO:2) corresponding to the leptin amino acid sequence (SEQ ID NO:4) on either side of Peptide E (FIG. 11) while retaining substantial homology with Peptide E (SEQ ID NO:2). Thus, it is contemplated that polypeptides useful for inhibiting the effect of human CRP on human leptin can be selected from polypeptides having from about 16 aa to about 44 aa and substantial homology with Peptide E (SEQ ID NO:2).

Polypeptides having substantial homology with Peptide E (SEQ ID NO:2) are also referred to herein as "Peptide E analogues." Peptide E analogues also include those having substantial homology with Peptide E (SEQ ID NO:2) but wherein amino acids are substituted, added, or deleted in a manner inconsistent with the full length leptin amino acid sequence.

While not wishing to be bound by any theory, it is quite possible that Peptide E (SEQ ID NO:2) and polypeptides having substantial homology with it act as competitive antagonists for a leptin-binding site on CRP. For this reason, these polypeptides are also referred to as leptin-CRP antagonists.

Peptide E (SEQ ID NO:2) and analogues having substantial homology with it can also be PEGylated. PEGylation refers generally to the derivatization of molecules, polypeptides and the like by covalently binding one or more molecules of polyethylene glycol (PEG). In various media, particularly aqueous media, the long, chain-like PEG molecule is hydrated and in rapid motion. The motion of the PEG substituent sweeps out a large volume and prevents the approach and interference of other molecules. The PEG polymer chain can protect the molecule from immune responses and other clearance mechanisms, thereby prolonging and preserving bioavailability of the molecule.

Similarly, biological absorption, distribution, and clearance can be modified by altering the size, weight, shape, and linkage used to connect the PEG strand to the molecule in question. See, e.g. Roberts M. J. et al., 2002, *Advanced Drug Delivery Reviews,* 459-476, which is incorporated herein by reference.

In one embodiment, a PEG molecule is covalently attached to a leptin-CRP antagonist. The PEG molecule can be those of a molecular weight exceeding 1 kDa. In other embodiments, the PEG molecule is of a molecular weight exceeding 20 kDa.

In a further embodiment, pharmacological intervention by administration of Peptide E (SEQ ID NO:2) or an analogue having substantial homology thereof is described. The Peptide E (SEQ ID NO:2) or analogue can be PEGylated. As such, an embodiment provides a pharmaceutical formulation for reducing or preventing obesity in a patient suffering from or at risk of obesity comprising Peptide E and/or an analogue thereof and having substantial homology with it, and a pharmaceutically acceptable excipient. The pharmaceutical formulation can be compounded for parenteral, oral, transdermal, topical, buccal, sublingual, inhalation, rectal or vaginal administration.

Similarly, Peptide E (SEQ ID NO:2), analogues thereof, and PEGylated derivatives of Peptide E and its analogues, can be used to treat various disorders associated with obesity such as inflammation, atherosclerosis, diminished fertility, and defective or anomalous glucose and/or lipid metabolism.

A further embodiment provides a method for reducing or preventing obesity in a patient suffering from or at risk of obesity, said method comprising administering to said patient an obesity-reducing or -preventing amount of Peptide E (SEQ ID NO:2) or an analogue thereof. The patient can be a mammal, and, in particular, a human.

Another embodiment provides methods for diagnosing patients suffering from CRP-induced obesity. CRP-induced obesity means obesity caused, at least in part, by reduced leptin activity as a result of leptin binding to CRP. Reduced leptin activity refers to a diminishment in the effect of leptin in signaling satiety, and/or suppressing food intake, and/or reducing adiposity. Reduced leptin activity might be caused by interaction with other endogenous factors such as CRP, or corresponding factors in other species, such as SAP in mice. Leptin activity is not to be confused with leptin concentration as our studies have shown that in many forms of obesity there is an inverse relationship between the two.

Another embodiment provides an assay for drugs useful in the prophylaxis or treatment of CRP-induced obesity. For example, one can exploit the relationship between CRP and leptin to screen for CRP antagonists. For purposes of this disclosure, the term "CRP antagonist" means an agent that interferes with CRP-leptin complex formation or diminishes leptin-induced production of CRP. By diminishing the incidence of CRP-leptin complex formation, free leptin concentration is increased. As there is a correlation between free leptin and leptin activity, a reduction in CRP/leptin complex formation will sustain leptin activity and signaling. CRP antagonists that increase circulating free leptin will thus be useful for preventing or treating CRP-induced obesity.

Agents can be screened for CRP antagonism by various means. The screening can be performed by simultaneously or sequentially incubating leptin with a potential CRP antagonist and CRP. This might be performed by pre-loading a leptin affinity column with CRP and subsequently a potential CRP antagonist, and identifying those that interact with leptin in such a way that they preclude or diminish CRP-leptin complex formation. Putative antagonists increase the amount of CRP washed through the column compared to an equivalent run in the absence of the putative antagonist.

Alternatively, potential antagonists could be identified based on interaction with CRP to inhibit or preclude CRP-leptin complex formation. This might involve first contacting CRP and the potential antagonist, removing residual free (unbound) potential antagonist, contacting the resulting CRP with leptin (SEQ ID NO:4), measuring CRP-leptin complex formation, and comparing that value with CRP leptin complex formation in the absence of the potential antagonist.

CRP antagonists can be identified by screening for compounds that inhibit the signaling capabilities of leptin in cultured cells. For example, a potential CRP antagonist can be co-incubated with leptin and CRP before the mixture is incubated with the cultured cells containing leptin receptors. Subsequently, leptin-induced activity of STAT3 and PI3-kinase can be assayed as described above. The results should be compared to those obtained in the absence of the potential antagonist. A CRP antagonist should revitalize the ability of leptin (SEQ ID NO:4) to signal in the cultured cells.

CRP antagonists can also be identified as depicted in FIG. 3F. Radio-labelled leptin can be pre-mixed with CRP and a potential antagonist, and testing is used to determine if binding of leptin to a cell surface can be restored.

CRP antagonists can be identified by screening for compounds that interfere with the promotion of CRP production. For example, an agent can be screened as a potential antagonist by introducing it into a'system where leptin would otherwise stimulate the production of CRP, and measuring the CRP produced. Comparison with CRP production in the absence of the potential antagonist reveals its potential as an antagonist. The system might be an in vitro system or an in vivo system as in an animal model, particularly since it is believed that in vitro data on efficacy of Peptide E polypeptides and related polypeptides is reasonably predictive of in vivo efficacy. Where non-human animal models are used, species-specific CRP analogues might be monitored. For example, in the mouse animal model, CRP antagonists might be screened by monitoring leptin-induced production of pentraxin-like serum amyloid P (SAP), which is structurally similar to CRP and may perform the function in mouse that CRP performs in human.

Another embodiment provides a method of treating a mammal, particularly a human, suffering CRP-induced obesity. The method involves administering a CRP antagonist to such patient in an amount effective to diminish the endogenous production of CRP in such mammal (human).

Yet another embodiment provides a screening assay for CRP agonists. For purposes of this disclosure, the term "CRP agonist" refers to agents that mimic CRP in its ability to diminish free leptin and/or leptin's ability to signal satiety. Certain disease states (e.g., cancer) are associated with decreased food intake, which compromises the overall health and strength of the patient. The administration of drugs that mimic CRP's ability to modify leptin's signaling capabilities can be used to alter appetite and increase a patient's food intake.

CRP agonists can also be identified by comparative binding studies. For example, the potential agonist might be exposed to leptin, and the resulting mixture monitored for rate and durability of agonist-leptin complex formation as compared to CRP. Yet another embodiment provides means for identifying agents that compete with CRP for leptin binding and/or mimic CRP's ability to alter leptin's ability to signal satiety. Thus, another embodiment provides a screen for CRP agonists comprising forming a mixture including a potential CRP agonist and leptin, monitoring and/or measuring agonist-leptin complex formation, and comparing the attributes of the resulting complex with CRP-leptin complex. The attributes monitored or measured can include rate of complex formation, durability of the complex, and the effect of the complex on leptin's signaling capacity.

A further embodiment affords a means for identifying leptin agonists. For purposes of this disclosure, the term "leptin agonist" means agents that stimulate endogenous CRP production, thereby enhancing leptin-CRP complex formation, diminishing free leptin (SEQ ID NO:4), and reducing the ability of leptin (SEQ ID NO:4) to signal satiety. Such agents can be identified by introducing potential leptin agonists to a system that is capable of producing CRP and responds to leptin by increasing that production of CRP. Putative leptin agonists can be identified by introducing agents of interest to such a system and screening for agents that stimulate CRP production. Another embodiment provides a means for treating a mammal, particularly a human, suffering from wasting due to insufficient nutritional intake comprising administering to such patient a leptin agonist.

Agents useful as CRP antagonists, CRP agonists, and leptin agonists will be selected from peptides, amino acid oligomers, and small molecules.

EXAMPLES

1. Purification & Identification of serum leptin-interacting proteins (SLIPs): Mouse and human recombinant leptin was covalently linked to the Sepharose-beads with an Amino-Link kit (Pierce Biotechnology, Rockford, Ill.). Rat or human serum (1.5 ml) was loaded onto the affinity column which was then washed with 10-volumes of PBS-0.5% Tween-20. The bound material after the wash was eluted with an acidic glycine solution, and the eluate was immediately neutralized in a Tris-buffer (50 mM, pH=9.5).

2. Signaling Studies: A HEK293 cell line stably expressing the human long-form receptor, OB-Rb (M. Friedman-Einat et al., 2003, *Regul. Pept.* 111, 77) was serum starved for 2-h before addition of leptin and CRP. Leptin (SEQ ID NO:4), in the presence or absence of C-reactive proteins, was pre-incubated in μ-MEM for 30 minutes at 37° C. before applied to the cells. After a 30-incubation with leptin (SEQ ID NO:4), the cells were harvested in a previously described protein lysis buffer. A. Z. Zhao et al., 1997, *Proc. Natl. Acad. Sci. U.S.A.* 94, 322. The protein extract was subjected to a western blot assay with an anti-phospho-STAT3 specific antibody (Cell Signaling, Beverly, Mass.). For studies involving the primary hypothalamic neurons, the rat hypothalamus was surgically isolated right after euthanasia, and immediately placed in the DMEM for incubation with leptin in the presence or absence of CRP.

3(a). In vivo assessment of CRP functions: The micro-osmotic pumps (#1007D, DURECT, Cupertino, Calif.) were subcutaneously imbedded in the ob/ob or wild-type mice according to the instructions of the manufacturer. The osmotic pumps were pre-filled with saline, CRP, leptin or leptin plus CRP. Food-intake (24-h), body weight, and body temperature were monitored daily post-surgery. Blood glucose concentrations were measured from the tail-vein blood samples right before and at the end of infusion with a Precision Plus glucose meter (Medisense, Abbot Park, Ill.).

3(b) Assessment of serum leptin insulin, and CRP: Human- and mouse-leptin concentrations were measured with the ELISA kit from CHEMICON (Temecular, Calif.) and R&D Systems (Minneapolis, Minn.), respectively, according to the instructions of the manufacturer. Serum mouse insulin concentrations were determined with an ELISA assay (LINCO Research, St. Charles, Mo.). Human CRP concentrations were also evaluated with an ELISA kit (Alpha Diagnostics International, San Antonio, Tex.).

3(c) Measurement of serum- and tissue-triglycerides: Serum- and tissue-triglycerides were determined with the protocols described in J. N. Huan et al., 2003, *J. Biol. Chem.* 278, 45638.

4. Measurement of $IC_{50}$ for human CRP against human leptin: Human leptin was iodinated with $Na^{125}I$ using the Iodogen method. Briefly, 15 μg of human leptin in 100 mM Phosphate buffer pH 7.5 were incubated with 1 mCi of carrier-free $Na^{125}I$ (2200 Ci/mmol) in a glass tube containing 50 μg Iodogen. After 10 minute incubation at room temperature, the reaction was stopped with 100 μl 0.1% trifluoroacetic acid (TFA). The reaction mixture was immediately purified by reverse-phase HPLC. The separation employed a 5 minute isocratic step at 20% eluant B in A, followed by two consecutive 30 minute linear gradients from 20 to 50%, then from 50 to 60% eluant B in A (where eluant A is water containing 0.1% TFA and eluant B is acetonitrile containing 0.1% TFA) at a flow rate of 1.5 ml/min. The $^{125}I$-labeled leptin (~2 ng/ml) was pre-incubated with various concentrations of human CRP in 1 ml of μ-MEM for 30 minute before added to the OBR-expressing HEK293 cells. The incubation would last for 3 hours at 4° C. before the media was aspirated and the cells were dissolved in 0.1N NaOH for scintillation counting.

Figure 1A:
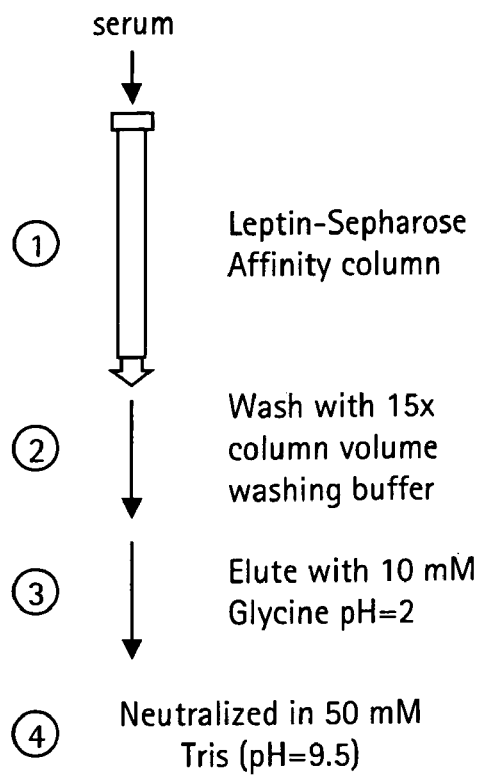
FIG. 1(A): The scheme for purification of SLIPs through a leptin-affinity column. Human or rat serum (1.5 ml each) was passed through the leptin-conjugated sepharose column. After an extensive wash with 1×PBS-0.5% Tween-20 (for rat serum samples) or a $Ca^{2+}$ containing buffer (0.1M Tris-Cl, 0.1M NaCl, 2 mM $CaCl_2$) (for human serum samples), the bound proteins were eluted with acidic glycine solution. FIG.
Figure 1B:
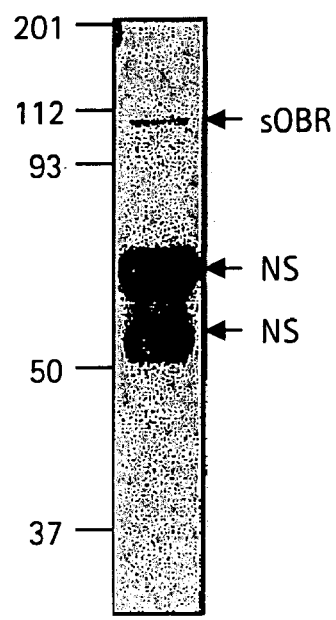
FIG. 1. Purification of serum leptin interacting proteins (SLIPs)

To identify the potential serum leptin interacting proteins (SLIPs), human and rat sera was loaded onto affinity columns in which the human and mouse recombinant leptin peptides, respectively, were covalently linked to the sepharose beads. After an extensive wash with phosphate-buffered saline containing 0.5% Tween-20 and the final elution with an acidic glycine solution (FIG. 1A), five major protein species were found to remain bound to the human leptin column with apparent molecular weights on silver-stained SDS-gel of ~30, 42, ~65, ~70, and ~85 Kd (FIG. 1B). These five protein species have been termed "serum leptin interacting protein" (SLIP)-1, 2, 3, 4, and 5, respectively. A substantial amount of human leptin was also identified in these eluates through a western blot assay, and is indicated by the dash arrow in FIG. 1B. This is likely due to the association of serum leptin with SLIPs.

Figure 1C:
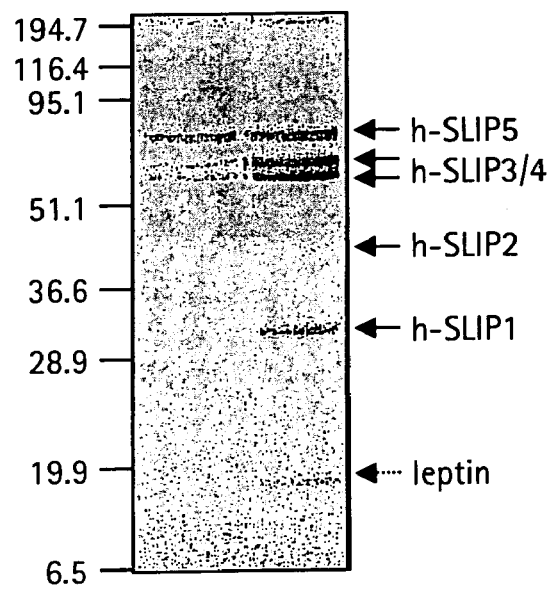
Figure 1D:
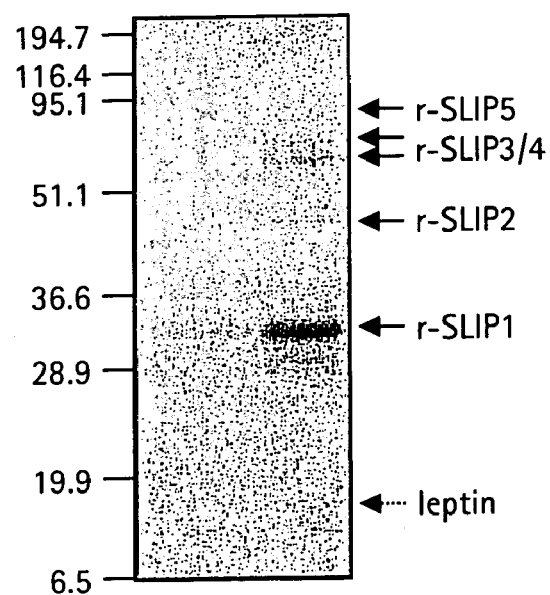

All five human SLIPs have counterparts in rat serum. The five eluted major proteins after rat serum passing through the mouse leptin-affinity column are very similar in molecular weight to those of human SLIPs (FIG. 1C). The soluble leptin receptor (sOBR) does not appear to account for a major component of leptin binding relative to the five SLIPs. Western blot assay also did not reveal any detectable amount of sOBR in the eluates.

Rat SLIP-1 was excised from a SDS-gel and subjected to a MALDI-TOF assay following a tryptic digestion. Such proteomic analysis assigned rat SLIP-1 exclusively as rat C-reactive protein (CRP) (FIG. 2).

Figure 2C:
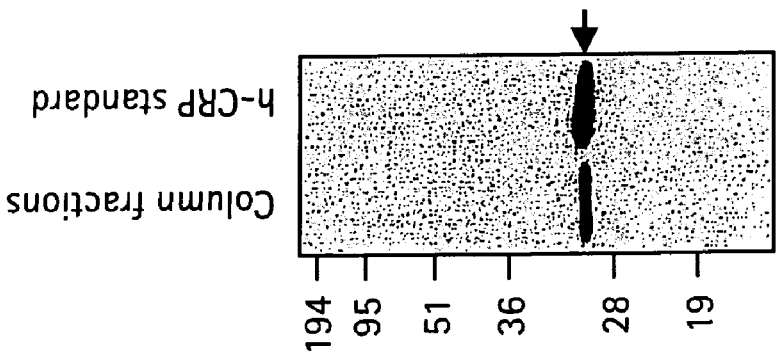

Western blot assays were performed using polyclonal antibodies that specifically recognize human CRP and rat CRP. H-SLIP-1 and r-SLIP-1, but not other SLIPs, reacted with the human- and rat-CRP antibody, respectively, further supporting the identity of SLIP-1 as the C-reactive protein. (FIGS. 2B & 2C).

Direct binding of Ck and leptin in an immunoprecipitation assay was determined. Rat CRP was purified from fresh rat serum to >95% employing a previously established affinity-purification protocol. J. Tseng et al., 1988, *Mol. Immunol.* 25, 679. This purity is very similar to the human CRP preparation obtained from a commercial source (CHEMICON International). The purified human- and rat-CRP proteins were pre-mixed with recombinant human and mouse leptin, respectively, before addition of specific antibodies against human- and mouse-leptin. The concentrations of CRP and leptin in the precipitation reaction were all within the physiological ranges (M. B. Schulze et al., 2004, *Diabetes Care* 27, 889; T. Kazumi et al., 2003, *Metabolism* 52, 1113).

In parallel experiments, recombinant leptin was also pre-mixed with human- or rat serum to allow for potential direct interactions prior to immunoprecipitation. The precipitation pellets obtained were subjected to western blot assays with specific anti-CRP antibodies. As shown in FIG. 3A, precipitation of human leptin could pull down human CRP from both the leptin/CRP mixture and from human serum. Similarly, immunoprecipitation of mouse leptin could also bring down rat CRP from the leptin and CRP mixture as well as from rat serum (FIG. 3B). The direct interaction of CRP and leptin was further illustrated in FIGS. 3C and 3D, in which immunoprecipitation of rat and human CRP was found to pull down leptin proteins. These data indicated a direct interaction between C-reaction protein and leptin. Because of the similarities between rat CRP and human CRP in the binding to leptin and of our main interest in the relevance to human obesity, focus was placed on potential functional effects of human CRP in the subsequent experiments.

To examine if human CRP interferes with the binding of human leptin to its receptors, we used a HEK293 cell line stably transfected with the long-form human leptin receptor, OB-Rb. The characterization of this cell line has been reported in earlier studies. M. Friedman-Einat et al., 2003, Regul. Pept. 111, 77. We found that the $K_d$ for leptin and its receptors in this cell line was $1.0 \times 10^{-9}$ M, which was consistent with prior reports. P. Mistrik et al., 2004, Anal. Biochem. 327, 271. Pre-incubation of human CRP with $^{125}$I-labeled human leptin reduced leptin's binding to its receptors in a dose-dependent manner (FIG. 3E). The value of $IC_{50}$ was approximately 80 ng/ml of CRP (in the presence of ~2 ng/ml leptin).

Figure 4A:
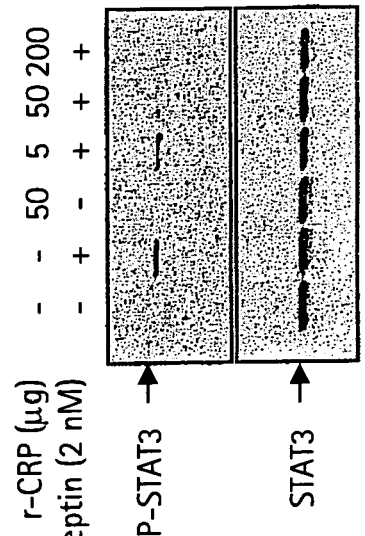
Figure 4B:
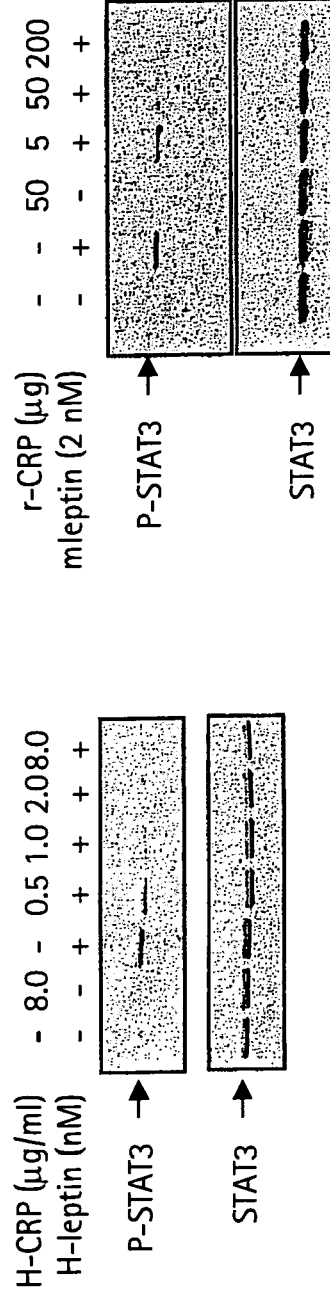

To determine if the interaction between CRP and leptin influences cellular actions of leptin, we assessed the ability of leptin to stimulate tyrosine phosphorylation of STAT3 and PI3-kinase activity in the presence of CRP in vitro. In the HEK293 cell line overexpressing OB-Rb, both human CRP and rat CRP were found to attenuate the tyrosine-phosphorylation of STAT3 induced by 2 nM of human- or murine-leptin, respectively (FIG. 4A & 4B). The concentrations of human CRP and rat CRP required to block leptin-induced STAT3 phosphorylation are well within the ranges observed in human and rat plasma (M. B. Schulze et al., 2004, Diabetes Care 27, 889; D. Aronson et al., 2004, Int. J. Obes. Relat. Metab. Disord. 28, 674; F. C. de Beer et al., 1982, Immunology 45, 55, although higher concentrations of rat- than human-CRP are required to achieve the equivalent effects (FIG. 4B).

Figure 4C:
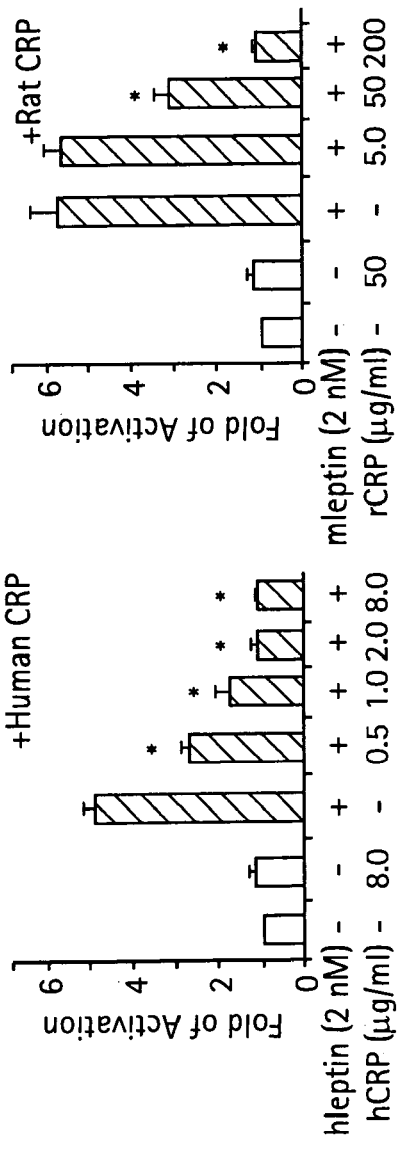

In a specificity control, exertion of negative influence on leptin signaling (similar to CRP) was assessed for other protein. Human serum albumin was tested, but even at concentrations of several hundred-fold higher than the human CRP, no appreciable effect on leptin-induced STAT3 phosphorylation was observed (FIG. 4C).

Figure 4D:
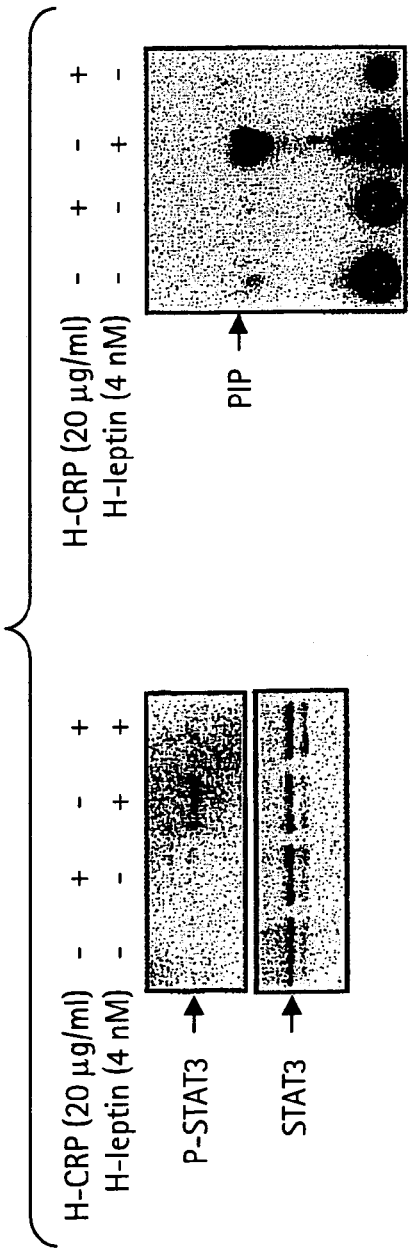
Figure 4E:
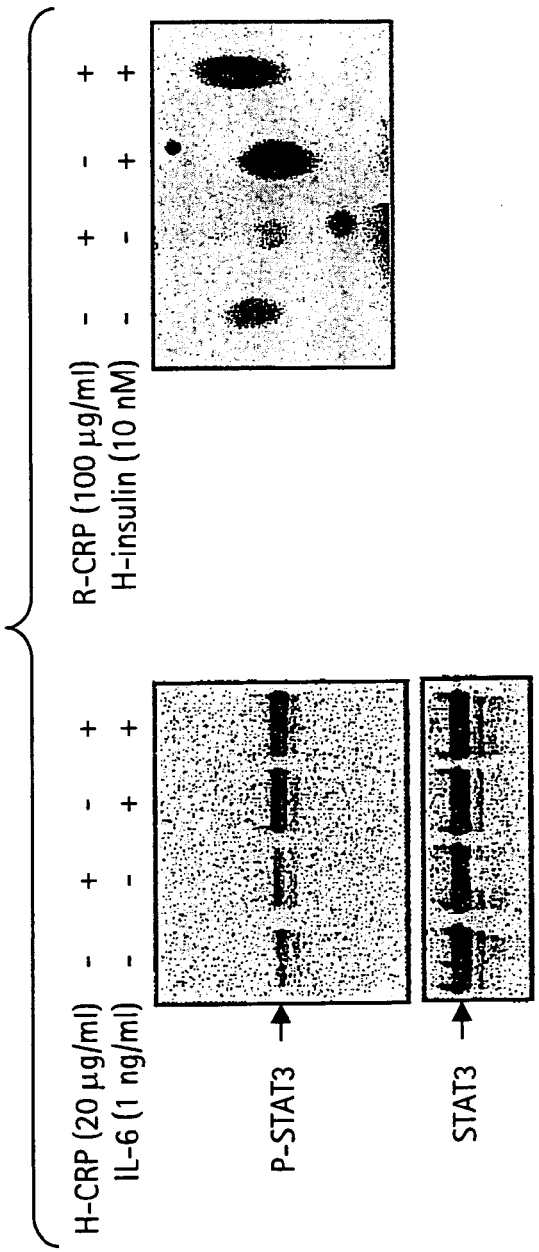

Previous studies have reported a requirement of both JAK-STAT and PI3-kinase pathways in mediating leptin signaling within the hypothalamus. C. Vaisse et al., 1996, Nat. Genet. 14, 95; A. Z. Zhao et al., 2002, Nat. Neurosci. 5, 727; K. D. Niswender et al., 2001, Nature 413, 794. The effects of human CRP on leptin signaling in rat primary hypothalamic explants were also tested (FIG. 4D). In phospho-STAT3 and PI3-kinase assays, human CRP inhibited leptin signaling in primary hypothalamic neurons (FIG. 4D). It is unlikely that the inhibitory effect of CRP on leptin signaling is due to non-specific toxicity because the equivalent human CRP did not suppress IL-6 induced activation of STAT3 in human or insulin-stimulated PI3-kinase activity in 3T3-L1 adipocytes (FIG. 4E).

Because of the negative influence of CRP on leptin signaling, we postulated that elevation of circulating CRP through continuous infusion would attenuate the effects of leptin to suppress food-intake and reduce weight. Due to the high basal plasma concentrations of CRP, rats are not an ideal model system to test this hypothesis. However, mice have only negligible plasma levels of C-reactive protein (K. Zahedi et al., 1991, Inflammation 15, 1, and accordingly, were used to examine the effects of exogenous human CRP upon leptin given to ob/ob mice. Differing amounts of human CRP, either alone or with human leptin were administered through micro-osmotic pumps to 8-week old ob/ob mice (FIG. 6A-6D).

Figure 5A:
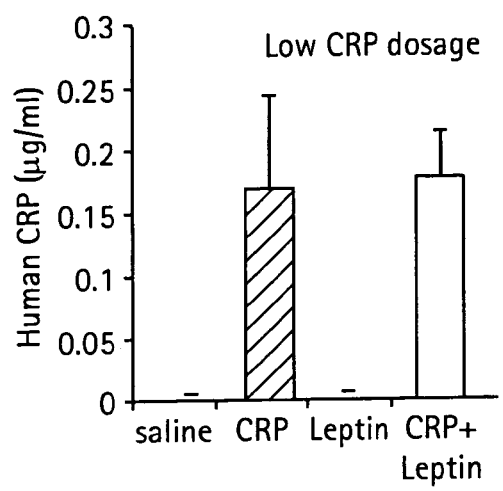
Figure 5B:
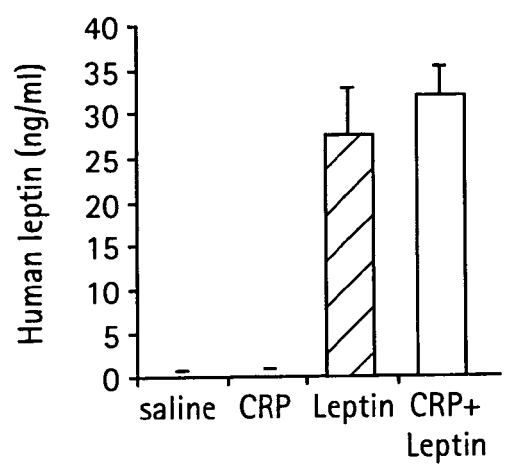

During the 6-day continuous infusion period, human leptin produced the expected reduction in food-intake and body weight in the ob/ob mice (FIG. 6A-6D). Although co-infusion of human CRP at a low infusion dosage (10 µg/day; FIG. 5A) only partially attenuated these effects of human leptin (FIG. 6A & 6B), at a higher concentration (FIG. 5C), human CRP completely blocked the actions of leptin to restrain appetite and induce weight loss.

Figure 5C:
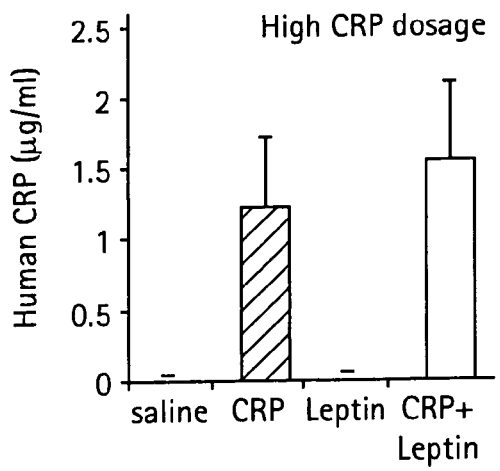
Figure 5D:
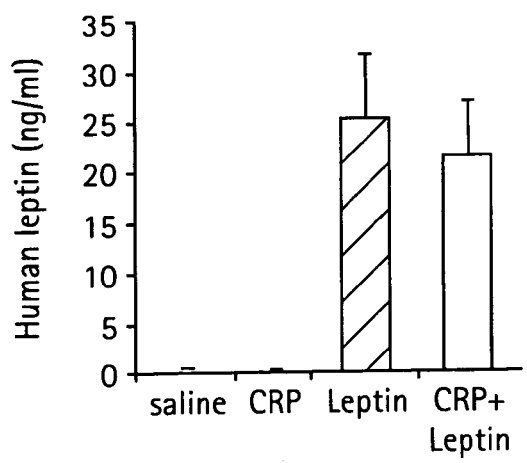
Figure 6A:
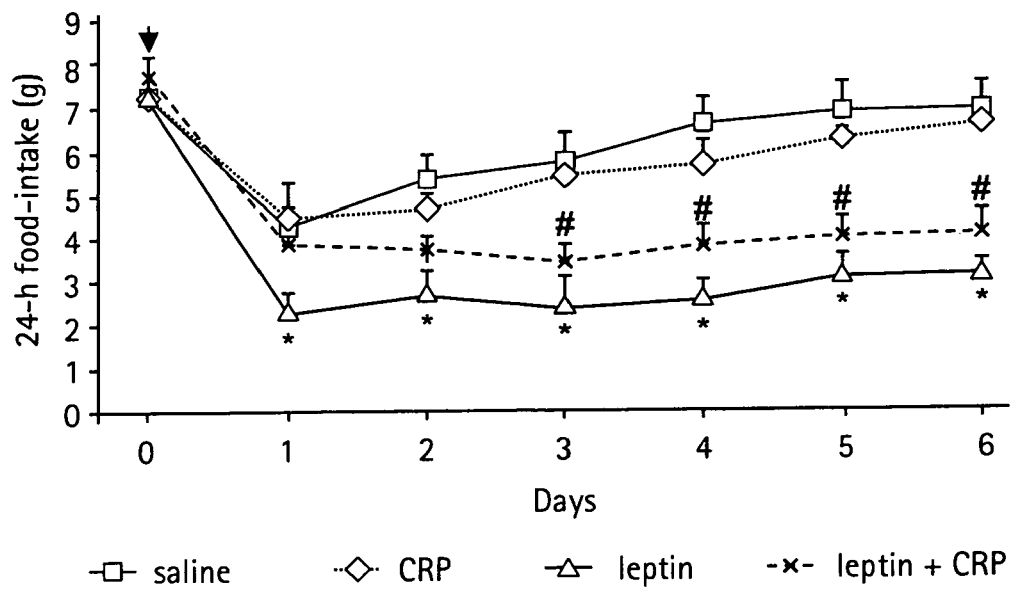
Figure 6B:
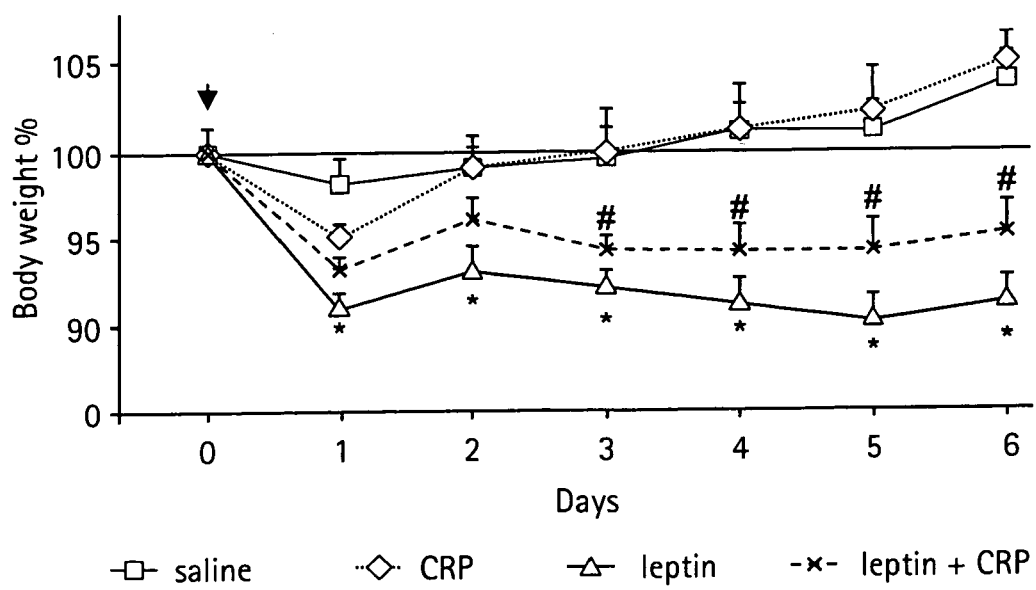
Figure 6C:
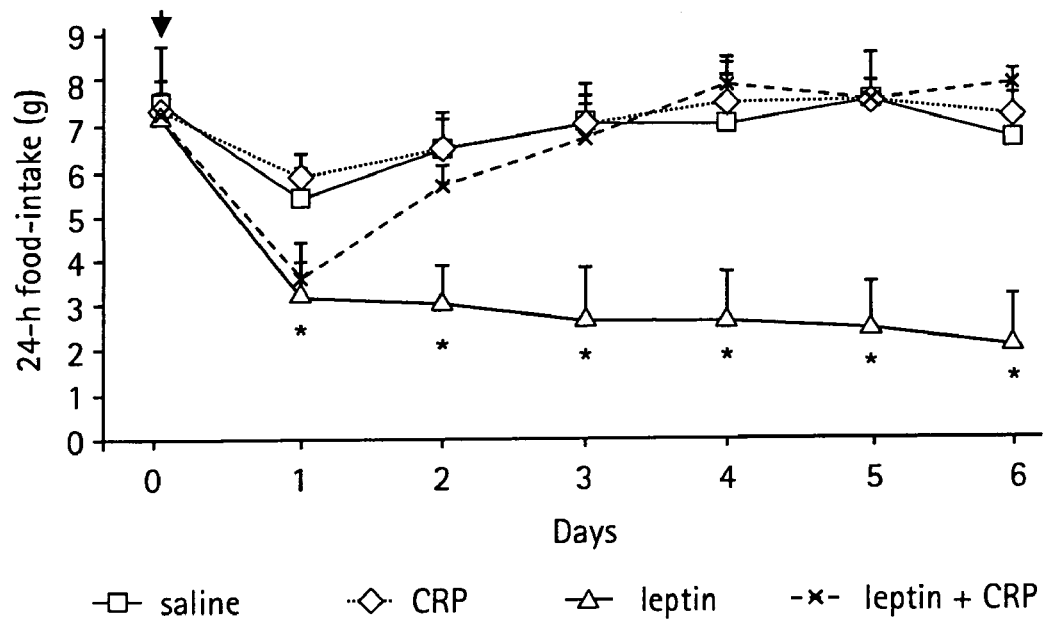
Figure 6D:
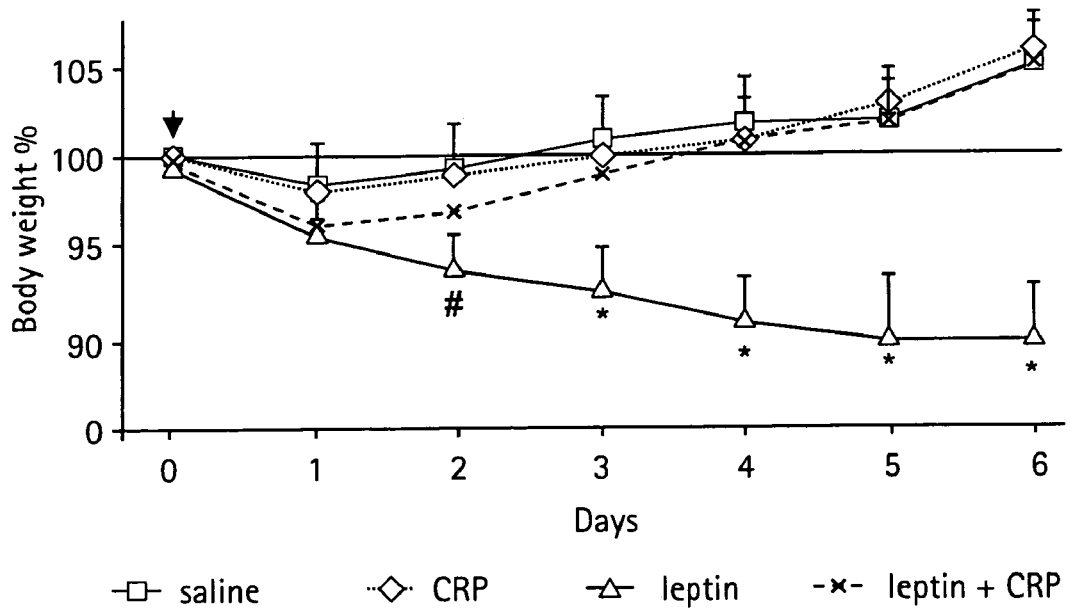
Figure 6E:
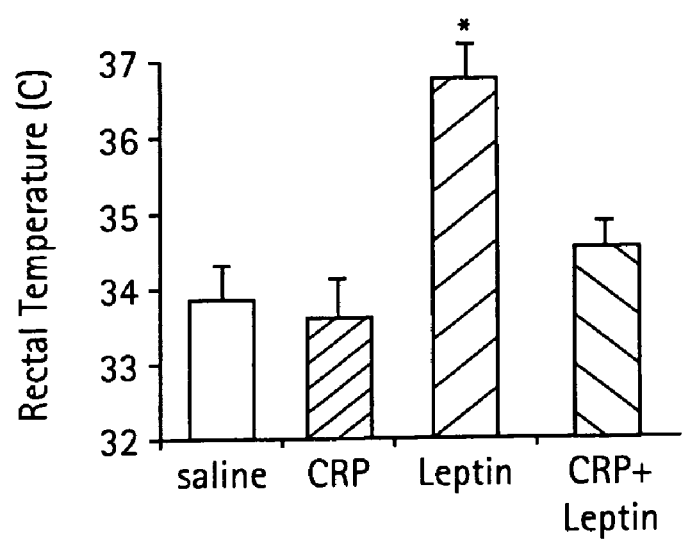

Consistent with these observations that administration of human CRP induced in vivo leptin resistance in ob/ob mice, there was also attenuation of leptin-induced energy expenditure, as was partially reflected in the recordings of body temperature (FIG. 6E). Importantly, the serum concentrations of human CRP attained in these mice are well within the physiological range observed in human plasma (FIG. 5A & 5C). M. Maachi et al., 2004, Int. J. Obes. Relat. Metab. Disord. 28, 993; M. B. Schulze et al., 2004, Diabetes Care 27, 889. Additionally, although leptin administration to ob/ob mice alleviated diabetes, including lowering of blood glucose, plasma insulin (FIG. 7A & 7B), and serum and hepatic triglyceride (FIG. 8C & 8D), co-infusion of human CRP blocked these effects of leptin (FIG. 7A-7D). As a further confirmation of the negative effects of CRP on leptin action, activation of STAT3 in the hypothalamic tissues of ob/ob mice was also blocked by co-infusion of CRP with leptin (FIG. 7E). It should be emphasized that administration of human CRP alone (without co-infusion of leptin) did not affect food-intake or body weight. Thus, the impact of CRP is dependent upon the presence of leptin (FIG. 6-7).

5. Peptide E Polypeptides and Related Polypeptides: It was observed that human C-reactive protein directly binds to human leptin and inhibits the physiological functions of human leptin both in vitro and in vivo.

To determine the domains that are relevant to the interaction between human leptin and human C-reactive protein, a series of polypeptides (average length of 25 amino acids) were chemically synthesized (FIG. 8A).

The Peptide-E polypeptide represents one of such peptides and its composition described in FIG. 8B and SEQ ID NO:2.

In the in vitro experiment, Peptide-E was pre-incubated with human CRP for 30 minutes before being mixed with human leptin for an additional 45 minutes. The resultant mixture was then added to the HEK-293 cells overexpressing the long form leptin receptors, OB-Rb (FIG. 9). After a 30 minute incubation, the cells were harvested in a protein extraction buffer (Zhao, et al., 1997, PNAS). The signaling of leptin in the cells, measured by its ability to stimulate tyrosine phosphorylation on STAT3 in a western blot assay, was evaluated.

Figure 10A:
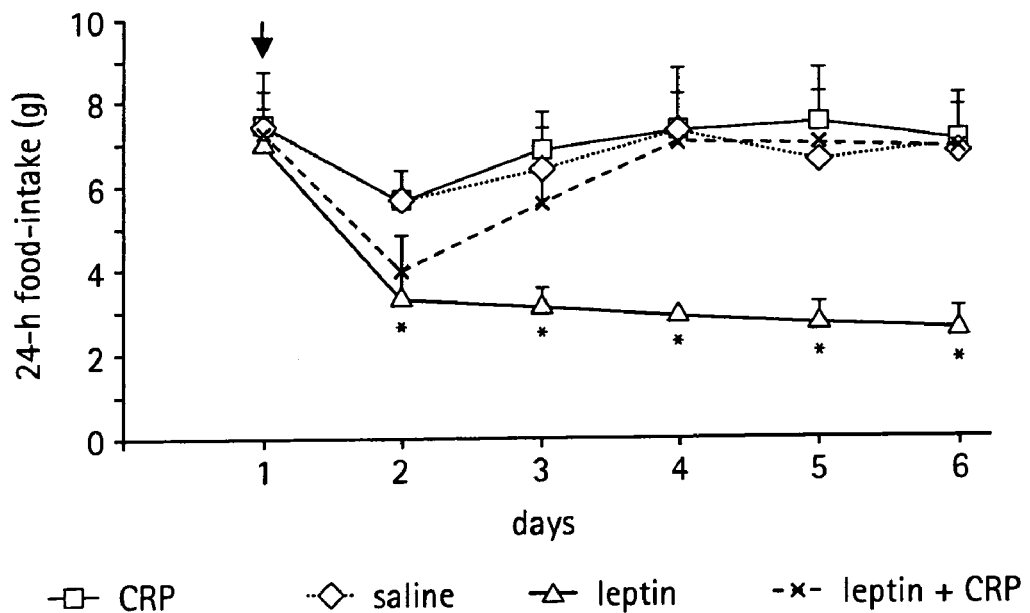
Figure 10B:
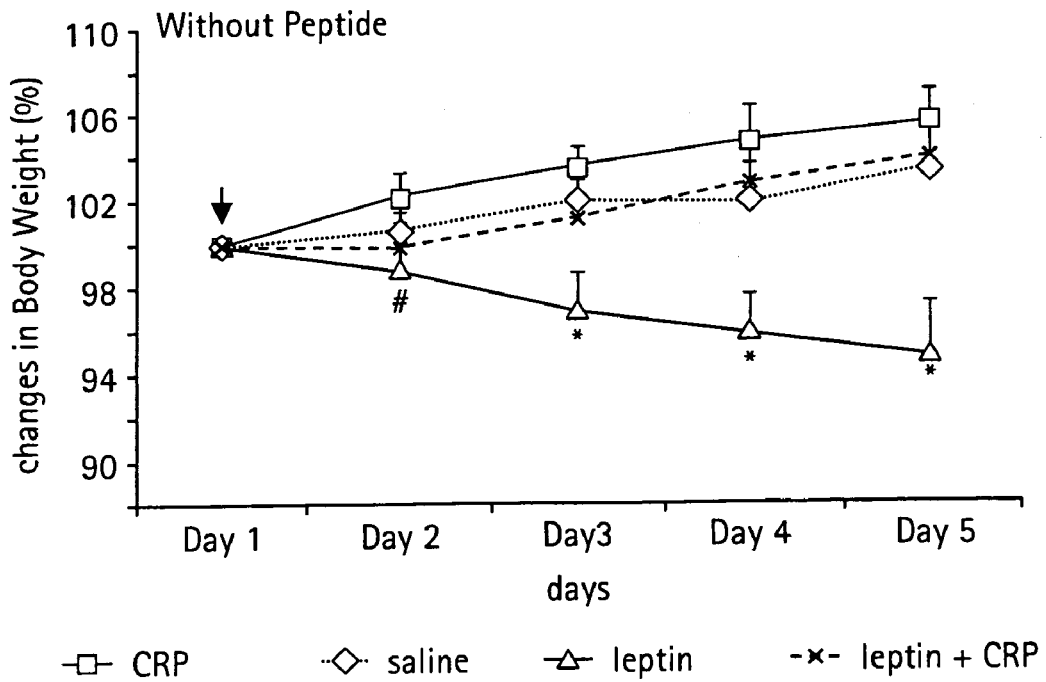
Figure 10C:
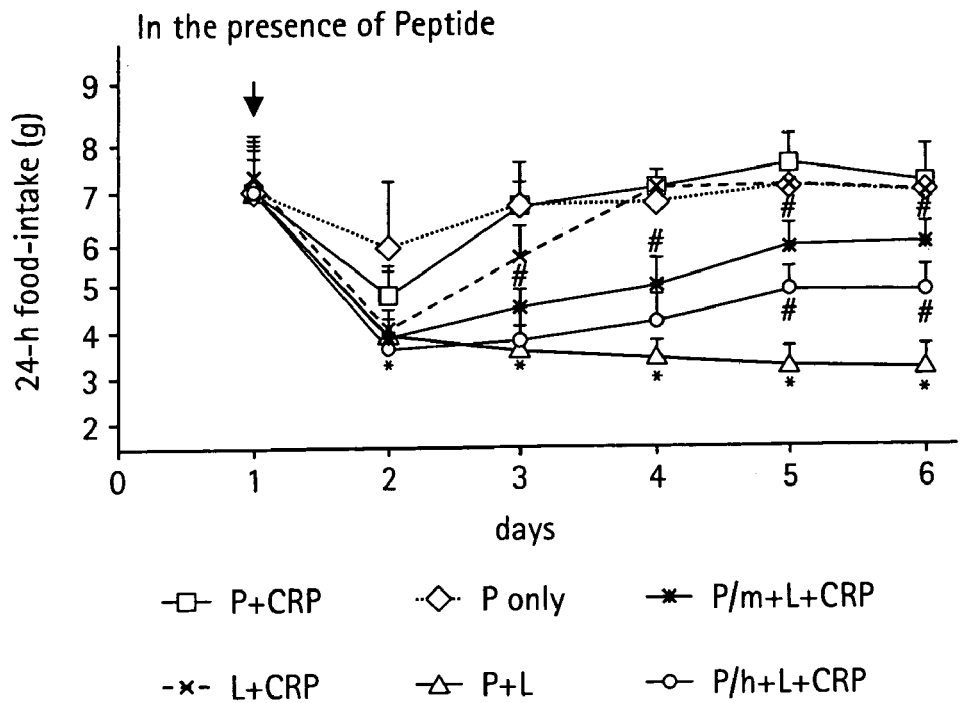
Figure 10D:
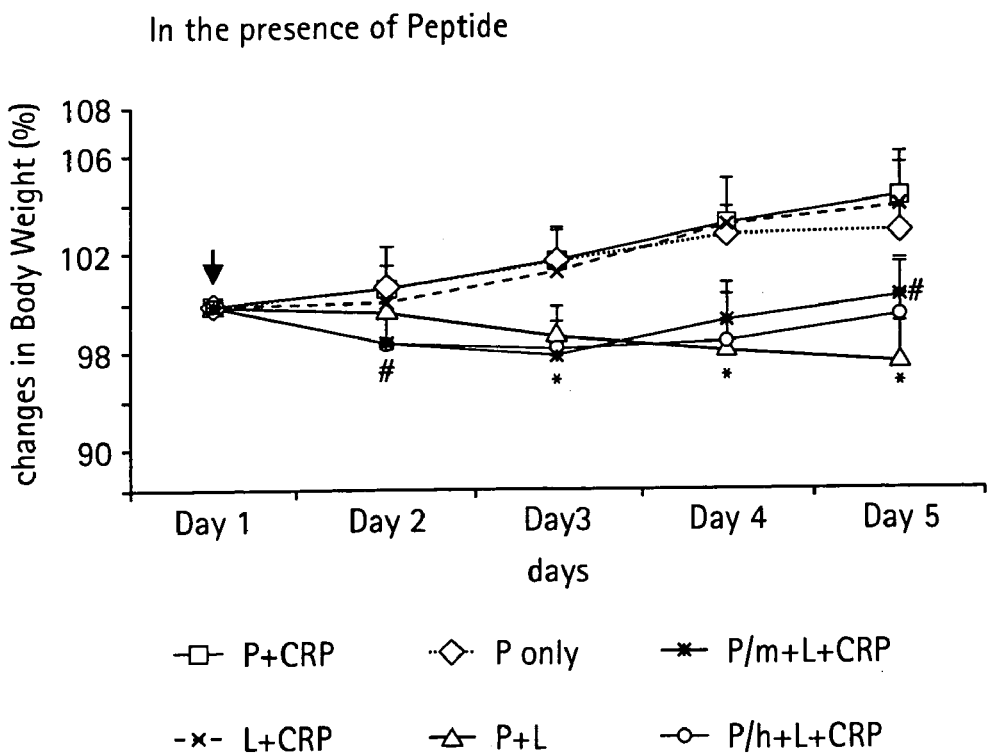
Figure 10E:
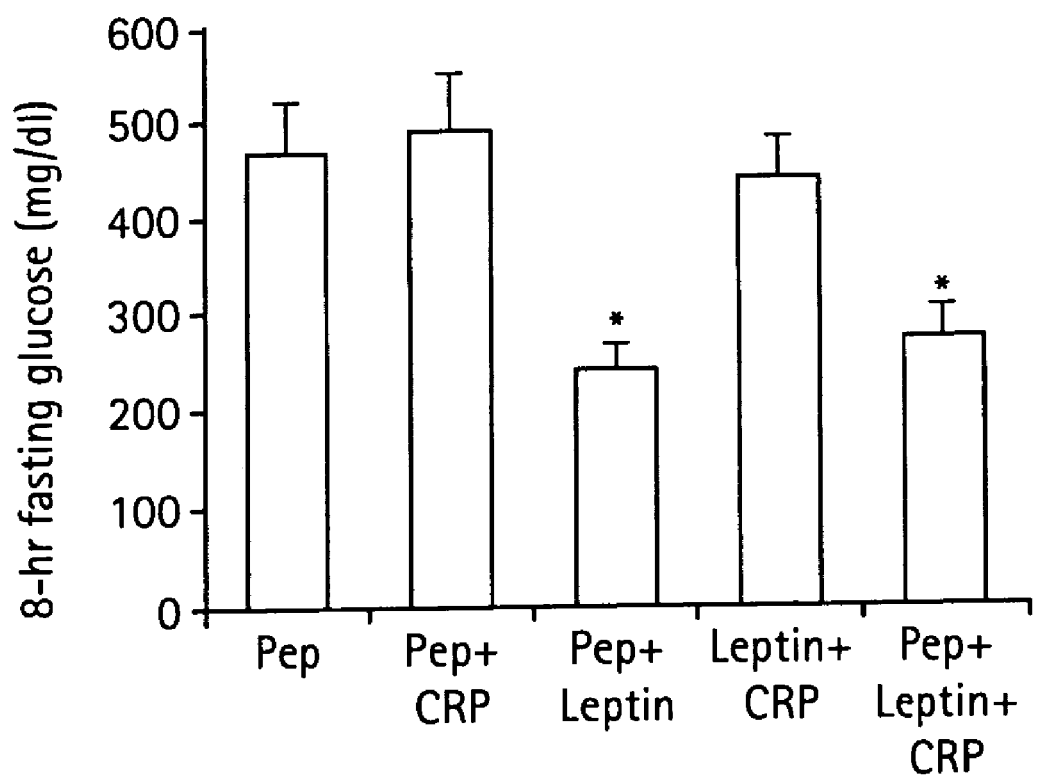

In the in vivo experiment, the Peptide E polypeptide was co-infused through mini-osmotic pumps with human CRP and leptin into the ob/ob mice. Food-intake (24 hours) and body weight were followed during the infusion period (FIG. 10A-10D). Although in the absence of the Peptide E (SEQ ID NO:2) polypeptide, human CRP was able to block the satiety and weight-reducing effects of human leptin as we have reported in our previous provisional patent filing (FIGS. 10A & 10B), co-fusion of Peptide E (SEQ ID NO:2) polypeptide with human CRP and leptin could restore both of these functions of human leptin (FIGS. 10C & 10D). At the end of infusion, it was found that Peptide E (SEQ ID NO:2) polypeptide could restore the beneficial effect of human leptin on blood glucose (FIG. 10E).

The synthetic peptide, Peptide E (SEQ ID NO:2) polypeptide and its related polypeptides, likely have the following functions:

a) To alleviate the inhibitory effects of human CRP on the physiological functions of human leptin.

b) To restore the physiological functions of human leptin with respect to suppression of food-intake, reduction of body weight and adiposity, and improvement of insulin sensitivity.

c) Because of the functions described in a) and b), Peptide-E and its analogues can be clinically used as an agent to treat obesity and type-2 diabetes.

d) Peptide E (SEQ ID NO:2) and its derivatives can also be used clinically to reduce the risk of developing atherosclerosis.

6. Comparison of Peptide E Polypeptide with the Hexamer of U.S. Pat. No. 6,777,388: U.S. Pat. No. 6,777,388 reports a 6 amino acid polypeptide having the sequence $NH_2$-S-C-H-L-P-W-COOH (SEQ ID NO:3). The polypeptide reported in the '388 patent is functionally different from the Peptide E (SEQ ID NO:2) polypeptide and its variants. The Peptide E (SEQ ID NO:2) polypeptide includes 27 amino acids representing a segment of human leptin polypeptide. The hexamer reported in the '388 patent corresponds with a portion of the Peptide-E sequences.

Using a design similar to the in vitro experiment described in Example 5, the hexamer of the '388 patent (SEQ ID NO:3) was pre-incubated with human CRP (8 μg/ml) and human leptin (2 nM) for 1-hour. The resultant mixture was then added to the HEK-293 cells overexpressing the long form leptin receptors, OB-Rb (FIG. 12). After a 30 minute incubation, the cells were harvested in a protein extraction buffer. The signaling of human leptin in the cells, measured by its ability to stimulate tyrosine phosphorylation on STAT3 in a western blot assay, was evaluated.

The results, in FIG. 13, show that the 6-mer of the '388 patent (SEQ ID NO:3), at concentrations as high as 0.8 μM (or 800 nM), was unable to block the negative effect of human CRP on the signaling capability of human leptin measured by leptin-stimulated activation of a transcription factor, STAT3. In the same set of experiments, Peptide-E was able to restore the signaling capability of human leptin (FIG. 13).

Five major protein species bound to a human leptin column having apparent molecular weights on silver-stained SDS-gel of ~30, 42, ~65, ~70, and ~85 Kd (FIG. 1B) have been characterized. These species have been termed SLIP-1, 2, 3, 4, and 5, respectively.

DEFINITIONS

The terms "Peptide E nucleotide", or "Peptide E polynucleotide" refer to a nucleic acid molecule comprising or consisting of a nucleotide sequence as set forth in SEQ ID NO:1, a nucleotide sequence encoding the polypeptide of SEQ ID NO:2, and further nucleic acid molecules as defined herein.

The term "isolated nucleic acid molecule" refers to a nucleic acid molecule that (1) has been separated from at least about 50 percent of proteins, lipids, carbohydrates, or other materials with which it is naturally found when total nucleic acid is isolated from source cells, (2) is not linked to all or a portion of a polynucleotide to which the "isolated nucleic acid molecule" is linked in nature, (3) is operably linked to a polynucleotide that it is not linked to in nature, or (4) does not occur in nature as part of a larger polynucleotide sequence. An isolated polynucleotide molecule may be free or substantially free of contaminating nucleic acid molecules or other contaminants that are found in its natural environment that would interfere with its use in polypeptide production or its therapeutic, diagnostic, prophylactic, or research use.

The term "nucleic acid sequence" or "nucleic acid molecule" refers to a DNA or RNA sequence. The term includes peptidomimemetics. Peptidomimetics may include, for example, but are not limited to those with reduced isostere pseudopeptide bonds, N-glycine replacement, and/or retro-inverso pseudopeptide bonds. The term encompasses molecules formed from any of the known base analogues of DNA and RNA.

The term "vector" refers to any molecule used to transfer coding information to a host cell. A vector may be, for example, but is not limited to, a nucleic acid, a plasmid, a cosmid, a phage, or a virus.

The term "expression vector" refers to a vector that is suitable for transformation of a host cell and contains nucleic acid sequences that direct and/or control the expression of inserted heterologous nucleic acid sequences. Expression includes, but is not limited to, processes such as transcription, translation, and RNA splicing, if introns are present.

The term "operably linked" refers to an arrangement of flanking sequences wherein the flanking sequences are configured or assembled so that they perform their usual function. Therefore, a flanking sequence operably linked to a coding sequence may be capable of effecting the replication, transcription, and/or translation of the coding sequence. For example, a coding sequence is operably linked to a promoter when the promoter is capable of directing transcription of that coding sequence. A flanking sequence does not need to be contiguous with a coding sequence, so long as correct function is retained.

The term "host cell" refers to a cell that has been transformed, or is capable of being transformed with a nucleic acid sequence and of expressing a selected gene. "Host cell" includes progeny of the parent cell, no matter if the progeny is identical to the parent cell, so long as the selected gene remains present.

The term "Peptide E polypeptide" refers to a polypeptide comprising the amino acid sequence of SEQ ID NO:2 and related polypeptides. Related polypeptides include Peptide E polypeptide fragments, Peptide E orthologs, Peptide E polypeptide variants, and Peptide E polypeptide derivatives. Related polypeptides have at least one activity of the polypeptide of SEQ ID NO:2. Peptide E polypeptides may be mature polypeptides and may or may not have an amino-terminal methionine residue, depending on the method by which they are prepared.

The term "Peptide E polypeptide fragment" refers to a polypeptide that comprises a truncation at the amino-terminus (with or without a leader sequence) and/or a truncation at the carboxyl-terminus of the polypeptide of SEQ ID NO:2. The term "Peptide E polypeptide fragment" also refers to amino-terminal and/or carboxyl-terminal truncations of Peptide E polypeptide orthologs, Peptide E polypeptide derivatives, or Peptide E polypeptide variants. Membrane-bound forms of a Peptide E polypeptide are also contemplated herein. Peptide E polypeptide fragments may optionally comprise an amino-terminal methionine residue.

The term "Peptide E polypeptide ortholog" refers to a polypeptide from another species that corresponds to the Polypeptide E amino acid sequence of SEQ ID NO:2. For example, rat Peptide E polypeptides and human Peptide E polypeptides are considered orthologs of each other.

The term "Peptide E polypeptide variants" refers to Peptide E polypeptides comprising amino acid sequences having one or more amino acid sequence substitutions, deletions (such as internal deletions and/or Peptide E polypeptide fragments), and/or additions (such as internal additions and/or Peptide E fusion polypeptides) as compared to the Peptide E polypeptide amino acid sequence of SEQ ID NO: 2 (with or without a leader sequence). Variants may be naturally occurring (for example, Peptide E polypeptide orthologs) or artificially constructed. Such Peptide E polypeptide variants may be prepared from the corresponding nucleic acid molecules having a DNA sequence that varies accordingly from the DNA sequence as set forth in SEQ ID NO: 1. In preferred embodiments, the variants have from 1 to 3, or from 1 to 5, or from 1 to 10, or from 1 to 15, or from 1 to 20 amino acid substitutions, insertions, additions and/or deletions, wherein the substitutions may be conservative, or non-conservative, or any combination thereof.

The term "Peptide E polypeptide derivatives" refers to the polypeptide of SEQ ID NO: 2, Peptide E polypeptide fragments, Peptide E polypeptide orthologs, or Peptide E polypeptide variants, as defined herein, that have been chemically modified.

The term "Peptide E fusion polypeptide" refers to a fusion of one or more amino acids (such as a heterologous protein or peptide) at the amino- or carboxyl-terminus of the polypeptide as set forth in SEQ ID NO: 2, Peptide E polypeptide fragments, Peptide E orthologs, Peptide E polypeptide variants, or Peptide E derivatives, as defined herein.

The term "biologically active Peptide E polypeptides" refers to Peptide E polypeptides having at least one activity characteristic of the polypeptide comprising the amino acid sequence of SEQ ID NO: 2.

The term "isolated polypeptide" refers to a polypeptide that (1) has been separated from at least about 50 percent of polynucleotides, lipids, carbohydrates, or other materials with which it is naturally found when isolated from the source cell, (2) is not linked (by covalent or noncovalent interaction) to all or a portion of a polypeptide to which the "isolated polypeptide" is linked in nature, (3) is operably linked (by covalent or noncovalent interaction) to a polypeptide with which it is not linked in nature, or (4) does not occur in nature. Preferably, the isolated polypeptide is substantially free from any other contaminating polypeptides or other contaminants that are found in its natural environment that would interfere with its therapeutic, diagnostic, prophylactic or research use.

The term "identity," as known in the art, refers to a relationship between the sequences of two or more polypeptide molecules or two or more nucleic acid molecules, as determined by comparing the sequences. In the art, "identity" also means the degree of sequence relatedness between nucleic acid molecules or polypeptides, as the case may be, as determined by the match between strings of two or more nucleotide or two or more amino acid sequences. "Identity" measures the percent of identical matches between the smaller of two or more sequences with gap alignments (if any) addressed by a particular mathematical model or computer program (i.e., "algorithms").

The term "similarity" is a related concept, but in contrast to "identity," "similarity" refers to a measure of relatedness which includes both identical matches and conservative substitution matches. If two polypeptide sequences have, for example, 10 identical amino acids for every 20 amino acids, and the remainder are all non-conservative substitutions, then the percent identity and similarity would both be 50%. If in the same example, there are five more positions where there are conservative substitutions, then the percent identity remains 50%, but the percent similarity would be 75% (15 of 20). Therefore, in cases where there are conservative substitutions, the percent similarity between two polypeptides will be higher than the percent identity between those two polypeptides.

The term "naturally occurring" or "native" when used in connection with biological materials such as nucleic acid molecules, polypeptides, host cells, and the like, refers to materials that are found in nature and are not manipulated by man. Similarly, "non-naturally occurring" or "non-native" refers to a material that is not found in nature or that has been structurally modified or synthesized by man.

The terms "effective amount" and "therapeutically effective amount" each refer to the amount of a Peptide E polypeptide or Peptide E nucleic acid molecule used to support an observable level of one or more biological activities of the Peptide E polypeptides as set forth herein.

The term "pharmaceutically acceptable carrier" or "physiologically acceptable carrier" as used herein refers to one or more formulation materials suitable for accomplishing or enhancing the delivery of the Peptide E polypeptide or Peptide E nucleic acid molecule as a pharmaceutical composition.

The term "transduction" refers to the transfer of genes from one bacterium to another, usually by a phage. "Transduction" also refers to the acquisition and transfer of eukaryotic cellular sequences by retroviruses.

The term "transfection" refers to the uptake of foreign or exogenous DNA by a cell, and a cell has been "transfected" when the exogenous DNA has been introduced inside the cell membrane. A number of transfection techniques are well known in the art and are disclosed herein. See, e.g., Graham et. al., 1973, *Virology* 52:456; Sambrook et al., Molecular Cloning, A Laboratory Manual (Cold Spring Harbor Laboratories, 1989); Davis et al., Basic Methods in Molecular Biology (Elsevier, 1986); and Chu et al., 1981, *Gene* 13:197. Such techniques can be used to introduce one or more exogenous DNA moieties into suitable host cells.

The term "transformation" refers to a change in a cell's genetic characteristics, and a cell has been transformed when it has been modified to contain a new DNA. For example, a cell is transformed where it is genetically modified from its native state. Following transfection or transduction, the transforming DNA may recombine with that of the cell by physically integrating into a chromosome of the cell, may be maintained transiently as an episomal element without being replicated, or may replicate independently as a plasmid. A cell is considered to have been stably transformed when the DNA is replicated with the division of the cell. Related Nucleic Acid Molecules and/or Polypeptides Related nucleic acid molecules may include a nucleotide sequence encoding a polypeptide comprising or consisting essentially of a substitution, modification, addition and/or deletion of one or more amino acid residues compared to the polypeptide of SEQ ID NO: 2. Such related Peptide E polypeptides may comprise, for example, an addition and/or a deletion of one or more N-linked or O-linked glycosylation sites or an addition and/or a deletion of one or more cysteine residues.

Related nucleic acid molecules also include fragments of Peptide E nucleic acid molecules that encode a polypeptide of at least about 5 contiguous amino acids, or about 10 amino acids, or about 15 amino acids, or about 20 amino acids, or about 25 amino acids, or more than about 25 amino acid residues of the Peptide E polypeptide of SEQ ID NO: 2.

In addition, related Peptide E nucleic acid molecules may also include those molecules which comprise nucleotide sequences which hybridize under moderately or highly stringent conditions as defined herein with the fully complementary sequence of the Peptide E nucleic acid molecule of SEQ ID NO: 1, or of a molecule encoding a polypeptide, which polypeptide comprises the amino acid sequence as shown in SEQ ID NO: 2, or of a nucleic acid fragment as defined herein, or of a nucleic acid fragment encoding a polypeptide as defined herein. Hybridization probes may be prepared using the Peptide E sequences provided herein to screen cDNA, genomic or synthetic DNA libraries for related sequences. Regions of the DNA and/or amino acid sequence of Peptide E polypeptide that exhibit significant identity to known sequences are readily determined using sequence alignment algorithms as described herein and those regions may be used to design probes for screening.

The term "highly stringent conditions" refers to those conditions that are designed to permit hybridization of DNA strands whose sequences are highly complementary, and to exclude hybridization of significantly mismatched DNAs.

Hybridization stringency is principally determined by temperature, ionic strength, and the concentration of denaturing agents such as formamide. Examples of "highly stringent conditions" for hybridization and washing are 0.015 M sodium chloride, 0.0015 M sodium citrate at 65-68° C. or 0.015 M sodium chloride, 0.0015 M sodium citrate, and 50% formamide at 42° C. See Sambrook, et al., Molecular Cloning: A Laboratory Manual (2nd ed., Cold Spring Harbor Laboratory, 1989); Anderson et al., Nucleic Acid Hybridisation: A Practical Approach Ch. 4 (IRL Press Limited).

More stringent conditions (such as higher temperature, lower ionic strength, higher formamide, or other denaturing agent) may also be used; however, the rate of hybridization will be affected. Other agents may be included in the hybridization and washing buffers for the purpose of reducing non-specific and/or background hybridization. Examples are 0.1% bovine serum albumin, 0.1% polyvinyl-pyrrolidone, 0.1% sodium pyrophosphate, 0.1% sodium dodecylsulfate, $NaDodSO_4$, (SDS), ficoll, Denhardt's solution, sonicated salmon sperm DNA (or another non-complementary DNA), and dextran sulfate, although other suitable agents can also be used. The concentration and types of these additives can be changed without substantially affecting the stringency of the hybridization conditions. Hybridization experiments are usually carried out at pH 6.8-7.4; however, at typical ionic strength conditions, the rate of hybridization is nearly independent of pH. See Anderson et al., Nucleic Acid Hybridisation: A Practical Approach Ch. 4 (IRL Press Limited).

Factors affecting the stability of DNA duplex include base composition, length, and degree of base pair mismatch. Hybridization conditions can be adjusted by one skilled in the art to accommodate these variables and allow DNA of different sequence relatedness to form hybrids. The melting temperature of a perfectly matched DNA duplex can be estimated by the following equation:

$$T_m(°C.)=81.5+16.6(\log [Na+])+0.41(\% G+C)-600/N-0.72(\% \text{ formamide})$$

where N is the length of the duplex formed, [Na+] is the molar concentration of the sodium ion in the hybridization or washing solution, and % G+C is the percentage of (guanine+cytosine) bases in the hybrid. For imperfectly matched hybrids, the melting temperature is reduced by approximately 1° C. for each 1% mismatch.

The term "moderately stringent conditions" refers to conditions under which a DNA duplex with a greater degree of base pair mismatching than could occur under "highly stringent conditions" is able to form. Examples of typical "moderately stringent conditions" are 0.015 M sodium chloride, 0.0015 M sodium citrate at 50-65° C. or 0.015 M sodium chloride, 0.0015 M sodium citrate, and 20% formamide at 37-50° C. By way of example, "moderately stringent conditions" of 50° C. in 0.015 M sodium ion will allow about a 21% mismatch. It will be appreciated by those skilled in the art that there is no absolute distinction between "highly stringent conditions" and "moderately stringent conditions." High stringency washing conditions for oligonucleotides are usually at a temperature of 0-5° C. below the $T_m$ of the oligonucleotide in 6×SSC, 0.1% SDS.

Related nucleic acid molecules comprise or consist of a nucleotide sequence that is at least about 70 percent identical to the nucleotide sequence as shown in SEQ ID NO: 1, or comprise or consist essentially of a nucleotide sequence encoding a polypeptide that is at least about 70 percent identical to the polypeptide as set forth in SEQ ID NO: 2. In preferred embodiments, the nucleotide sequences are about 75 percent, or about 80 percent, or about 85 percent, or about 90 percent, or about 95, 96, 97, 98, or 99 percent identical to the nucleotide sequence as shown in SEQ ID NO: 1, or the nucleotide sequences encode a polypeptide that is about 75 percent, or about 80 percent, or about 85 percent, or about 90 percent, or about 95, 96, 97, 98, or 99 percent identical to the polypeptide sequence as set forth in SEQ ID-NO: 2. Related nucleic acid molecules encode polypeptides possessing at least one activity of the polypeptide set forth in SEQ ID NO:2

Conservative modifications to the amino acid sequence of SEQ ID NO: 2 (and the corresponding modifications to the encoding nucleotides) will produce a polypeptide having functional and chemical characteristics similar to those of Peptide E polypeptides. For example, a "conservative amino acid substitution" may involve a substitution of a native amino acid residue with a normative residue such that there is little or no effect on the polarity or charge of the amino acid residue at that position. Furthermore, any native residue in the polypeptide may be substituted with alanine, a process known as "alanine scanning mutagenesis."

Conservative amino acid substitutions may also encompass non-naturally occurring amino acid residues that are typically incorporated by chemical peptide synthesis rather than by synthesis in biological systems. These include peptidomimetics, and other reversed or inverted forms of amino acid moieties.

Naturally occurring residues may be divided into classes based on common side chain properties:
1) hydrophobic: norleucine, Met, Ala, Val, Leu, Ile;
2) neutral hydrophilic: Cys, Ser, Thr;
3) acidic: Asp, Glu;
4) basic: Asn, Gln, His, Lys, Arg;
5) residues that influence chain orientation: Gly, Pro; and
6) aromatic: Trp, Tyr, Phe.

Non-conservative substitutions may involve the exchange of a member of one of these classes for a member from another class. Such substituted residues may be introduced into regions of the human Peptide E polypeptide that are homologous with non-human Peptide E polypeptides, or into the non-homologous regions of the molecule.

In making such changes, the hydropathic index of amino acids may be considered. Each amino acid has been assigned a hydropathic index on the basis of its hydrophobicity and charge characteristics. The hydropathic indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte et al., 1982, *J. Mol. Biol.* 157:105-31). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood, in the art that the substitution of like amino acids can be made effectively on the basis of hydrophilicity, particularly where the biologically functionally equivalent protein or peptide thereby created is intended for use in immunological embodiments, as in the present case. The greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0.+−0.1); glutamate (+3.0.+−0.1) serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). In making changes based upon similar hydrophilicity values, the substitution of amino acids whose hydrophilicity values are within ±2 is preferred, those which are within ±1 are particularly preferred, and those within ±0.5 are even more particularly preferred. One may also identify epitopes from primary amino acid sequences on the basis of hydrophilicity. These regions are also referred to as "epitopic core regions."

Desired amino acid substitutions (whether conservative or non-conservative) can be determined by those skilled in the art at the time such substitutions are desired. For example, amino acid substitutions can be used to identify important residues of the Peptide E polypeptide, or to increase or decrease the affinity of the Peptide E polypeptides described herein. Exemplary amino acid substitutions are set forth in Table I.

TABLE I

Amino Acid Substitutions

| Original Residues | Exemplary Substitutions | Preferred Substitutions |
| --- | --- | --- |
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Heu, Val, Met, Ala, Phe, Norleucine | Leu |
| Leu | Norleucine, Ile, Val, Met, Ala, Phe | Ile |
| Lys | Arg, 1,4 Diaminobutyric acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tye |
| Tyr | Trp, Phe, Thr, Ser | Phe |
| Val | Ile, Met, Leu, Phe, Ala, Norleucine | Phe |

A skilled artisan will be able to determine suitable variants of the polypeptide as set forth in SEQ ID NO: 2 using well-known techniques. For identifying suitable areas of the molecule that may be changed without destroying biological activity, one skilled in the art may target areas not believed to be important for activity. For example, when similar polypeptides with similar activities from the same species or from other species are known, one skilled in the art may compare the amino acid sequence of a Peptide E polypeptide to such similar polypeptides. With such a comparison, one can identify residues and portions of the molecules that are conserved among similar polypeptides.

It will be appreciated that changes in areas of the Peptide E molecule that are not conserved relative to such similar polypeptides would be less likely to adversely affect the biological activity and/or structure of a Peptide E polypeptide. One skilled in the art would also know that, even in relatively conserved regions, one may substitute chemically similar amino acids for the naturally occurring residues while retaining activity (conservative amino acid residue-substitutions). Therefore, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a Peptide E polypeptide that correspond to amino acid residues that are important for activity or structure in similar polypeptides.

The variants could be screened using activity assays known to those with skill in the art. Such variants could be used to gather information about other suitable variants. For example, if one discovered that a change to a particular amino acid residue resulted in destroyed, undesirably reduced, or unsuitable activity, variants with such a change would be avoided. In other words, based on information gathered from such routine experiments and based on the information provided herein, one skilled in the art can readily determine the amino acids where further substitutions should be avoided either alone or in combination with other mutations.

Peptide E polypeptide variants include glycosylation variants wherein the number and/or type of glycosylation sites have been altered compared to the amino acid sequence set forth in SEQ ID NO: 2. In one embodiment, Peptide E polypeptide variants comprise a greater or a lesser number of N-linked glycosylation sites than the amino acid sequence set forth in SEQ ID NO: 2. An N-linked glycosylation site is characterized by the sequence: Asn-X-Ser or Asn-X-Thr, wherein the amino acid residue designated as X may be any amino acid residue except proline.

In other embodiments, related nucleic acid molecules comprise or consist of a nucleotide sequence encoding a polypeptide as set forth in SEQ ID NO: 2 with at least one amino acid insertion and wherein the polypeptide has an activity of the polypeptide set forth in SEQ ID NO: 2, or a nucleotide sequence encoding a polypeptide as set forth in SEQ ID NO: 2 with at least one amino acid deletion and wherein the polypeptide has an activity of the polypeptide set forth in SEQ ID NO: 2.

Related nucleic acid molecules also comprise or consist of a nucleotide sequence encoding a polypeptide as set forth in SEQ ID NO: 2 wherein the polypeptide has a carboxyl- and/or amino-terminal truncation and further wherein the polypeptide has an activity of the polypeptide set forth in SEQ ID NO: 2. Related nucleic acid molecules also comprise or consist of a nucleotide sequence encoding a polypeptide as set forth in SEQ ID NO: 2 with at least one modification selected from the group consisting of amino acid substitutions, amino acid insertions, amino acid deletions, carboxyl-terminal truncations, and amino-terminal truncations and wherein the polypeptide has an activity of the polypeptide set forth in SEQ ID NO: 2.

In addition, the polypeptide comprising the amino acid sequence of SEQ ID NO: 2, or other Peptide E polypeptide, may be fused to a homologous polypeptide to form a homodimer or to a heterologous polypeptide to form a heterodimer. Heterologous peptides and polypeptides include, but are not limited to: an epitope to allow for the detection and/or isolation of a Peptide E fusion polypeptide; a transmembrane receptor protein or a portion thereof, such as an extracellular domain or a transmembrane and intracellular domain; a ligand or a portion thereof which binds to a transmembrane receptor protein; an enzyme or portion thereof which is catalytically active; a polypeptide or peptide that promotes oligomerization, such as a leucine zipper domain; a polypeptide or peptide that increases stability, such as an immunoglobulin constant region; and a polypeptide that has a therapeutic activity different from the polypeptide comprising the amino acid sequence as set forth in SEQ ID NO: 2, or other Peptide E polypeptide.

Fusions can be made either at the amino-terminus or at the carboxyl-terminus of the polypeptide comprising the amino acid sequence set forth in SEQ ID NO: 2, or other Peptide E polypeptide. Fusions may be direct with no linker or adapter molecule or may be through a linker or adapter molecule. A linker or adapter molecule may be one or more amino acid residues, typically from about 20 to about 50 amino acid residues. A linker or adapter molecule may also be designed with a cleavage site for a DNA restriction endonuclease or for a protease to allow for the separation of the fused moieties.

Identity and similarity of related nucleic acid molecules and polypeptides are readily calculated by known methods. Such methods include, but are not limited to those described in Computational Molecular Biology (A. M. Lesk, ed., Oxford University Press 1988); Biocomputing: Informatics and Genome Projects (D. W. Smith, ed., Academic Press 1993); Computer Analysis of Sequence Data (Part 1, A. M. Griffin and H. G. Griffin, eds., Humana Press 1994); G. von Heinle, Sequence Analysis in Molecular Biology (Academic Press 1987); Sequence Analysis Primer (M. Gribskov and J. Devereux, eds., M. Stockton Press 1991); and Carillo et al., 1988, *SIAM J. Applied Math.*, 48:1073.

Preferred methods to determine identity and/or similarity are designed to give the largest match between the sequences tested. Methods to determine identity and similarity are described in publicly available computer programs. Preferred computer program methods to determine identity and similarity between two sequences include, but are not limited to, the GCG program package, including GAP (Devereux et al., 1984, *Nucleic Acids Res.* 12:387; Genetics Computer Group, University of Wisconsin, Madison, Wis.), BLASTP, BLASTN, and FASTA (Altschul et al., 1990, *J. Mol. Biol.* 215:403-10). The BLASTX program is publicly available from the National Center for Biotechnology Information (NCBI) and other sources (Altschul et al., BLAST Manual (NCB NLM NIH, Bethesda, Md.); Altschul et al., 1990, supra). The well-known Smith-Waterman algorithm may also be used to determine identity.

Other exemplary algorithms, gap-opening penalties, gap extension penalties, comparison matrices, and thresholds of similarity may be used, including those set forth in the Program Manual, Wisconsin Package, Version 9, September, 1997. The particular choices to be made will be apparent to those of skill in the art and will depend on the specific comparison to be made, such as DNA-to-DNA, protein-to-protein, protein-to-DNA; and additionally, whether the comparison is between given pairs of sequences (in which case GAP or BestFit are generally preferred) or between one sequence and a large database of sequences (in which case FASTA or BLASTA are preferred).

Nucleic Acid Molecules

The nucleic acid molecules encoding a polypeptide comprising the amino acid sequence of a Peptide E polypeptide can readily be obtained in a variety of ways including, for example, but not limited to, chemical synthesis, cDNA or genomic library screening, expression library screening, and/or PCR amplification of cDNA.

Recombinant DNA methods used herein are generally those set forth in Sambrook et al., Molecular Cloning: A Laboratory Manual (Cold Spring Harbor Laboratory Press, 1989) and/or Current Protocols in Molecular Biology (Ausubel et al., eds., Green Publishers Inc. and Wiley and Sons 1994). Another embodiment provides nucleic acid molecules as described herein and methods for obtaining such molecules.

Recombinant expression techniques conducted in accordance with the descriptions set forth below may be followed to produce these polynucleotides and to express the encoded polypeptides. For example, by inserting a nucleic acid sequence that encodes the amino acid sequence of a Peptide E polypeptide into an appropriate vector, one skilled in the art can readily produce large quantities of the desired nucleotide sequence. The sequences can then be used to generate detection probes or amplification primers. Alternatively, a polynucleotide encoding the amino acid sequence of a Peptide E polypeptide can be inserted into an expression vector. By introducing the expression vector into an appropriate host, the encoded Peptide E polypeptide may be produced in large amounts.

Another method for obtaining a suitable nucleic acid sequence is the polymerase chain reaction (PCR). In this method, cDNA is prepared from poly(A)+ RNA or total RNA using the enzyme reverse transcriptase. Two primers, typically complementary to two separate regions of cDNA encoding the amino acid sequence of a Peptide E polypeptide, are then added to the cDNA along with a polymerase such as Taq polymerase, and the polymerase amplifies the cDNA region between the two primers.

Another means of preparing a nucleic acid molecule encoding the amino acid sequence of a Peptide E polypeptide is chemical synthesis using methods known to the skilled artisan such as those described by Engels et al., 1989, *Angew. Chem. Intl. Ed.* 28:716-34. These methods include, for example, but are not limited to, phosphotriester, phosphoramidite, and H-phosphonate methods for nucleic acid synthesis.

In some cases, it may be desirable to prepare nucleic acid molecules encoding Peptide E polypeptide variants. Nucleic acid molecules encoding variants may be produced using site directed mutagenesis, PCR amplification, or other appropriate methods, where the primer(s) have the desired point mutations (see Sambrook et al., supra, and Ausubel et al., supra, for descriptions of mutagenesis techniques). Chemical synthesis using methods described by Engels et al., supra, may also be used to prepare such variants. Other methods known to the skilled artisan may be used as well.

Vectors and Host Cells

A nucleic acid molecule encoding the amino acid sequence of a Peptide E polypeptide may be inserted into an appropriate expression vector using standard ligation techniques. The vector is typically selected to be functional in the particular host cell employed (i.e., the vector is compatible with the host cell machinery such that amplification of the gene and/or expression of the gene can occur). A nucleic acid molecule encoding the amino acid sequence of a Peptide E polypeptide may be amplified/expressed in prokaryotic, yeast, insect (baculovirus systems) and/or eukaryotic host cells.

Selection of the host cell will depend in part on whether a Peptide E polypeptide is to be post-translationally modified (e.g., glycosylated and/or phosphorylated). If so, yeast, insect, or mammalian host cells are preferable. For a review of expression vectors, see Meth. Enz., vol. 185 (D. V. Goeddel, ed., Academic Press 1990).

Typically, expression vectors used in any of the host cells will contain sequences for plasmid maintenance and for cloning and expression of exogenous nucleotide sequences. Such sequences, collectively referred to as "flanking sequences" in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Each of these sequences is discussed below.

Flanking sequences may be homologous (i.e., from the same species and/or strain as the host cell), heterologous (i.e., from a species other than the host cell species or strain), hybrid (i.e., a combination of flanking sequences from more than one source), or synthetic. As such, the source of a flanking sequence may be any prokaryotic or eukaryotic organism, any vertebrate or invertebrate organism, or any plant, provided that the flanking sequence is functional in, and can be activated by, the host cell machinery.

A transcription termination sequence is typically located 3' of the end of a polypeptide coding region and serves to terminate transcription. Usually, a transcription termination sequence in prokaryotic cells is a G-C rich fragment followed by a poly-T sequence. While the sequence is easily cloned from a library or even purchased commercially as part of a vector, it can also be readily synthesized using methods for nucleic acid synthesis such as those described herein.

A ribosome binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of a Peptide E polypeptide to be expressed. The Shine-Dalgarno sequence is varied but is typically a polypurine (i.e., having a high A-G content). Many Shine-Dalgarno sequences have been identified, each of which can be readily synthesized using methods set forth herein and used in a prokaryotic vector.

A leader, or signal, sequence may be used to direct a Peptide E polypeptide out of the host cell. Typically, a nucleotide sequence encoding the signal sequence is positioned in the coding region of a Peptide E nucleic acid molecule, or directly at the 5' end of a Peptide E polypeptide coding region. Many signal sequences have been identified, and any of those that are functional in the selected host cell may be used in conjunction with a Peptide E nucleic acid molecule. Therefore, a signal sequence may be homologous (naturally occurring) or heterologous to the Peptide E nucleic acid molecule. Additionally, a signal sequence may be chemically synthesized using methods described herein.

In most cases, the secretion of a Peptide E polypeptide from the host cell via the presence of a signal peptide will result in the removal of the signal peptide from the secreted Peptide E polypeptide. The signal sequence may be a component of the vector, or it may be a part of a Peptide E nucleic acid molecule that is inserted into the vector.

In some cases, such as where glycosylation is desired in a eukaryotic host cell expression system, the various presequences may be manipulated to improve glycosylation or yield. For example, one may alter the peptidase cleavage site of a particular signal peptide, or add pro-sequences, which also may affect glycosylation. The final protein product may have, in the −1 position (relative to the first amino acid of the mature protein) one or more additional amino acids incident to expression, which may not have been totally removed. For example, the final protein product may have one or two amino acid residues found in the peptidase cleavage site, attached to the amino-terminus. Alternatively, use of some enzyme cleavage sites may result in a slightly truncated form of the desired Peptide E polypeptide, if the enzyme cuts at such area within the mature polypeptide.

Expression and cloning vectors will typically contain a promoter that is recognized by the host organism and operably linked to the molecule encoding the Peptide E polypeptide. Promoters are untranscribed sequences located upstream (i.e., 5') to the start codon of a structural gene (generally within about 100 to 1000 bp) that control the transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, initiate continual gene product production; that is, there is little or no control over gene expression.

A large number of promoters, recognized by a variety of potential host cells, are well known. A suitable promoter is operably linked to the DNA encoding Peptide E polypeptide by removing the promoter from the source DNA by restriction enzyme digestion and inserting the desired promoter sequence into the vector. The native Peptide E promoter sequence may be used to direct amplification and/or expression of a Peptide E nucleic acid molecule. A heterologous promoter is preferred, however, if it permits greater transcription and higher yields of the expressed protein as compared to the native promoter, and if it is compatible with the host cell system that has been selected for use.

Promoters suitable for use with prokaryotic hosts include the beta-lactamase and lactose promoter systems; alkaline phosphatase; a tryptophan (trp) promoter system; and hybrid promoters such as the tac promoter. Other known bacterial promoters are also suitable. Their sequences have been published, thereby enabling one skilled in the art to ligate them to the desired DNA sequence, using linkers or adapters as needed to supply any useful restriction sites.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus and most preferably Simian Virus 40 (SV40). Other suitable mammalian promoters include heterologous mammalian promoters, for example, heat-shock promoters and the actin promoter.

Additional promoters that may be of interest in controlling Peptide E gene expression include, but are not limited to: the SV40 early promoter region (Bernoist and Chambon, 1981, *Nature* 290:304-10); the CMV promoter; the promoter contained in the 3' long terminal repeat of Rous sarcoma virus (Yamamoto, et al., 1980, *Cell* 22:787-97); the herpes thymidine kinase promoter (Wagner et al., 1981, *Proc. Natl. Acad. Sci. U.S.A.* 78:1444-45); the regulatory sequences of the metallothionine gene (Brinster et al., 1982, *Nature* 296:39-42); prokaryotic expression vectors such as the beta-lactamase promoter (Villa-Kamaroff et al., 1978, *Proc. Natl. Acad. Sci. U.S.A.*, 75:3727-31); or the tac promoter (DeBoer et al., 1983, *Proc. Natl. Acad. Sci. U.S.A.*, 80:21-25).

An enhancer sequence may be inserted into the vector to increase the transcription of a DNA encoding a Peptide E polypeptide by higher eukaryotes. Enhancers are cis-acting elements of DNA, usually about 10-300 bp in length, that act on the promoter to increase transcription. Enhancers are relatively orientation and position independent. They have been found 5' and 3' to the transcription unit. Several enhancer sequences available from mammalian genes are known (e.g., globin, elastase, albumin, alpha-feto-protein and insulin). An enhancer from a virus may be used. The SV40 enhancer, the cytomegalovirus early promoter enhancer, the polyoma enhancer, and adenovirus enhancers are exemplary enhancing elements for the activation of eukaryotic promoters. While an enhancer may be spliced into the vector at a position 5' or 3' to a Peptide E nucleic acid molecule, it is typically located at a site 5' from the promoter.

Expression vectors may be constructed from a starting vector such as a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art.

Preferred vectors are those that are compatible with bacterial, insect, and mammalian host cells. Such vectors include, for example, but are not limited to, pCRII, pCR3, and pcDNA3.1 (Invitrogen, San Diego, Calif.), pBSII (Stratagene, La Jolla, Calif.), pET15 (Novagen, Madison, Wis.), pGEX (Pharmacia Biotech, Piscataway, N.J.), pEGFP-N2 (Clontech, Palo Alto, Calif.), pETL (BlueBacII, Invitrogen), pDSR-alpha (PCT Pub. No. WO 90/14363) and pFastBacDual (Gibco-BRL, Grand Island, N.Y.).

After the vector has been constructed and a nucleic acid molecule encoding a Peptide E polypeptide has been inserted into the proper site of the vector, the completed vector may be inserted into a suitable host cell for amplification and/or polypeptide expression. The transformation of an expression vector for a Peptide E polypeptide into a selected host cell may be accomplished by well known methods including methods such as transfection, infection, calcium chloride, electroporation, microinjection, lipofection, DEAE-dextran method, or other known techniques. The method selected will in part be a function of the type of host cell to be used. These methods and other suitable methods are well known to the skilled artisan, and are set forth, for example, in Sambrook et al., supra.

Host cells may be prokaryotic host cells (such as *E. coli*) or eukaryotic host cells (such as a yeast, insect, or vertebrate cell). The host cell, when cultured under appropriate conditions, synthesizes a Peptide E polypeptide that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

A number of suitable host cells are known in the art and many are available from the American Type Culture Collection (ATCC), Manassas, Va. Examples include, but are not limited to, mammalian cells, such as Chinese hamster ovary cells (CHO), CHO DHFR(-) cells (Urlaub et al., 1980, *Proc. Natl. Acad. Sci. U.S.A.* 97:4216-20), human embryonic kidney (HEK) 293 or 293T cells, or 3T3 cells. The selection of suitable mammalian host cells and methods for transformation, culture, amplification, screening, product production, and purification are known in the art. Other suitable mammalian cell lines include, but are not limited to, the monkey COS-1 and COS-7 cell lines and the CV-1 cell line.

Similarly useful as host cells are bacterial cells. For example, the various strains of *E. coli* (e.g., HB101, DH5.alpha., DH10, and MC1061) are well-known as host cells in the field of biotechnology. Various strains of *B. subtilis, Pseudomonas* spp., other *Bacillus* spp., *Streptomyces* spp., and the like may also be employed in this method.

Many strains of yeast cells known to those skilled in the art are also available as host cells for the expression of Peptide E polypeptides. Preferred yeast cells include, for example, *Saccharomyces cerivisae* and *Pichia pastoris*.

Additionally, where desired, insect cell systems may be utilized in the methods presented herein. Such systems are described, for example, in Kitts et al., 1993, Biotechniques, 14:810-17; Lucklow, 1993, *Curr. Opin. Biotechnol.* 4:564-72; and Lucklow et al., 1993, *J. Virol.*, 67:4566-79. Preferred insect cells are Sf-9 and Hi5 (Invitrogen).

One may also use transgenic animals to express glycosylated Peptide E polypeptides. For example, one may use a transgenic milk-producing animal (a cow or goat, for example) and obtain the glycosylated polypeptide in the animal milk. One may also use plants to produce Peptide E polypeptides; however, in general, the glycosylation occurring in plants is different from that produced in mammalian cells, and may result in a glycosylated product that is not suitable for human therapeutic use.

Polypeptide Production

Host cells comprising a Peptide E polypeptide expression vector may be cultured using standard media well known to the skilled artisan. The media will usually contain all nutrients necessary for the growth and survival of the cells. Suitable media for culturing *E. coli* cells include, for example, Luria Broth (LB) and/or Terrific Broth (TB). Suitable media for culturing eukaryotic cells include Roswell Park Memorial Institute medium 1640 (RPMI 1640), Minimal Essential Medium (MEM) and/or Dulbecco's Modified Eagle Medium (DMEM), all of which may be supplemented with serum and/or growth factors as necessary for the particular cell line being cultured.

The amount of Peptide E polypeptide produced by a host cell can be evaluated using standard methods known in the art. Such methods include, without limitation, Western blot analysis, SDS-polyacrylamide gel electrophoresis, non-denaturing gel electrophoresis, High Performance Liquid Chromatography (HPLC) separation, immunoprecipitation, and/or activity assays such as DNA binding gel shift assays.

If a Peptide E polypeptide has been designed to be secreted from host cells, the majority of polypeptide may be found in the cell culture medium. If however, the Peptide E polypeptide is not secreted from the host cells, it will be present in the cytoplasm and/or the nucleus (for eukaryotic host cells) or in the cytosol (for gram-negative bacteria host cells).

If a Peptide E polypeptide has formed inclusion bodies in the cytosol, the inclusion bodies can often bind to the inner and/or outer cellular membranes and thus will be found primarily in the pellet material after centrifugation. The pellet material can then be treated at pH extremes or with a chaotropic agent such as a detergent, guanidine, guanidine derivatives, urea, or urea derivatives in the presence of a reducing agent such as dithiothreitol at alkaline pH or tris-carboxyethyl phosphine at acid pH to release, break apart, and solubilize the inclusion bodies. The solubilized Peptide E polypeptide can then be analyzed using gel electrophoresis, immunoprecipitation, or the like. If isolation of the Peptide E polypeptide is desired, isolation may be accomplished using standard methods such as those described herein and in Marston et al., 1990, *Meth. Enz.,* 182:264-75.

Additionally, Peptide E polypeptides may be purified through the use of a monoclonal antibody that is capable of specifically recognizing and binding to a Peptide E polypeptide.

Peptide E polypeptides may also be prepared by chemical synthesis methods (such as solid phase peptide synthesis) using techniques known in the art such as those set forth by Merrifield et al., 1963, *J. Am. Chem. Soc.* 85:2149; Houghten et al., 1985, *Proc Natl Acad. Sci. U.S.A.* 82:5132; and Stewart and Young, Solid Phase Peptide Synthesis (Pierce Chemical Co. 1984). Such polypeptides may be synthesized with or without a methionine on the amino-terminus. Chemically synthesized Peptide E polypeptides may be oxidized using methods set forth in these references to form disulfide bridges. Chemically synthesized Peptide E polypeptides are expected to have biological activity comparable to the corresponding Peptide E polypeptides produced recombinantly or purified from natural sources, and thus may be used interchangeably with a recombinant or natural Peptide E polypeptide.

A number of additional methods for producing nucleic acids and polypeptides are known in the art, and the methods can be used to produce polypeptides having specificity for Peptide E polypeptide. See, e.g., Roberts et al., 1997, *Proc. Natl. Acad. Sci. U.S.A.* 94:12297-303, which describes the production of fusion proteins between an mRNA and its encoded peptide. See also, Roberts, 1999, *Curr. Opin. Chem. Biol.* 3:268-73. Peptide E polypeptides may also be used in creation of peptidomimetics. Peptidomimetics are molecules bearing an identifiable resemblance to a peptides, where, as a ligand of a biological receptor, it can imitate or inhibit the effect of a natural peptide. Peptidomimetics are reported in Giannis, et al., 1997, *Adv. Drug Res.* 29:1-78; Ripka, et al., 1998, *Curr. Opin. Chem. Bio.* 2:441-452; and Marshall, 1993, *Tetrahedron* 23:127-159, all of which are incorporated by reference herein.

Chemical Derivatives

Chemically modified derivatives of Peptide E polypeptides may be prepared by one skilled in the art, given the disclosures described herein. Peptide E polypeptide derivatives are modified in a manner that is different from Peptide E polypeptides, either in the type or location of the molecules naturally attached to the polypeptide. Derivatives may include molecules formed by the deletion of one or more naturally-attached chemical groups.

The polypeptide comprising the amino acid sequence of SEQ ID NO: 2, or other Peptide E polypeptide, may be modified by the covalent attachment of one or more polymers. For example, the polymer selected is typically water-soluble so that the protein to which it is attached does not precipitate in an aqueous environment, such as a physiological environment. Included within the scope of suitable polymers is a mixture of polymers. Preferably, for therapeutic use of the end-product preparation, the polymer will be pharmaceutically acceptable.

The polymers each may be of any molecular weight and may be branched or unbranched. The polymers each typically have an average molecular weight of between about 2 kDa to about 100 kDa (the term "about" indicating that in preparations of a water-soluble polymer, some molecules will weigh more, some less, than the stated molecular weight). The average molecular weight of each polymer is preferably between about 5 kDa and about 50 kDa, more preferably between about 12 kDa and about 40 kDa and most preferably between about 20 kDa and about 35 kDa.

Suitable water-soluble polymers or mixtures thereof include, but are not limited to, N-linked or O-linked carbohydrates, sugars, phosphates, polyethylene glycol (PEG) (including the forms of PEG that have been used to derivatize proteins, including mono-($C_1$-$C_{10}$), alkoxy-, or aryloxy-polyethylene glycol), monomethoxy-polyethylene glycol, dextran (such as low molecular weight dextran of, for example, about 6 kD), cellulose, or other carbohydrate based polymers, poly-(N-vinyl pyrrolidone) polyethylene glycol, propylene glycol homopolymers, polypropylene oxide/ethylene oxide co-polyoxyethylated polyols (e.g., glycerol), and polyvinyl alcohol. Also encompassed herein are bifunctional crosslinking molecules which may be used to prepare covalently attached Peptide E polypeptide multimers.

In general, chemical derivatization may be performed under any suitable condition used to react a protein with an activated polymer molecule. Methods for preparing chemical derivatives of polypeptides will generally comprise the steps of: (a) reacting the polypeptide with the activated polymer molecule (such as a reactive ester or aldehyde derivative of the polymer molecule) under conditions whereby the polypeptide comprising the amino acid sequence of SEQ ID NO: 2, or other Peptide E polypeptide, becomes attached to one or more polymer molecules, and (b) obtaining the reaction products. The optimal reaction conditions will be determined based on known parameters and the desired result. For example, the larger the ratio of polymer molecules to protein, the greater the percentage of attached polymer molecule. In one embodiment, the Peptide E polypeptide derivative may have a single polymer molecule moiety at the amino-terminus. See, e.g., U.S. Pat. No. 5,234,784.

The pegylation of a polypeptide may be specifically carried out using any of the pegylation reactions known in the art. Such reactions are described, for example, in the following publications: Francis et al., 1992, Focus on Growth Factors 3:4-10; European Patent Nos. 0154316 and 0401384; and U.S. Pat. No. 4,179,337. For example, pegylation may be carried out via an acylation reaction or an alkylation reaction with a reactive polyethylene glycol molecule (or an analogous reactive water-soluble polymer) as described herein. For the acylation reactions a selected polymer should have a single reactive ester group. For reductive alkylation, a selected polymer should have a single reactive aldehyde group. A reactive aldehyde is, for example, polyethylene glycol propionaldehyde, which is water stable, or mono $C_1$-$C_{10}$ alkoxy or aryloxy derivatives thereof (see U.S. Pat. No. 5,252,714).

Generally, conditions that may be alleviated or modulated by the administration of the present Peptide E polypeptide derivatives include those described herein for Peptide E polypeptides. However, the Peptide E polypeptide derivatives disclosed herein may have additional activities, enhanced or reduced biological activity, or other characteristics, such as increased or decreased half-life, as compared to the non-derivatized molecules.

Assaying for Other Modulators of Peptide E Polypeptide Activity

In some situations, it may be desirable to identify molecules that are modulators, i.e., agonists or antagonists, of the activity of Peptide E polypeptide. Natural or synthetic molecules that modulate Peptide E polypeptide may be identified using one or more screening assays, such as those described herein. Such molecules may be administered either in an ex vivo manner or in an in vivo manner by injection, or by oral delivery, implantation device, or the like.

"Test molecule" refers to a molecule that is under evaluation for the ability to modulate (i.e., increase or decrease) the activity of a Peptide E polypeptide. Most commonly, a test molecule will interact directly with a Peptide E polypeptide. However, it is also contemplated that a test molecule may also modulate Peptide E polypeptide activity indirectly, such as by binding to a Peptide E polypeptide binding partner (e.g., receptor or ligand). In one embodiment, a test molecule will bind to a Peptide E polypeptide with an affinity constant of at least about $10^{-6}$ M, preferably about $10^{-8}$ M, more preferably about $10^{-9}$ M, and even more preferably about $10^{-10}$ M.

Methods for identifying compounds that interact with Peptide E polypeptides are encompassed herein. In certain embodiments, a Peptide E polypeptide is incubated with a test molecule under conditions that permit the interaction of the test molecule with a Peptide E polypeptide, and the extent of the interaction is measured. The test molecule can be screened in a substantially purified form or in a crude mixture.

In certain embodiments, a Peptide E polypeptide agonist or antagonist may be a protein, peptide, carbohydrate, lipid, or small molecular weight molecule that interacts with Peptide E polypeptide to regulate its activity. Molecules that regulate Peptide E polypeptide expression include nucleic acids that are complementary to nucleic acids encoding a Peptide E polypeptide, or are complementary to nucleic acids sequences that direct or control the expression of Peptide E polypeptide, and that act as anti-sense regulators of expression.

Once a test molecule has been identified as interacting with a Peptide E polypeptide, the molecule may be further evaluated for its ability to increase or decrease Peptide E polypeptide activity. The measurement of the interaction of a test molecule with a Peptide E polypeptide may be carried out in several formats, including cell-based binding assays, membrane binding assays, solution-phase assays, and immunoassays. In general, a test molecule is incubated with a Peptide E polypeptide for a specified period of time, and Peptide E polypeptide activity is determined by one or more assays for measuring biological activity.

The interaction of test molecules with Peptide E polypeptides may also be assayed directly using polyclonal or monoclonal antibodies in an immunoassay. Alternatively, modified forms of Peptide E polypeptides containing epitope tags as described herein may be used in solution and immunoassays.

In vitro assays such as those described herein may be used advantageously to screen large numbers of compounds for an effect on the formation of a complex between a Peptide E polypeptide and a Peptide E polypeptide binding partner. A binding partner may be, for example, human CRP. The assays may be automated to screen compounds generated in phage display, synthetic peptide, and chemical synthesis libraries.

Compounds that increase or decrease the formation of a complex between a Peptide E polypeptide and a Peptide E polypeptide binding partner may also be screened in cell culture using cells and cell lines expressing either Peptide E polypeptide or Peptide E polypeptide binding partner. Cells and cell lines may be obtained from any mammal, but preferably will be from human or other primate, canine, or rodent sources. The binding of a Peptide E polypeptide to cells expressing Peptide E polypeptide binding partner at the surface is evaluated in the presence or absence of test molecules, and the extent of binding may be determined by, for example, flow cytometry using a biotinylated antibody to a Peptide E polypeptide binding partner. Cell culture assays can be used advantageously to further evaluate compounds that score positive in protein binding assays described herein.

Peptide E Polypeptide Compositions and Administration

A further embodiment provides therapeutic applications. Such Peptide E polypeptide pharmaceutical compositions may comprise a therapeutically effective amount of a Peptide E polypeptide or a Peptide E nucleic acid molecule in admixture with a pharmaceutically or physiologically acceptable formulation agent selected for suitability with the mode of administration. Acceptable formulation materials preferably are nontoxic to recipients at the dosages and concentrations employed.

The pharmaceutical composition may contain formulation materials for modifying, maintaining, or preserving, for example, the pH, osmolarity, viscosity, clarity, color, isotonicity, odor, sterility, stability, rate of dissolution or release, adsorption, or penetration of the composition. Suitable formulation materials include, but are not limited to, amino acids (such as glycine, glutamine, asparagine, arginine, or lysine), antimicrobials, antioxidants (such as ascorbic acid, sodium sulfite, or sodium hydrogen-sulfite), buffers (such as borate, bicarbonate, Tris-HCl, citrates, phosphates, or other organic acids), bulking agents (such as mannitol or glycine), chelating agents (such as ethylenediamine tetraacetic acid (EDTA)), complexing agents (such as caffeine, polyvinylpyrrolidone, beta-cyclodextrin, or hydroxypropyl-beta-cyclodextrin), fillers, monosaccharides, disaccharides, and other carbohydrates (such as glucose, mannose, or dextrins), proteins (such as serum albumin, gelatin, or immunoglobulins), coloring, flavoring and diluting agents, emulsifying agents, hydrophilic polymers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylparaben, propylparaben, chlorhexidine, sorbic acid, or hydrogen peroxide), solvents (such as glycerin, propylene glycol, or polyethylene glycol), sugar alcohols (such as manntitol or sorbitol), suspending agents, surfactants or wetting agents (such as pluronics; PEG; sorbitan esters; polysorbates such as polysorbate 20 or polysorbate 80; triton; tromethamine; lecithin; cholesterol or tyloxapal), stability enhancing agents (such as sucrose or sorbitol), tonicity enhancing agents (such as alkali metal halides, preferably sodium or potassium chloride, or mannitol sorbitol), delivery vehicles, diluents, excipients and/or pharmaceutical adjuvants. See Remington's Pharmaceutical Sciences (18th Ed., A. R. Gennaro, ed., Mack Publishing Company 1990).

The optimal pharmaceutical composition will be determined by a skilled artisan depending upon, for example, the intended route of administration, delivery format, and desired dosage. See, e.g., Remington's Pharmaceutical Sciences, supra. Such compositions may influence the physical state, stability, rate of in vivo release, and rate of in vivo clearance of the Peptide E polynucleotide or Peptide E polypeptide.

The primary vehicle or carrier in a pharmaceutical composition may be either aqueous or non-aqueous in nature. For example, a suitable vehicle or carrier for injection may be water, physiological saline solution, or artificial cerebrospinal fluid, possibly supplemented with other materials common in compositions for parenteral administration. Neutral buffered saline or saline mixed with serum albumin are further exemplary vehicles.

In a further embodiment, Peptide E polypeptide compositions may be prepared for storage by mixing the selected composition having the desired degree of purity with optional formulation agents (Remington's Pharmaceutical Sciences, supra) in the form of a lyophilized cake or an aqueous solution. Further, the Peptide E polypeptide product may be formulated as a lyophilizate using appropriate excipients such as sucrose.

A pharmaceutical composition may involve an effective quantity of Peptide E polypeptides in a mixture with non-toxic excipients that are suitable for the manufacture of tablets. By dissolving the tablets in sterile water, or another appropriate vehicle, solutions can be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional Peptide E polypeptide pharmaceutical compositions will be evident to those skilled in the art, including formulations involving Peptide E polypeptides in sustained- or controlled-delivery formulations. Techniques for formulating a variety of other sustained-delivery or controlled-delivery means, such as liposome carriers, bio-erodible microparticles or porous beads and depot injections, are also known to those skilled in the art. See, e.g., PCT/US93/00829, which reports the controlled release of porous polymeric microparticles for the delivery of pharmaceutical compositions.

In another embodiment, kits for producing a single-dose administration unit are provided. The kits may each contain both a first container having a dried protein and a second container having an aqueous formulation. Also included are kits containing single and multi-chambered pre-filled syringes (e.g., liquid syringes and lyosyringes).

The effective amount of a Peptide E pharmaceutical composition to be employed therapeutically will depend, for example, upon the therapeutic context and objectives. One skilled in the art will appreciate that the appropriate dosage levels for treatment will thus vary depending, in part, upon the indication for which the Peptide E polypeptide or nucleotide is being used, the route of administration, and the size (body weight, body surface, or organ size) and condition (the age and general health) of the patient. Accordingly, the clinician may titer the dosage and modify the route of administration to obtain the optimal therapeutic effect.

The frequency of dosing will depend upon the pharmacokinetic parameters of the Peptide E molecule in the formulation being used. Typically, a clinician will administer the composition until a dosage is reached that achieves the desired effect. The composition may therefore be administered as a single dose, as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages may be ascertained through use of appropriate dose-response data.

The route of administration of the pharmaceutical composition is in accord with known methods, including, for example, but not limited to, orally; through injection by intravenous, intraperitoneal, intracerebral (intraparenchymal), intracerebroventricular, intramuscular, intraocular, intraarterial, intraportal, or intralesional routes; by sustained release systems; or by implantation devices. Where desired, the compositions may be administered by bolus injection or continuously by infusion, or by implantation device.

Alternatively or additionally, the composition may be administered locally via implantation of a membrane, sponge, or other appropriate material onto which the desired molecule has been absorbed or encapsulated. Where an implantation device is used, the device may be implanted into any suitable tissue or organ, and delivery of the desired molecule may be via diffusion, timed-release bolus, or continuous administration.

In some cases, ex vivo use of Peptide E polypeptide pharmaceutical compositions may be desired. In such instances, cells, tissues, or organs that have been removed from the patient are exposed to a Peptide E polypeptide pharmaceutical compositions after which the cells, tissues, or organs are implanted into the patient.

Additional embodiments relate to cells and methods (e.g., homologous recombination and/or other recombinant production methods) for both the in vitro production of therapeutic polypeptides and for the production and delivery of therapeutic polypeptides by gene therapy or cell therapy. Homologous and other recombination methods may be used to modify a cell to express therapeutically efficacious amounts of Peptide E polypeptides.

Through homologous recombination, the DNA sequence to be inserted into the genome can be directed to a specific region of the gene of interest by attaching it to targeting DNA. The targeting DNA is a nucleotide sequence that is complementary (homologous) to a region of the genomic DNA. Small pieces of targeting DNA that are complementary to a specific region of the genome are put in contact with the parental strand during the DNA replication process. It is a general property of DNA that has been inserted into a cell to hybridize, and therefore, recombine with other pieces of endogenous DNA through shared homologous regions. If this complementary strand is attached to an oligonucleotide that contains a mutation or a different sequence or an additional nucleotide, it too is incorporated into the newly synthesized strand as a result of the recombination. As a result of the proofreading function, it is possible for the new sequence of DNA to serve as the template. Thus, the transferred DNA is incorporated into the genome.

Peptide E polypeptide cell therapy, e.g., the implantation of cells producing Peptide E polypeptides, is also contemplated. This embodiment involves implanting cells capable of synthesizing and secreting a biologically active form of Peptide E polypeptide. Such Peptide E polypeptide-producing cells can be cells that are natural producers of Peptide E polypeptides or may be recombinant cells whose ability to produce Peptide E polypeptides has been augmented by transformation with a gene encoding the desired Peptide E polypeptide or with a gene augmenting the expression of Peptide E polypeptide. Such a modification may be accomplished by means of a vector suitable for delivering the gene as well as promoting its expression and secretion. To minimize a potential immunological reaction in patients being administered a Peptide E polypeptide, as may occur with the administration of a polypeptide of a foreign species, it is preferred that the natural cells producing Peptide E polypeptide be of human origin and produce human Peptide E polypeptide. Likewise, it is preferred that the recombinant cells producing Peptide E polypeptide be transformed with an expression vector containing a gene encoding a human Peptide E polypeptide. Implanted cells may be encapsulated to avoid the infiltration of surrounding tissue.

In vivo and in vitro gene therapy delivery of Peptide E polypeptides are also envisioned. One example of a gene therapy technique is to use a Peptide E gene (either genomic DNA, cDNA, and/or synthetic DNA) encoding a Peptide E polypeptide, which may be operably linked to a constitutive or inducible promoter, to form a "gene therapy DNA construct." Other components of the gene therapy DNA construct may optionally include DNA molecules designed for site-specific integration (e.g., endogenous sequences useful for homologous recombination), tissue-specific promoters, enhancers or silencers, DNA molecules capable of providing a selective advantage over the parent cell, DNA molecules useful as labels to identify transformed cells, negative selection systems, cell specific binding agents (as, for example, for cell targeting), cell-specific internalization factors, transcription factors enhancing expression from a vector, and factors enabling vector production.

In yet other embodiments, regulatory elements can be included for the controlled expression of the Peptide E gene in the target cell. Such elements are turned on in response to an appropriate effector. In this way, a therapeutic polypeptide can be expressed when desired. One conventional control means involves the use of small molecule dimerizers or rapalogs to dimerize chimeric proteins which contain a small molecule-binding domain and a domain capable of initiating a biological process, such as a DNA-binding protein or transcriptional activation protein (see PCT Pub. Nos. WO 96/41865, WO 97/31898, and WO 97/31899). The dimerization of the proteins can be used to initiate transcription of the transgene.

In vivo gene therapy may be accomplished by introducing a polynucleotide encoding Peptide E polypeptide into cells via local injection of a Peptide E nucleic acid molecule or by other appropriate viral or non-viral delivery vectors. Hefti, 1994, *Neurobiology* 25:1418-35. For example, a nucleic acid molecule encoding a Peptide E polypeptide may be contained in an adeno-associated virus (AAV) vector for delivery to the targeted cells (see, e.g., Johnson, PCT Pub. No. WO 95/34670; PCT App. No. PCT/US95/07178). The recombinant AAV genome typically contains AAV inverted terminal repeats flanking a DNA sequence encoding a Peptide E polypeptide operably linked to functional promoter and polyadenylation sequences. Non-viral delivery methods are also suitable for use in the invention.

It is also contemplated that Peptide E cell therapy can further include the delivery of one or more additional polypeptide(s) in the same or a different cell(s). Such cells may be separately introduced into the patient, or the cells may be contained in a single implantable device, such as the encapsulating membrane described above, or the cells may be separately modified by means of viral vectors.

Therapeutic Uses

Peptide E nucleic acid molecules and polypeptides can be used to treat, diagnose, ameliorate, or prevent a number of diseases, disorders, or conditions, including those recited herein.

Peptide E nucleic acid molecules and polypeptides can also be used to treat, diagnose, ameliorate, or prevent diseases, disorders, or conditions involving weight disorders. Examples of such diseases include, but are not limited to obesity, anorexia, cachexia (including AIDS-induced cachexia), myopathies (e.g., muscle protein metabolism, such as in sepsis), and hypoglycemia. Various embodiments encompass other diseases involving weight disorders as well.

The Peptide E nucleic acid molecules, polypeptides, and agonists and antagonists can also be used to treat, diagnose, ameliorate, or prevent diseases, disorders, or conditions involving the reproductive system. Examples of such diseases include, but are not limited to infertility. Other diseases involving the reproductive system are encompassed within the scope of embodiments herein.

A Peptide E polypeptide may be administered as an adjunct to other therapy and also with other pharmaceutical compositions suitable for the indication being treated. A Peptide E polypeptide and any of one or more additional therapies or pharmaceutical formulations may be administered separately, sequentially, or simultaneously.

In another embodiment, a Peptide E polypeptide is provided in combination (pre-treatment, post-treatment, or concurrent treatment) with any of one or more diets, health supplements, treatments, therapies, and/or pharmaceutical compositions for the treatment or prevention of the diseases and disorders recited herein.

Uses of Peptide E Nucleic Acids and Polypeptides

Nucleic acid molecules (including those that do not themselves encode biologically active polypeptides) may be used to map the locations of the leptin gene and related genes on chromosomes. Mapping may be done by techniques known in the art, such as PCR amplification and in situ hybridization.

Peptide E nucleic acid molecules (including those that do not themselves encode biologically active polypeptides), may be useful as hybridization probes in diagnostic assays to test, either qualitatively or quantitatively, for the presence of leptin nucleic acid molecule in mammalian tissue or bodily fluid samples.

Isolation of the Peptide E polypeptide receptors is useful for identifying or developing novel agonists and antagonists of the Peptide E polypeptide signaling pathway. Such agonists and antagonists include soluble Peptide E polypeptide receptors, anti-Peptide E polypeptide receptor antibodies, small molecules, or antisense oligonucleotides, and they may be used for treating, preventing, or diagnosing one or more of the diseases or disorders described herein.

I claim:

1. An isolated polypeptide comprising the amino acid sequence of SEQ ID NO: 2, wherein the isolated polypeptide (i) has fewer than 44 amino acid residues, and (ii) is capable of restoring the physiological effects of human leptin.

2. A pharmaceutical composition comprising the polypeptide of claim 1.

3. A method for treating at least one illness or condition selected from the group consisting of obesity, inflammation, coronary artery disease, overeating, insulin resistance, infertility, and diabetes, comprising administering to a patient in need of treatment an effective amount of the pharmaceutical composition of claim 2.

4. A polypeptide complex comprising the polypeptide of claim 1 and, complexed with said polypeptide, at least one member of the group consisting of a mucoadhesive polymer, a polymeric nanoparticle, a dendrimer, biotin, and polyethylene glycol.

5. An oligomer comprising two or more polypeptides of claim 1.

6. A fusion peptide comprising at least one polypeptide of claim 1.

7. A peptidomimetic comprising the polypeptide of claim 1.

8. An isolated polypeptide comprising an amino acid sequence that differs from SEQ ID NO:2 by at least one modification that is (i) a conservative amino acid substitution, (ii) a C-terminal truncation, or (iii) a N-terminal truncation, wherein the isolated polypeptide (A) is at least 80% identical to the amino acid sequence of SEQ ID NO:2 and (B) is capable of restoring the physiological effects of human leptin.

9. The isolated polypeptide of claim 8, wherein the polypeptide is at least 90% identical to the amino acid sequence of SEQ ID NO:2.

10. A pharmaceutical composition comprising the polypeptide of claim 8.

11. A polypeptide complex comprising the polypeptide of claim 8 complexed with at least one member of the group consisting of a polymer, a mucoadhesive polymer, a polymeric nanoparticle, a dendrimer, biotin, and polyethylene glycol.

12. An oligomer comprising two or more polypeptides of claim 8.

13. A fusion peptide comprising at least one polypeptide of claim 8.

14. A peptidomimetic comprising the polypeptide of claim 8.

15. An isolated polypeptide comprising the amino acid sequence of an orthologue of SEQ ID NO:2, wherein the isolated polypeptide (i) has fewer than 44 amino acid residues and (ii) is capable of restoring the physiological effects of human leptin.

16. A pharmaceutical composition comprising the polypeptide of claim 15.

17. A polypeptide complex comprising the polypeptide of claim 15 complexed with at least one member of the group consisting of a polymer, a mucoadhesive polymer, a polymeric nanoparticle, a dendrimer, biotin, and polyethylene glycol.

18. An oligomer comprising two or more polypeptides of claim 15.

19. A fusion peptide comprising at least one polypeptide of claim 15.

20. A peptidomimetic comprising the polypeptide of claim 15.

\* \* \* \* \*